(12) United States Patent
Latham et al.

(10) Patent No.: US 9,777,330 B2
(45) Date of Patent: Oct. 3, 2017

(54) MPCR METHODS FOR ANALYZING REPEAT SEQUENCES

(75) Inventors: Gary J. Latham, Austin, TX (US); Liangjing Chen, Austin, TX (US); Andrew Hadd, Austin, TX (US); Sachin Sah, Austin, TX (US); Ru Cao, Austin, TX (US)

(73) Assignee: Asuragen, Inc., Austin, TX (US)

( * ) Notice: Subject to any disclaimer, the term of this patent is extended or adjusted under 35 U.S.C. 154(b) by 27 days.

(21) Appl. No.: 13/284,328

(22) Filed: Oct. 28, 2011

(65) Prior Publication Data

US 2012/0107824 A1    May 3, 2012

Related U.S. Application Data

(60) Provisional application No. 61/408,367, filed on Oct. 29, 2010.

(51) Int. Cl.
*C12P 19/34* (2006.01)
*C12Q 1/68* (2006.01)

(52) U.S. Cl.
CPC ......... *C12Q 1/6883* (2013.01); *C12Q 1/6858* (2013.01); *C12Q 2600/154* (2013.01); *C12Q 2600/166* (2013.01)

(58) Field of Classification Search
None
See application file for complete search history.

(56) References Cited

U.S. PATENT DOCUMENTS

| | | |
|---|---|---|
| 2008/0113355 A1 | 5/2008 | Hagerman et al. |
| 2010/0209970 A1 | 8/2010 | Latham |
| 2010/0243451 A1 | 9/2010 | Latham et al. |
| 2010/0248239 A1 | 9/2010 | Highsmith et al. |

FOREIGN PATENT DOCUMENTS

| | | | |
|---|---|---|---|
| WO | WO 92/12262 A1 | 7/1992 | |
| WO | WO 92/20825 A1 | 11/1992 | |
| WO | WO 03/027259 A2 | 4/2003 | |
| WO | WO 2007102891 A2 * | 9/2007 | |
| WO | WO 2008/011170 A2 | 1/2008 | |
| WO | WO 2011/070441 A2 | 6/2011 | |
| WO | WO 2011106368 A2 * | 9/2011 | |

OTHER PUBLICATIONS

Roberts et al. Restriction and modification enzymes and their recognition sequences. Nucleic Acids Research 1983;11(1):r135-r167.*
Nolin et al. Expansion of Fragile X CGG repeat in females with permutation or intermediate alleles. Am J Hum Genet 2003;72:454-464.*
Zhang et al. Genetic typing by capillary electrophoresis with the allelic ladder as an absolute standard. Anal Chem 1996;68(17):2927-2931.*
Bachinski et al., "Confirmation of the Type 2 Myotonic Dystrophy (CCTG)$_n$ Expansion Mutation in Patients with Proximal Myotonic Myopathy/Proximal Myotonic Dystrophy of Different European Origins: A Single Shared Haplotype Indicates an Ancestral Founder Effect," *Am. J. Hum. Genet.*, 73:835-848 (2003).
Boon et al., "Validation of two new PCR technologies for diagnostic testing of the Fragile X CGG repeat as well as *FMR1* methylation status," Poster presented in Jun. 2010.
Cagnoli et al., "Detection of Large Pathogenic Expansions in *FRDA1*, *SCA10*, and *SCA12* Genes Using a Simple Fluorescent Repeat-Primed PCR Assay," *Journal of Molecular Diagnostics*, 6(2):96-100 (2004).
Cagnoli et al., "Large Pathogenic Expansions in the *SCA2* and *SCA7* Genes Can Be Detected by Fluorescent Repeat-Primed Polymerase Chain Reaction Assay," *Journal of Molecular Diagnostics*, 8(1):128-132 (2006).
Carrel et al., "An Assay for X Inactivation Based on Differential Methylation at the Fragile X Locus, *FMRI*," *American Journal of Medical Genetics*, 64:27-30 (1996).
Chen et al., "An Information-Rich CGG Repeat Primed PCR That Detects the Full Range of Fragile X Expanded Alleles and Minimizes the Need for Southern Blot Analysis," *Journal of Molecular Diagnostics*, 12(5), DOI:10.2353/jmoldx.2010.090227, pp. 589-600 (Jul. 8, 2010).
Ciotti et al., "Triplet Repeat Primed PCR (TP PCR) in Molecular Diagnostic Testing for Friedreich Ataxia," *Journal of Molecular Diagnostics*, 6(4):285-289 (2004).
Dean et al., "Instability in the transmission of the myotonic dystrophy CTG repeat in human oocytes and preimplantation embryos," *Fertility and Sterility*, 86(1):98-105 (2006).
Dorschner et al., "Diagnosis of Five Spinocerebellar Ataxia Disorders by Multiplex Amplification and Capillary Electrophoresis," *Journal of Molecular Diagnostics*, 4(2):108-113 (2002).
Filipovic-Sadic et al., "A Novel *FMR1* PCR Method for the Routine Detection of Low Abundance Expanded Alleles and Full Mutations in Fragile X Syndrome," *Clinical Chemistry*, 56(3):399-408 (2010).
Godler et al., "Methylation of new markers of fragile X alleles is inversely correlated with FMRP expression and FMR1 activation ratio," *Human Molecular Genetics*, 19(8):1618-1632 (2010).
Hadd et al., "Two Novel PCR Strategies that Amplify and Correctly Characterize the Full Range of FMR1 Genotypes Without the Need for Southern Blot," Abstract G10, *Journal of Molecular Diagnostics*, 11(6):618-619 (Nov. 2009).
Hadd et al., "Applications of Novel PCR Technologies that Provide Enhanced Molecular Characterization of the Fragile X Gene," Platform presentation in Jul. 2010.
Haddad et al., "A PCR-based test suitable for screening for fragile X syndrome among mentally retarded males," *Hum Genet*, 97:808-812 (1996).
Kraff et al., "Screen for Excess *FMR1* Premutation Alleles Among Males With Parkinsonism," *Arch Neuro*, 64(7):1002-1006 (2007).
Latham et al., "A Rapid PCR Method for the Determination of FMR1 Methylation Status in both Males and Females," Poster presented in Nov. 2009.

(Continued)

*Primary Examiner* — Kenneth Horlick
(74) *Attorney, Agent, or Firm* — Finnegan, Henderson, Farabow, Garrett and Dunner LLP

(57) ABSTRACT

Methods are provided for determining the methylation status of GC-rich templates. The methods include use of GC reference standards that allow simultaneous characterization of methylation status and CGG repeat length. The methods are useful for detecting genotypes associated with GC-rich repeats, including Fragile X Syndrome.

37 Claims, 30 Drawing Sheets

(56) References Cited

OTHER PUBLICATIONS

Latham et al., "A Rapid PCR Method for the Determination of FMR1 Methylation Status in both Males and Females," Abstract G11, *Journal of Molecular Diagnostics*, 11(6):619 (Nov. 2009).
Latham et al., "A PCR—only Workflow for FMR1 Analysis that Reproducibly Amplifies Fragile X Full Mutation Alleles, Definitively Resolves Allele Zygosity, and Accurately Assesses Methylation Status," 2010 American College of Medical Genetics Meeting, abstract available online approximately Feb./Mar. 2010.
Latham et al., "A PCR—only Workflow for FMR1 Analysis that Amplifies Fragile X Full Mutation Alleles, Definitively Resolves Allele Zygosity, and Accurately Assesses Methylation Status," Poster presented in Mar. 2010.
Nygren et al., "Methylation-Specific Multiplex Ligation-Dependent Probe Amplification Enables a Rapid and Reliable Distinction between Male *FMR1* Premutation and Full-Mutation Alleles," *Journal of Molecular Diagnostics*, 10(6):496-501 (2008).
O'Connell et al., "Standardization of PCR amplification for fragile X trinucleotide repeat measurements," *Clin Genet*, 61:13-20 (2002).
Panagopoulos et al., "A Methylation PCR Approach for Detection of Fragile X Syndrome," *Human Mutation*, 14:71-79 (1999).
Saluto et al., "An Enhanced Polymerase Chain Reaction Assay to Detect Pre- and Full Mutation Alleles of the *Fragile X Mental Retardation 1* Gene," *Journal of Molecular Diagnostics*, 7(5):605-612 (2005).
Sermon et al., "Preimplantation Diagnosis for Fragile X Syndrome Based on the Detection of the Non-expanded Paternal and Maternal CGG," *Prenat. Diagn.* 19:1223-1230 (1999).
Sermon et al., "PGD in the lab for triplet repeat diseases—myotonic dystrophy, Huntington's disease and Fragile-X syndrome," *Molecular and Cellular Endocrinology*, 183:S77-S85 (2001).
Sherman et al., "Fragile X syndrome: Diagnostic and carrier testing," *Genetics IN Medicine*, 7(8):584-587 (2005).
Strom et al., "Development of a novel, accurate, automated, rapid, high-throughput technique suitable for population-based carrier screening for Fragile X syndrome," *Genetics IN Medicine*, 9(4):199-207 (2007).
Tassone et al., "A Rapid Polymerase Chain Reaction-Based Screening Method for Identification of All Expanded Alleles of the Fragile X (*FMR1*) Gene in Newborn and High-Risk Populations," *The Journal of Molecular Diagnostics*, 10(1):43-49 (2008).
Warner et al., "A general method for the detection of large CAG repeat expansions by fluorescent PCR," *J. Med. Genet.*, 33:1022-1026 (1996).
Weinhäusel et al., "Evaluation of the fragile X (FRAXA) syndrome with methylation-sensitive PCR," *Hum Genet*, 108:450-458 (2001).
Wilson et al., "Consensus Characterization of 16 *FMR1* Reference Materials: A Consortium Study," *Journal of Molecular Diagnostics*, 10(1):2-12 (2008).
Zhou et al., "Robust fragile X (CGG)n genotype classification using a methylation specific triple PCR assay," *J. Med. Genet.*, 41:e15, 8 pages (2004).
Zhou et al, "Simplified Molecular Diagnosis of Fragile X Syndrome by Fluorescent Methylation-Specific PCR and GeneScan Analysis," *Clinical Chemistry* 52(8), doi:10.1373/clinchem.2006.068593, 9 pages (2006).
Anonymous, "HUGO gene nomenclature committee report for FMR", Retrieved from Internet: URL:http://www.genenames.org/cgi-bin/quick_search.pl?.cgifields=type&type=contains&num=50&search=fmr&submit=Submit (retrieved on Feb. 3, 2012).
Chen et al., "High-resolution methylation polymerase chain reaction for fragile X analysis: Evidence for novel *FMR1* methylation patterns undetected in Southern blot analyses," *Genetics in Medicine*, 13(6): 528-538 (2011).
Kline et al., "X-chromosome inactivation and ovarian age during the reproductive years," *Fertility and Sterility*, 85(5): 1488-1495 (2006).
Richards et al., "Quantitative Analysis of Gene Expression by Reverse Transcription Polymerase Chain Reaction and Capillary Electrophoresis with Laser-Induced Fluorescence Detection," *Molecular Biotechnology*, 21(1): 19-387(2002).
Speckman et al., "Clinical and immunologic consequences of a somatic reversion in a patient with X-linked severe combined immunodeficiency," *Blood*, 112(10): 4090-4097 (2008).
PCT International Search Report and Written Opinion mailed Feb. 16, 2012, for International Application No. PCT/2011/058453.
S.E. Antonarakis, "Human Genome Sequence and Variation," from *Vogel and Motulsky's Human Genetics: Problems and Approaches*, M.R. Speicher et al. (eds.), Springer-Verlag Berlin Heidelberg, pp. 31-53 (2010).
Costa, et al., "Intermediate Alleles at the *FRAXA* and *FRAXE* Loci in Parkinson's Disease," *Parkinsonism and Related Disorders* 17(4):281-284 (2011).
Richards and Poch, "Quantitative Analysis of Gene Expression by Reverse Transcription Polymerase Chain Reaction and Capillary Electrophoresis with Laser-Induced Fluorescence Detection," *Molecular Biotechnology* 21:19-37 (2002).

\* cited by examiner

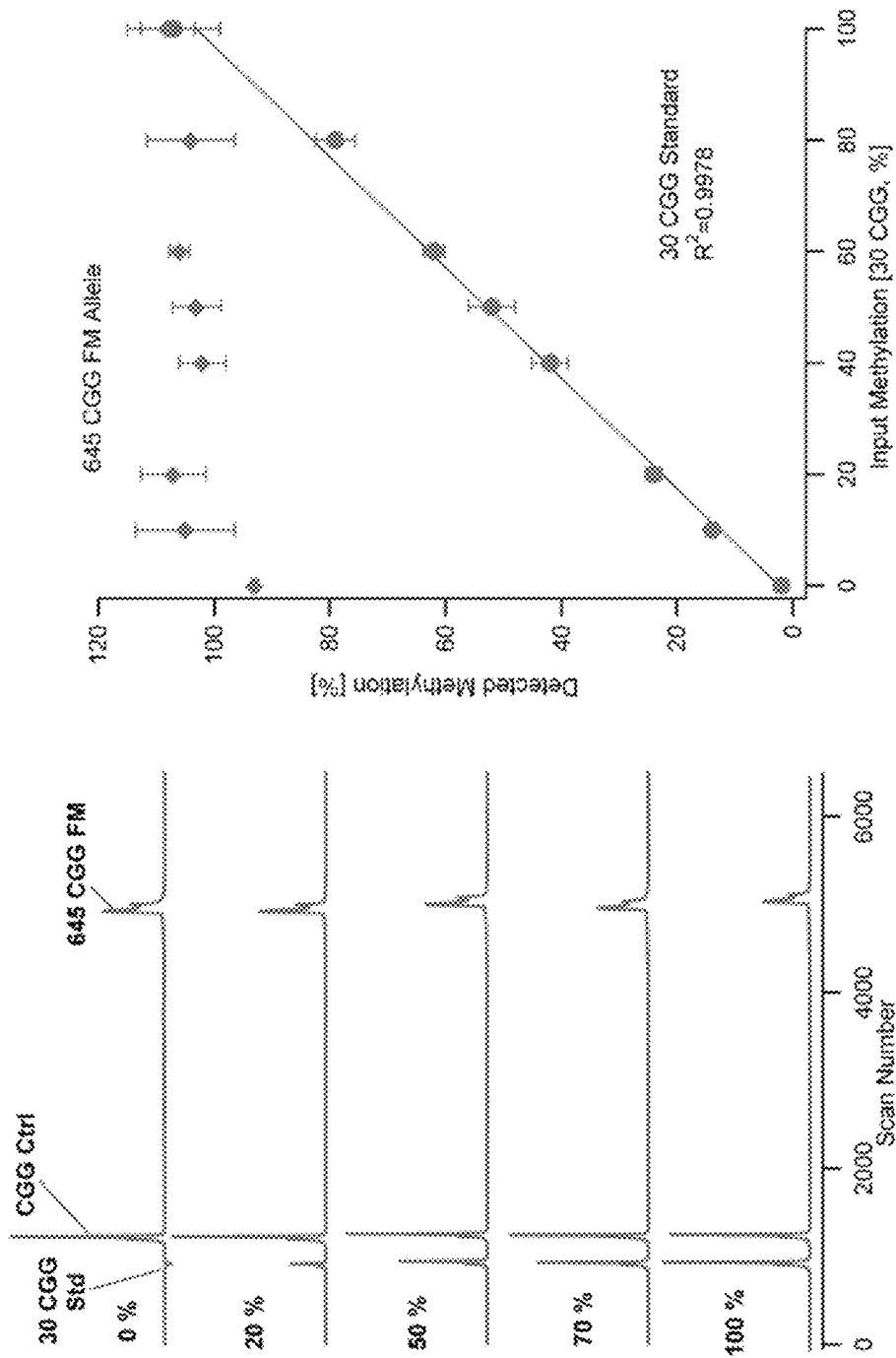

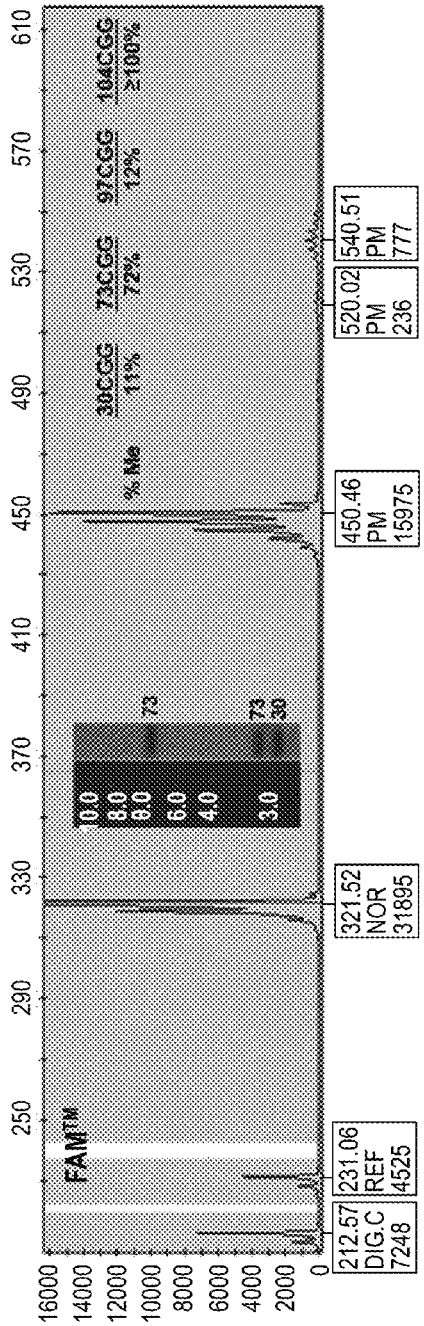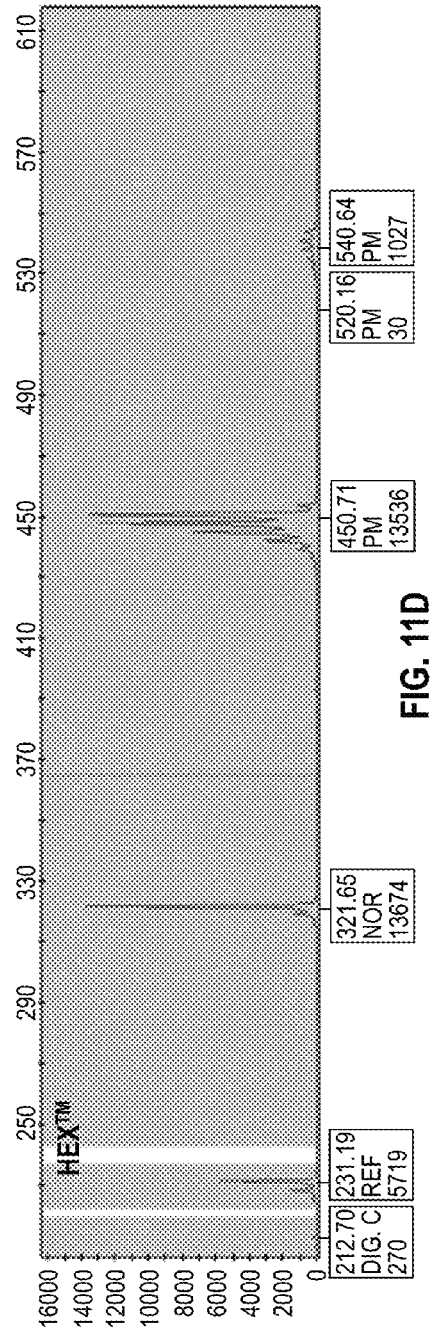
FIG. 11D

MPCR METHODS FOR ANALYZING REPEAT SEQUENCES

This application claims the benefit of U.S. Provisional Application No. 61/408,367, filed Oct. 29, 2010, which is incorporated by reference herein in its entirety.

Work described in this application was partially funded by the Federal government under Grants No. R43HD060450 and R44HD060450 from the Eunice Kennedy Shriver National Institute of Child Health & Human Development. Accordingly, the Federal government may have certain rights in this invention.

SEQUENCE LISTING

The instant application contains a Sequence Listing which has been submitted in ASCII format via EFS-Web and is hereby incorporated by reference in its entirety. Said ASCII copy, created on Jul. 25, 2013, is named 10256.0037-00000_SL.txt and is 18,273 bytes in size.

This invention is in the field of nucleic acid analysis, particularly relating to methods for determining the methylation status of GC-rich templates and products. In addition, the invention relates to GC reference standards that may be used according to the methods described herein.

In certain embodiments, the methods described herein are used to determine the methylation status of a GC-rich locus. In some circumstances, expansion of GC-rich regions is associated with various disease states. An example of a locus associated with the expansion of CGG repeats is the 5' untranslated region (UTR) of the Fragile X Mental Retardation-1 gene (FMR1) on the X chromosome. Expansions in this region to greater than 200 CGG repeats are associated with hypermethylation of the FMR1 gene and are referred to as "full mutation" alleles. These alleles are associated with the loss of FMR1 protein production, and the disorder Fragile X Syndrome (FXS). FXS may include mental retardation, autism, premature ovarian failure, and other cognitive and behavioral conditions. (J. Mol Diag. 10(6): 496-501 (2008)).

Methods for determining the methylation status of GC-rich templates, and of FMR1, include Southern blot (SB) analysis and polymerase chain reaction (PCR) strategies. SB analysis provides a crude measure of the size of triplet repeat regions and an assessment of methylation. A methylation-sensitive enzyme, which does not cleave methylated sites, may be used to distinguish between methylated and unmethylated alleles. However, the determination of methylation status by SB analysis is limited to alleles that are well resolved by gel electrophoresis. SB analysis is also limited by the amount of genomic DNA (gDNA) material that is required and a tedious workflow that is incompatible with high throughput procedures. (Genet. Med. 7(8): 584-587 (2005)).

PCR strategies may provide greater accuracy in determining the size of the triplet repeat regions. However, limitations in the amplification of long GC-rich sequences, including full mutation alleles of the FMR1 5' UTR, have restricted the quantification of repeat regions. Optimizations to the PCR of FMR1, for example, have been attempted, and include modifications to conventional PCR assay conditions. (See Genome Res. 6(7): 633-8, (1996); J. Mol. Diagn. 8: 544-550, (2006); and Am J Med Genet. 51(4): 527-34, (1994)). More recently, a PCR technique has been developed that permits reliable amplification of over 200 CGG repeats. See US Application No. 2010/0209970, incorporated herein by reference in its entirety. However, PCR alone does not permit the characterization of methylation status of a GC-rich template.

Several strategies combine PCR with other methods for assessing methylation. Most of the methods have exploited the resistance of 5-methylcytosine to bisulfite conversion to reveal methylation status. However, for FMR1, for example, bisulfite-based methylation PCR methods have been practically limited to evaluations of male samples only, due to the mixed methylation states that confound interpretations of female samples, and/or the methods have demonstrated limited utility for expanded alleles. (See Hum. Mutation 14: 71-79, (1999); Clin. Chem. 52: 1492-1500, (2006); J. Med. Genet. 41: 1-8, (2004); and Hum. Genet. 108: 450-458, (2001)). Alternatives to bisulfite treatment, such as the use of methylation-sensitive restriction enzymes, have been reported, however, the analysis of female samples remains problematic. (J. Mol Diag. 10(6): 496-501, (2008)).

To date, no single approach other than SB has demonstrated accurate methylation assessments for expanded alleles in both male and female samples. Therefore, a need remains for a rapid, accurate, assay with a simple workflow that can be used to characterize the methylation and repeat status of a GC-rich locus.

The methods described herein relate to a PCR-based technology that can detect and resolve methylation status across the spectrum of GC-rich repeat lengths in both male and female samples. The overall workflow is amenable to routine testing and high throughput screening applications, and provides the foundation for comprehensive FMR1 analyses without the requirement for SB analysis.

In one embodiment, the methods relate to characterizing a FMR locus in a DNA sample comprising the steps of:
a) contacting a first portion of the sample with a methylation-sensitive DNase;
b) adding a GC reference standard to the sample, wherein the reference standard has at least 75% GC-richness;
c) subjecting the first portion and a second portion of the sample, each containing the GC reference standard, to a DNA amplification reaction, wherein the amplified DNA in each portion is labeled with a different label; and
d) analyzing the amplified DNA from the first and the second portion of the sample, thereby characterizing the methylation status of the FMR locus.

In certain embodiments, step (d) comprises capillary electrophoresis (CE). In additional embodiments, the amplified DNA from the first and the second portion are analyzed in a single CE run. In some methods, the GC reference standard is devoid of recognition sites for the methylation-sensitive DNase. In certain methods, the GC reference standard has a CE migration time that does not overlap with a naturally occurring FMR allele. For example, the GC reference standard may have a relative retention time of less than about 20, about 24 to 27, or greater than about 32 CGG repeats. In additional examples, the GC reference standard has a relative retention time of about 175 to about 225 CGG repeats. In some embodiments, the GC reference standard is added to the sample after contacting the first portion with the DNase.

In other embodiments, the amplification reaction is capable of amplifying at least 200 CGG repeats. Certain amplification reactions comprise a dNTP mixture with a GC/AT ratio greater than 1, such as from about 2.5 to about 10. In certain methods, the FMR locus is FMR1. In some methods the methylation-sensitive DNase is chosen from Hpa II, Eag I, or Nru I.

In further embodiments, the second portion of the sample is contacted with a control enzyme. In some instances, the control enzyme is chosen from EcoRI and Sau3A1. In other instances, the control enzyme is chosen from EcoRI, DpnI, NaeI, and HINDIII-HF®.

Certain embodiments described herein relate to a method of analyzing a human DNA sample comprising the steps of:

a) contacting a first portion of the sample with a methylation-sensitive DNase;

b) adding a GC reference standard to the sample, wherein the reference standard has at least 75% GC-richness;

c) subjecting the first portion and a second portion of the sample to a DNA amplification reaction, wherein the amplified DNA in each portion is labeled with a different label; and d) analyzing the amplified DNA from the first and the second portion of the sample, thereby detecting a genotype associated with FXS, Fragile X-associated tremor ataxia syndrome, and/or Fragile X-associated primary ovarian insufficiency.

Certain embodiments described herein relate to a GC reference standard comprising a nucleic acid sequence of the formula: 5'-A-B-C-3', wherein A is a sequence comprising at least 10 consecutive nucleotides of SEQ ID NO: 40 wherein A is capable of specifically hybridizing to a genomic FMR1 5' untranslated region; C is a sequence comprising at least 10 consecutive nucleotides of SEQ ID NO: 41 wherein C is capable of specifically hybridizing to a genomic FMR1 5' untranslated region; and B is a sequence having at least 75% GC-richness, and is between X−300 and X+10 nucleotides in length. X is the sum of a) the number of nucleotides between the 3' end of A and the last nucleotide of SEQ ID NO: 40; and b) the number of nucleotides from the first nucleotide of SEQ ID NO: 41 to the 5' end of C.

In certain embodiments, B is between 150 and 200 nucleotides in length. In additional embodiments, B has at least 90% GC-richness. In further embodiments, B has at least 94% GC-richness. In one embodiment, A comprises GCGCTCAGCTCCGTTTCGGT (SEQ ID NO: 17). In an additional embodiment, C comprises AGTGCGGGGCTC-CAATGGCG (SEQ ID NO: 39).

It is to be understood that both the foregoing general description and the following detailed description are exemplary and explanatory only and are not restrictive of the invention, as claimed.

BRIEF DESCRIPTION OF THE DRAWINGS

FIG. 3A shows electropherograms of methylated DNA standards with known fractions of FMR1 methylation. Each trace includes the profile of the DNA standard in the background of a full mutation allele from cell line DNA (~645 CGG).

FIG. 3B shows a plot of the linear fit of known input methylated DNA standards versus detected percent methylation. Quantification of the background, fully methylated 645 CGG allele is superimposed (Mean=104±5%).

FIGS. 11A-D show representative capillary electropherograms of 4 cell line DNA samples subjected to an mPCR assay according to the alternative workflow of FIG. 10, with comparative data from a parallel Southern blot analysis. Provided in boxes beneath the peaks are raw retention time (first row), peak identity (second row), and peak intensity (third row). Peak intensities are expressed as maximum fluorescence (peak height) in arbitrary fluorescence units. Peak identity abbreviations are as follows: DIG.C=digestion control; REF=GC reference standard; FM=full mutation allele; PM=premutation allele; NOR=normal allele.

EXEMPLARY EMBODIMENTS

Figure 1:
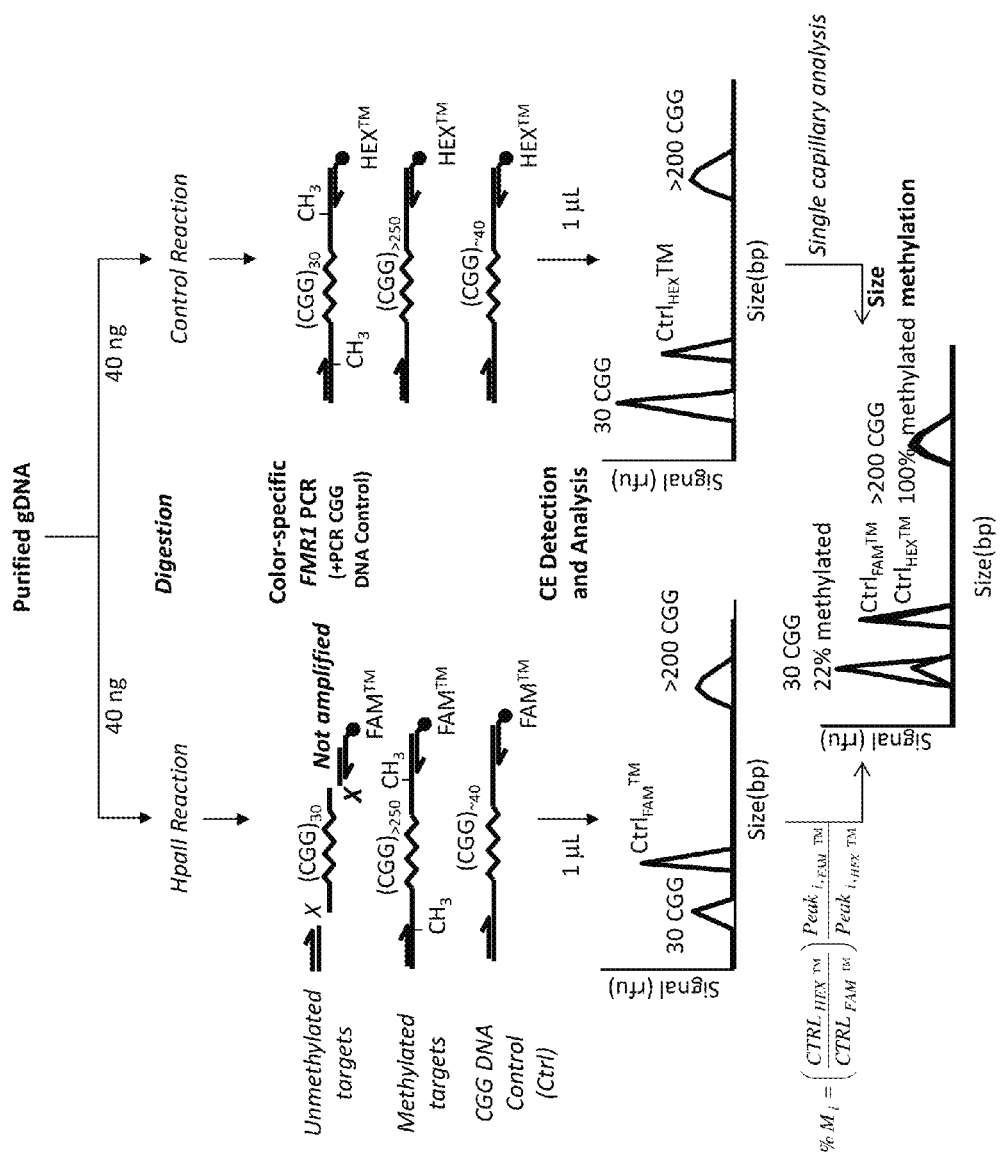
FIG. 1 provides an example of the procedural workflow for determining methylation status of GC-rich alleles in which HpaII is used as the methylation-sensitive DNase.

In certain aspects, the invention provides methods for characterizing the methylation status of GC-rich nucleic acid templates. In exemplary embodiments, the methods involve treatment with a methylation-sensitive DNase in combination with PCR in the presence of a GC reference standard. The methods described herein may be referred to as "mPCR" methods.

To assist in understanding the present invention, certain terms are first defined. Additional definitions are provided throughout the application.

The use of the word "a", "an" or "the" when used in conjunction with the term "comprising" in the claims and/or the specification may mean "one," but it is also consistent with the meaning of "one or more," "at least one," and "one or more than one."

"GC/AT Ratio" means the ratio of the concentration of the sum of dCTP, dGTP, and all nucleotide analogs thereof, to the concentration of the sum of dATP, dTTP, dUTP, and all nucleotide analogs thereof, in a given solution or mixture.

"dNTP" stands for deoxynucleotide triphosphate and refers to dATP, dCTP, dGTP, dTTP, dUTP, and analogs thereof.

"Nucleotide analogs" are molecules or ions comprising a base moiety other than the natural bases adenine (A), cytosine (C), guanine (G), thymine (T), or uracil (U), a sugar moiety identical or similar to deoxyribose, and at least one phosphate or multiple phosphate (e.g., diphosphate or triphosphate) moiety. The nucleotide analog is an analog of a specific nucleotide, in particular dATP, dCTP, dGTP, dTTP, or dUTP, when it comprises a triphosphate and a sugar moiety, the structure and configuration of both of which are suitable for incorporation into a nucleic acid double helix by a polymerase, and a base whose base pairing properties in a nucleic acid double helix and loci of incorporation by DNA polymerases in a nucleic acid double helix are most similar to one of the five previously listed nucleotides, with the exception that analogs of dTTP will generally also be analogs of dUTP and vice versa.

"GC-richness" is the fraction or percentage of total nucleobase residues in a nucleic acid that are guanine residues, cytosine residues, or analogs thereof. For example, a 100 nt nucleic acid that contains exactly 30 cytosines, exactly 30 guanines, exactly one cytosine analog, and exactly one guanine analog has a GC-richness of 62%. In some embodiments, a GC-rich template may contain at least 51, 55, 60, 65, 70, 75, 80, 85, 90, 95, 96, 97, 98, 99, or 99.5% guanine residues, cytosine residues, or analogs thereof.

I. METHODS OF CHARACTERIZING METHYLATION STATUS

In certain embodiments, the invention relates to methods of characterizing the methylation status of a GC-rich nucleic acid template. Generally, the methods include the steps of contacting a first portion of a sample with a methylation-sensitive DNase, adding a GC reference standard to the sample, subjecting the first portion and a second portion of the sample to a nucleic acid amplification reaction, and analyzing the amplified nucleic acids from the first and the second portions of the sample. In some embodiments, the first portion and second portion are differentially labeled.

In further embodiments, the second portion is contacted with a control enzyme prior to amplification, where the control enzyme does not cleave the amplified sequence. The control enzyme can be chosen from, for example, EcoRI, DpnI, NaeI, and HINDIII-HF®. Additional possibilities include Sau3A, NheI, TfiI, ApaLI, MluCI, NcoI, ScaI, StuI, XmnI and Hpy16611. In some embodiments, the control enzyme is chosen from a restriction endonuclease with a recognition site that does not occur within the region that is amplified by the DNA amplification reaction. In some embodiments, the control enzyme is chosen from enzymes that exhibit little if any nonspecific cleavage (star activity) at non-target sites within the region that is amplified by the DNA amplification reaction, such as less than 20%, 15%, 10%, 5%, 3%, or 1% cleavage of non-target sites within the region that is amplified by the DNA amplification reaction. The extent of cleavage is expressed in terms of the fraction of molecules undergoing at least one cleavage event within the region that is amplified by the DNA amplification reaction.

In additional embodiments, the analysis of the first and second portion are performed in a single assay.

Figure 10:
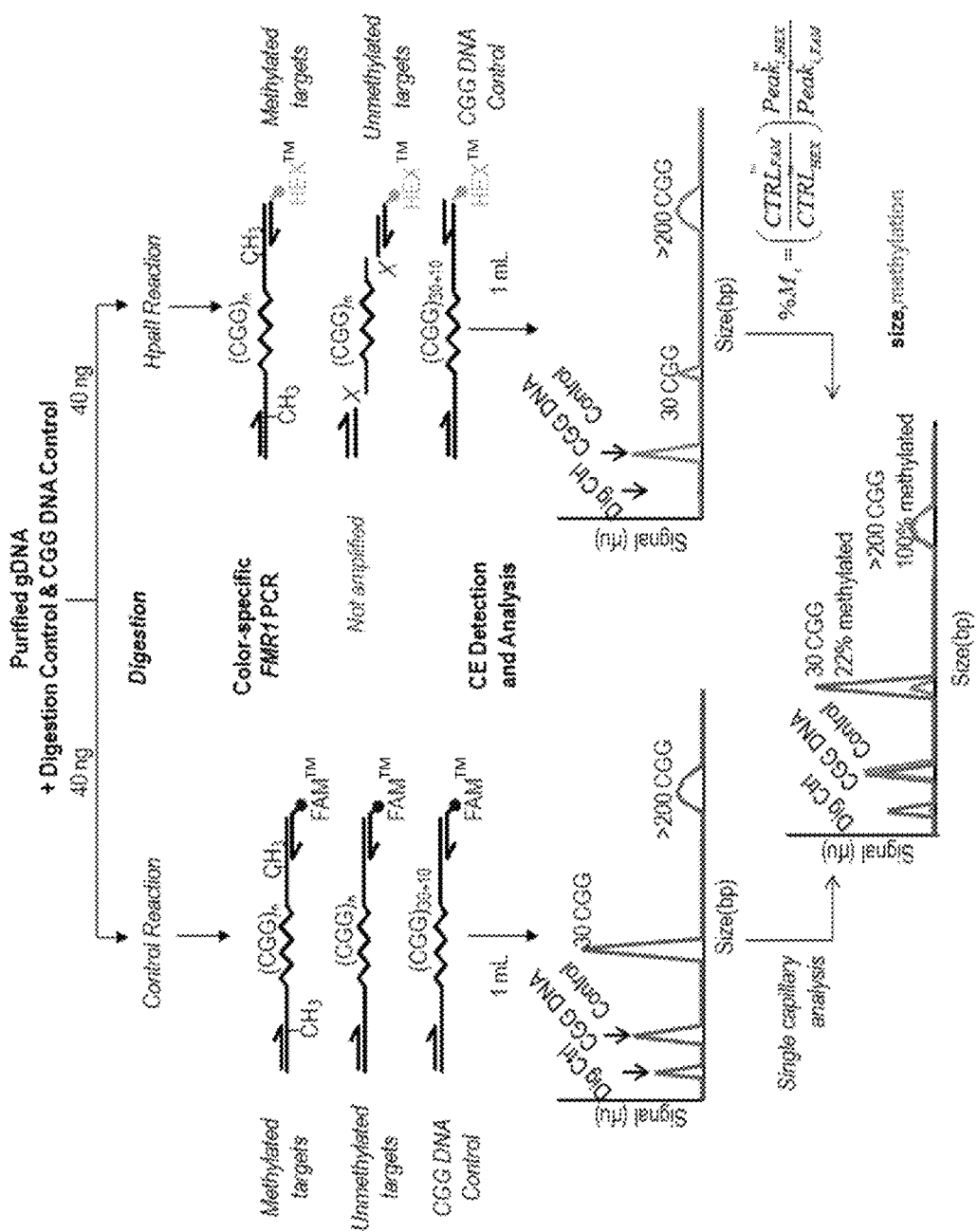
FIG. 10 shows an alternative procedural workflow for determining methylation status of GC-rich alleles and a digestion control and CGG DNA control (CGG reference standard) are added to the sample before dividing the sample into two portions and conducting digestion reactions, in one of which HpaII is used as the methylation-sensitive DNase.
Figure 11A:
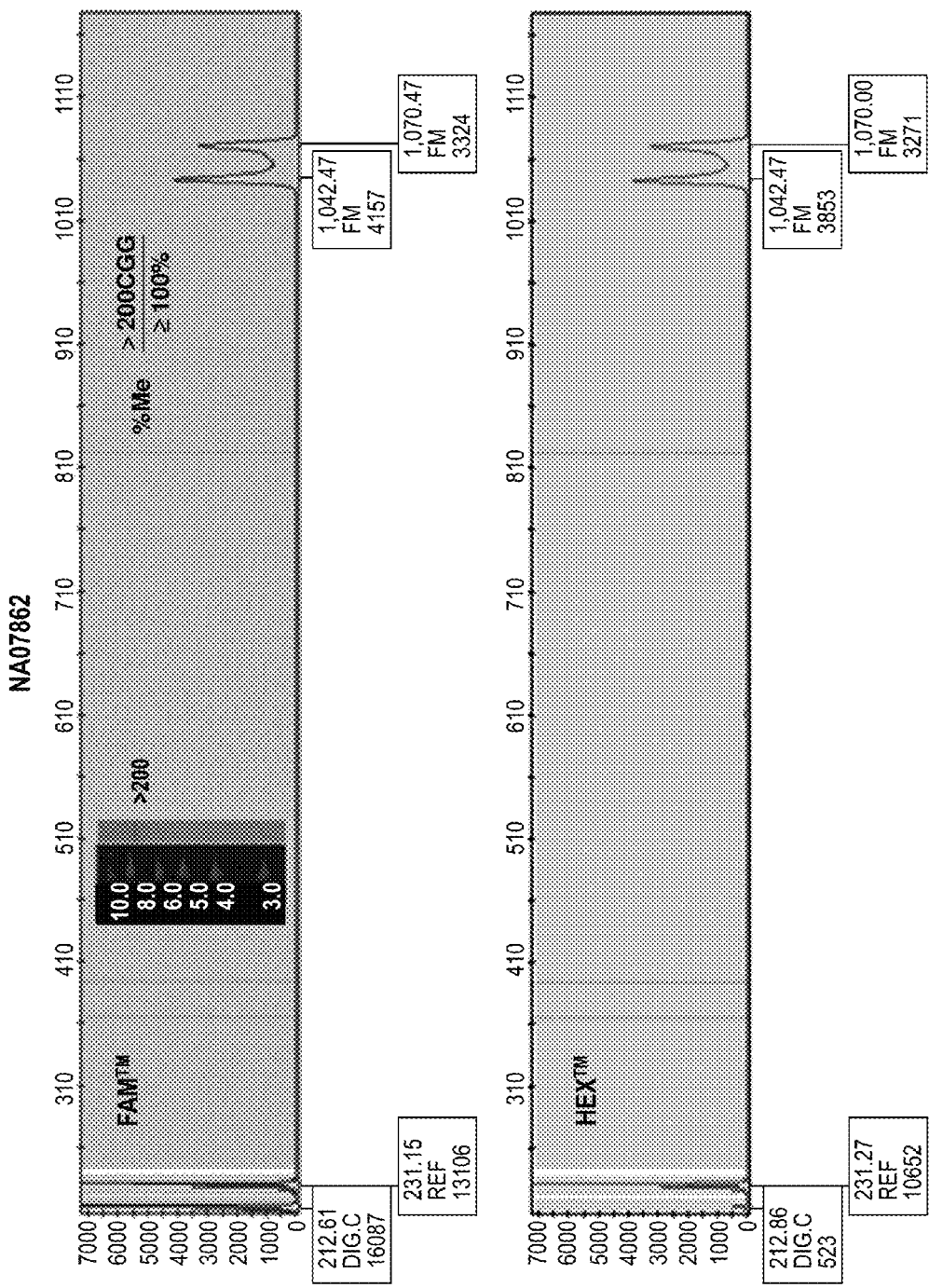
Figure 11B:
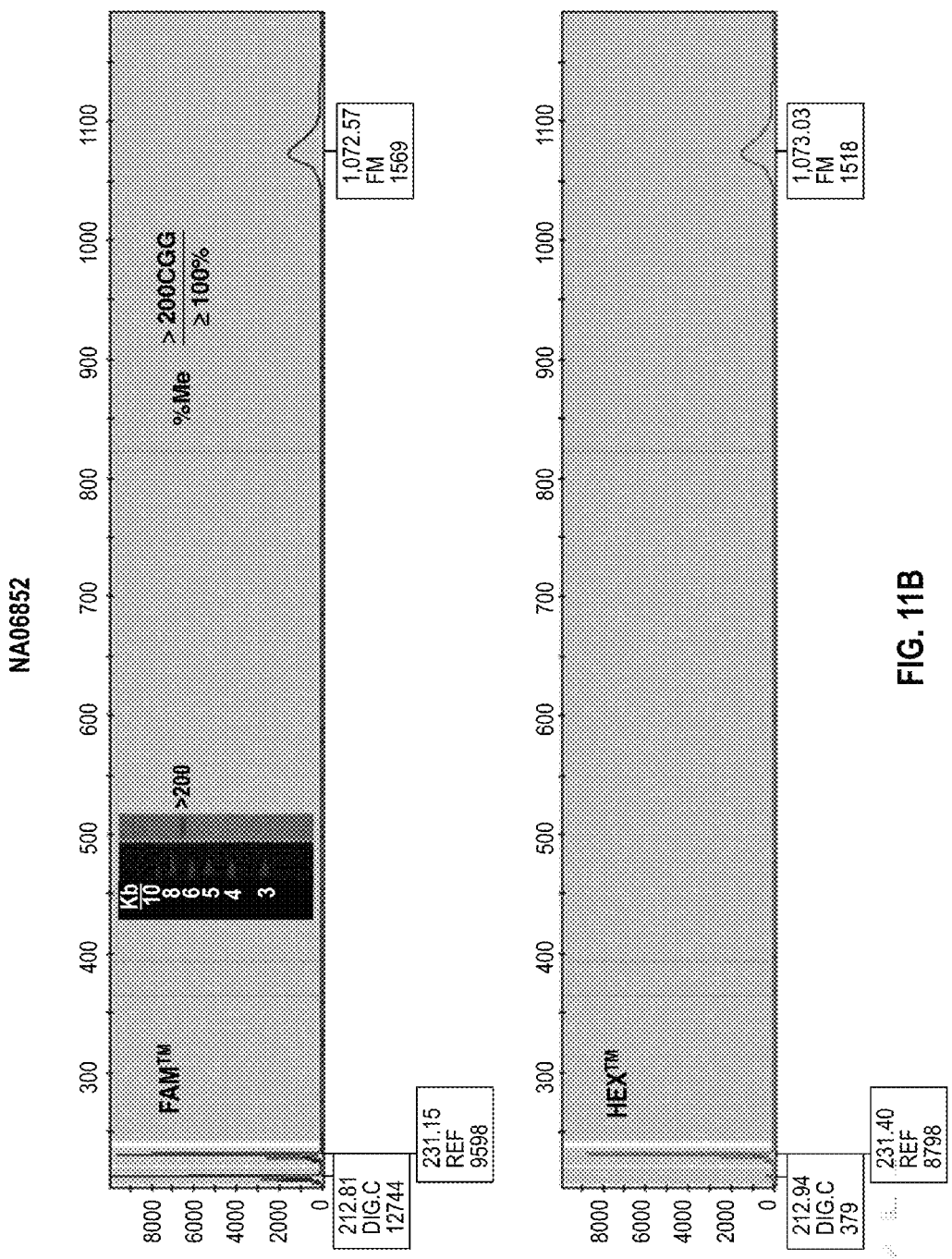
Figure 11C:
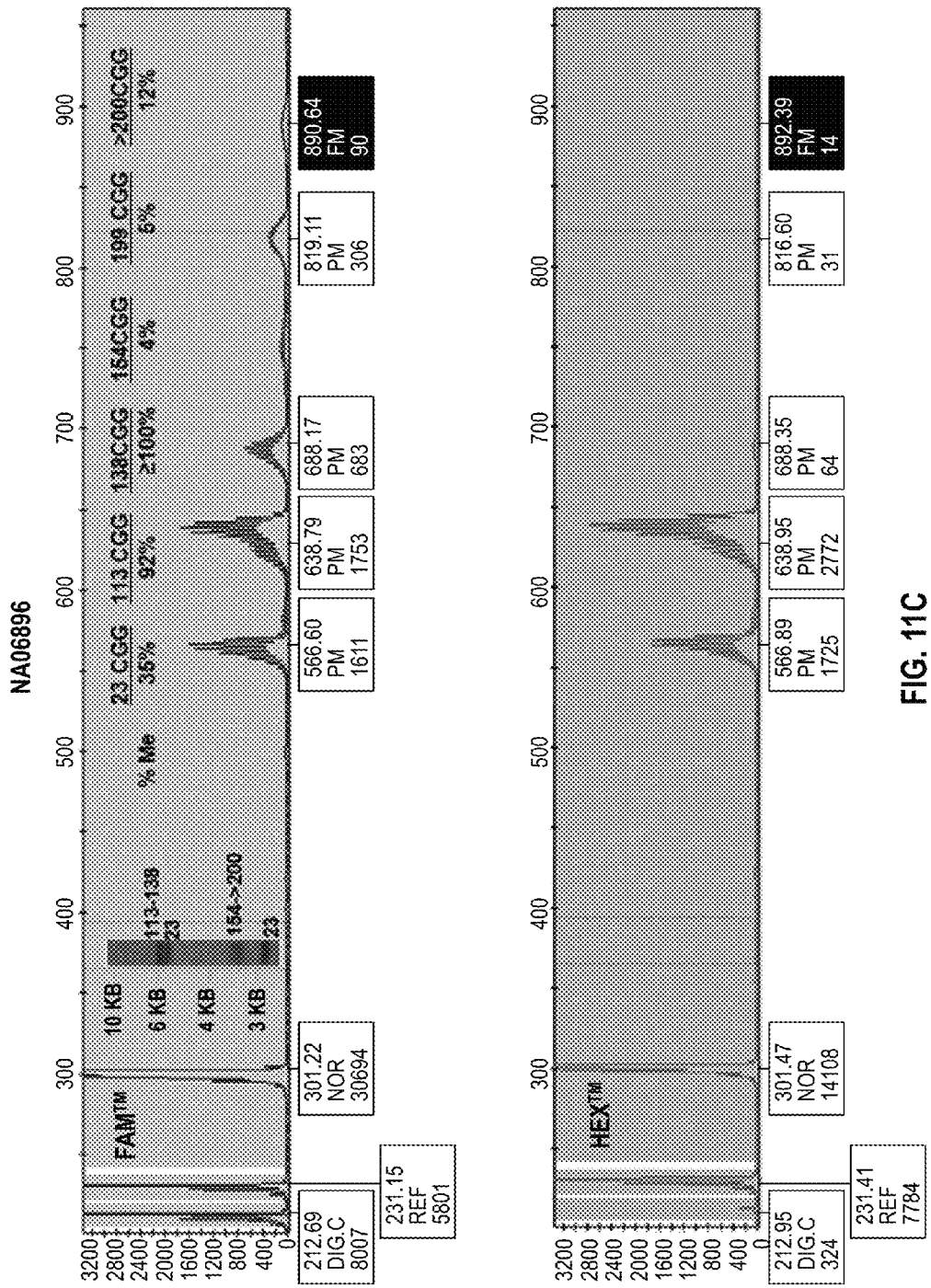
Figure 12A:
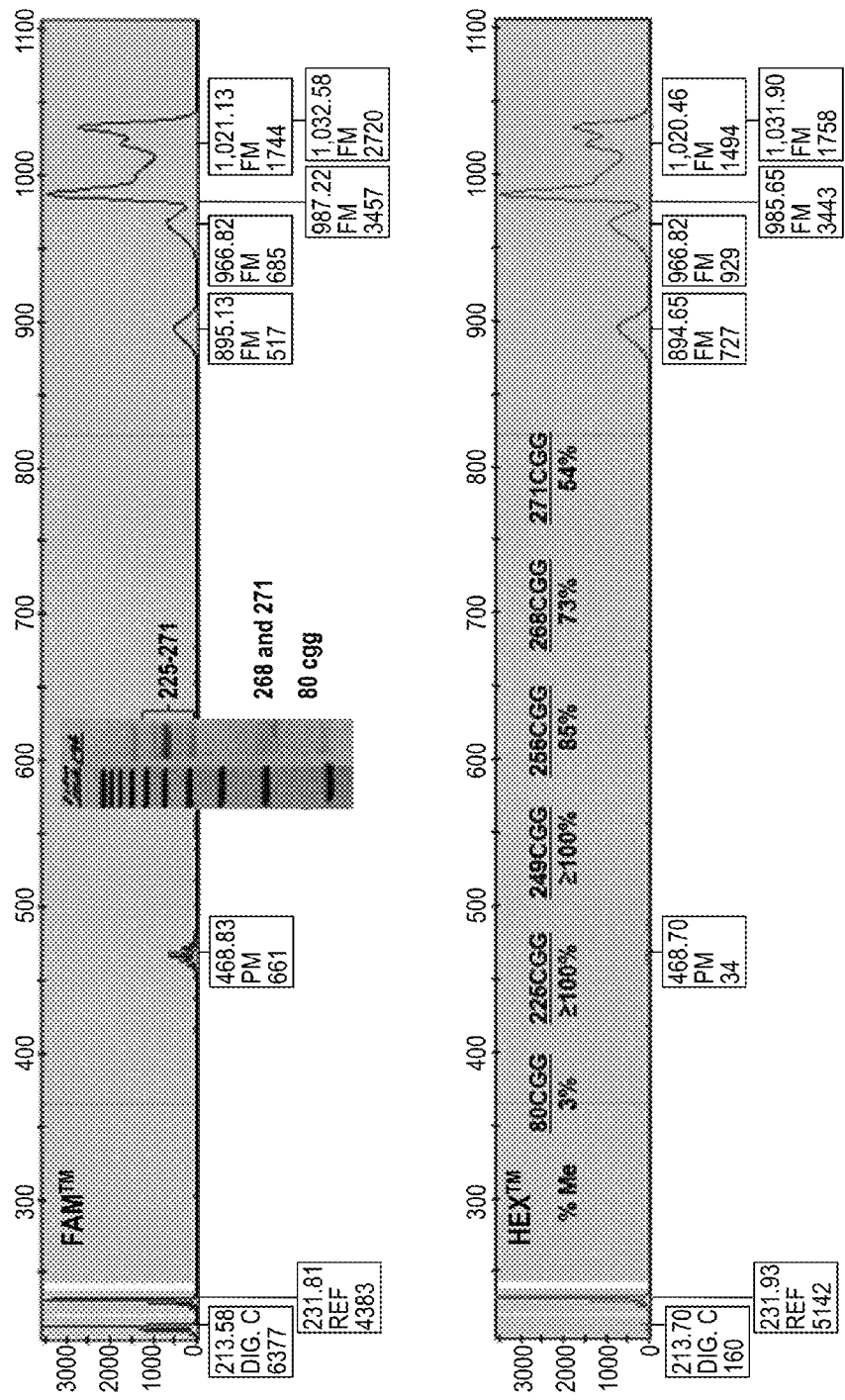
FIGS. 12A-G show representative capillary electropherograms of 7 clinical specimens subjected to an mPCR assay according to the alternative workflow of FIG. 10, with comparative data from a parallel Southern blot analysis. Boxes beneath the peaks provide information as in FIGS. 11A-D.
Figure 12B:
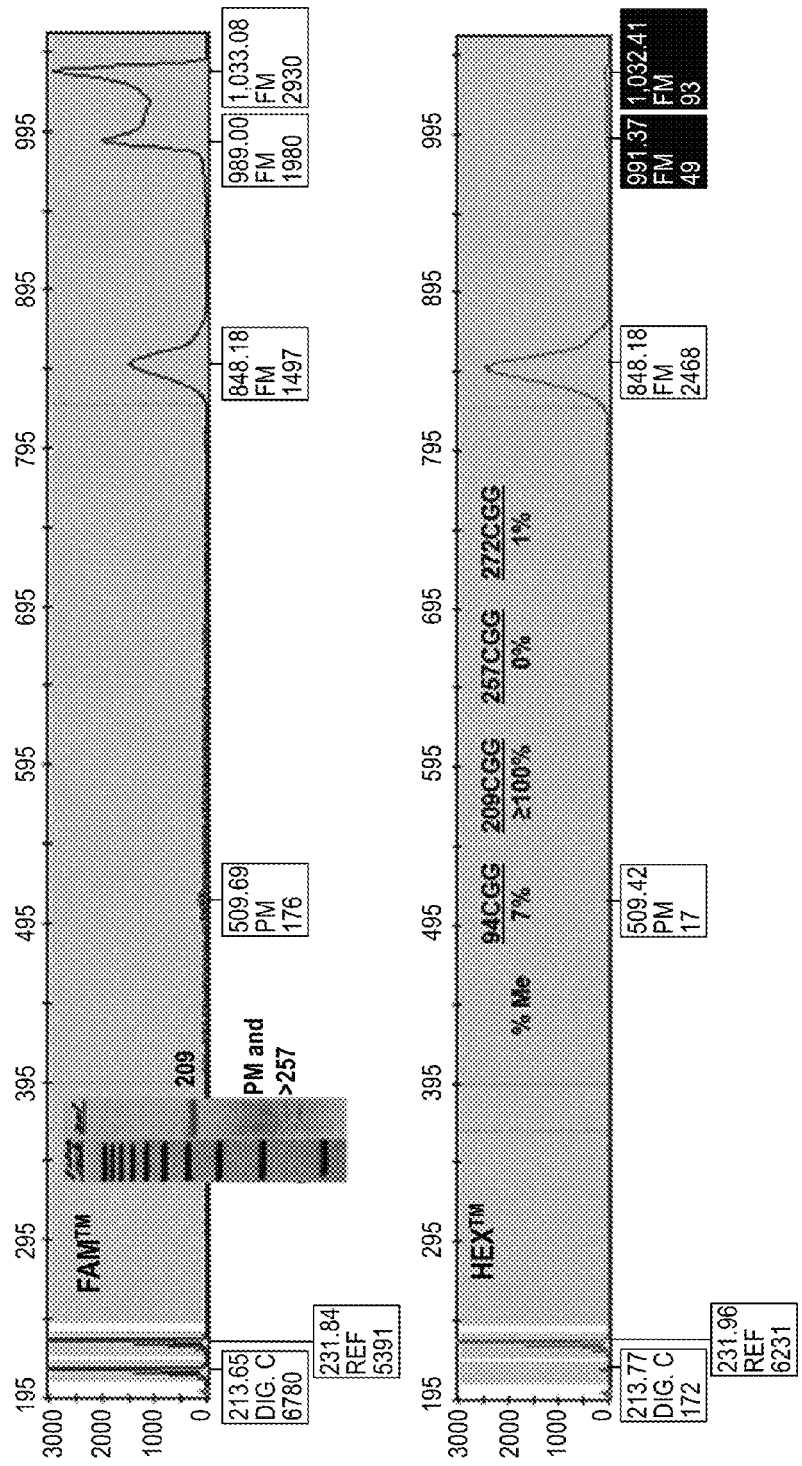
Figure 12C:
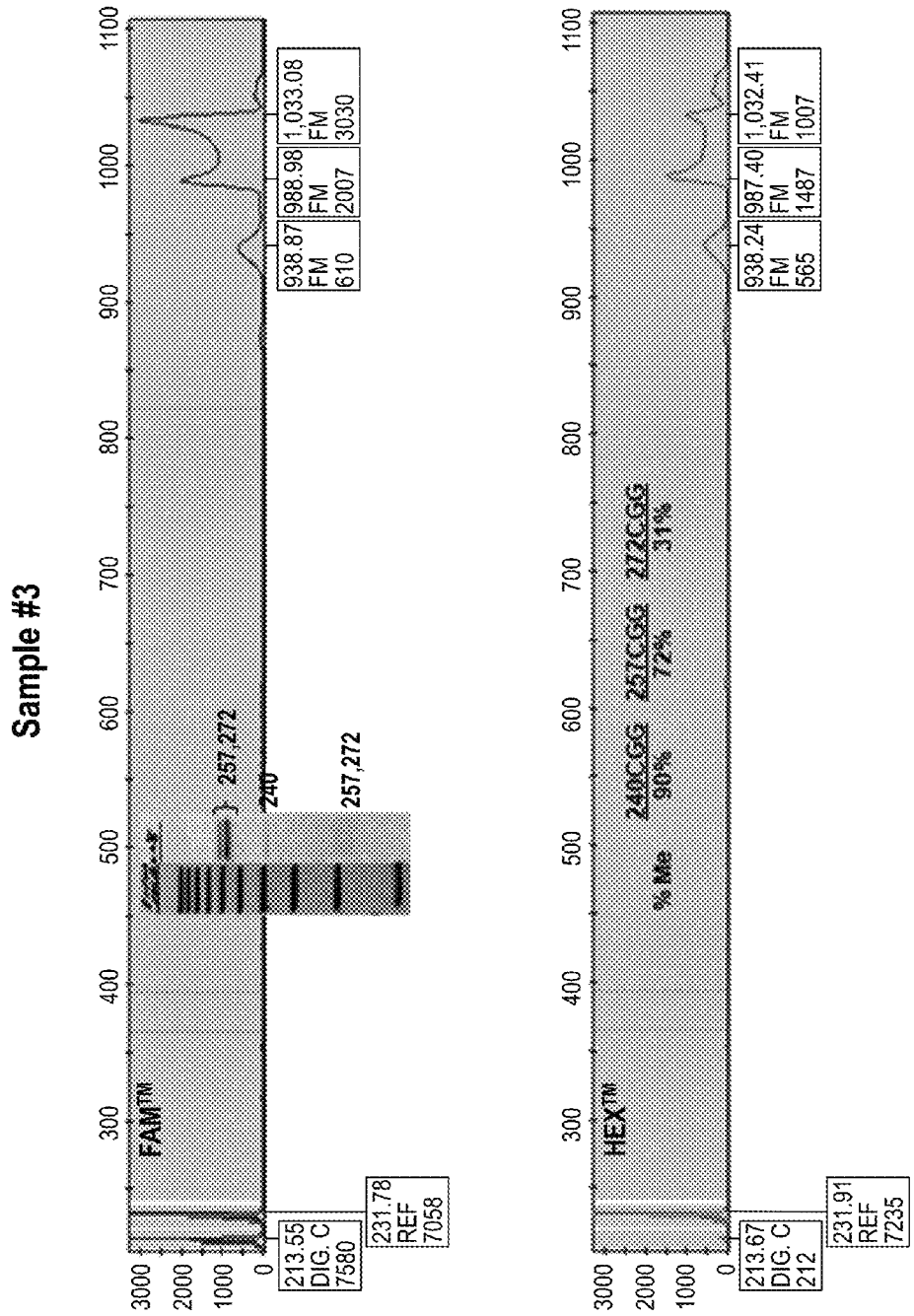
Figure 12D:
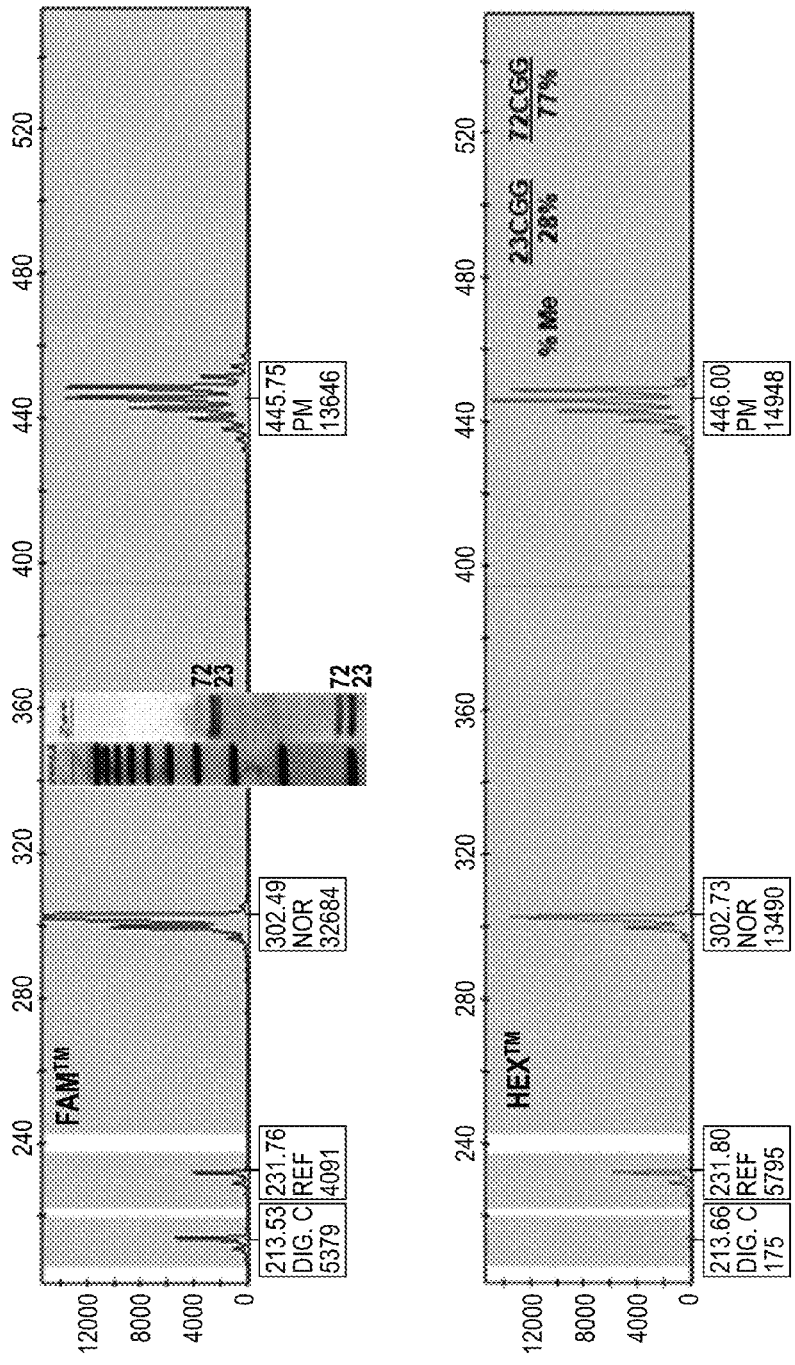
Figure 12E:
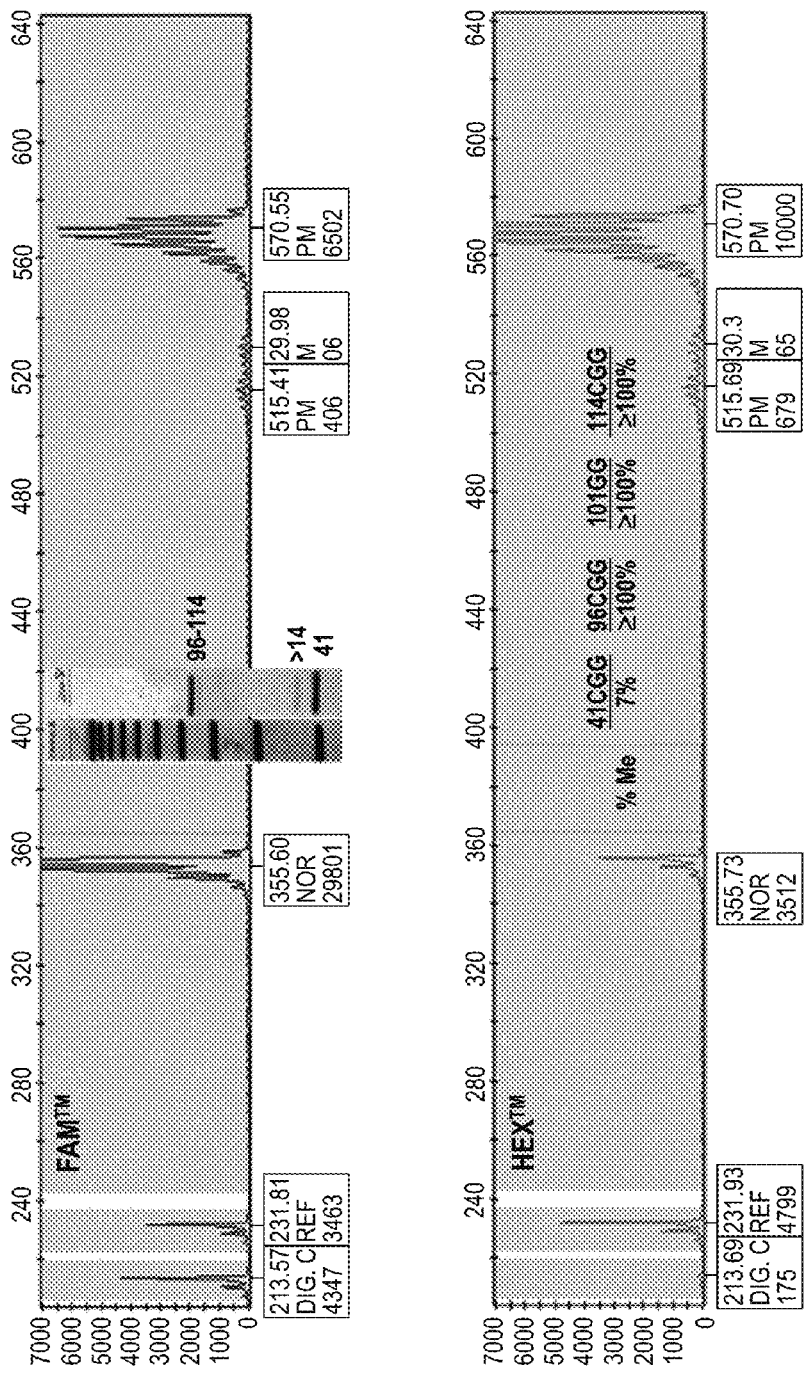
Figure 12F:
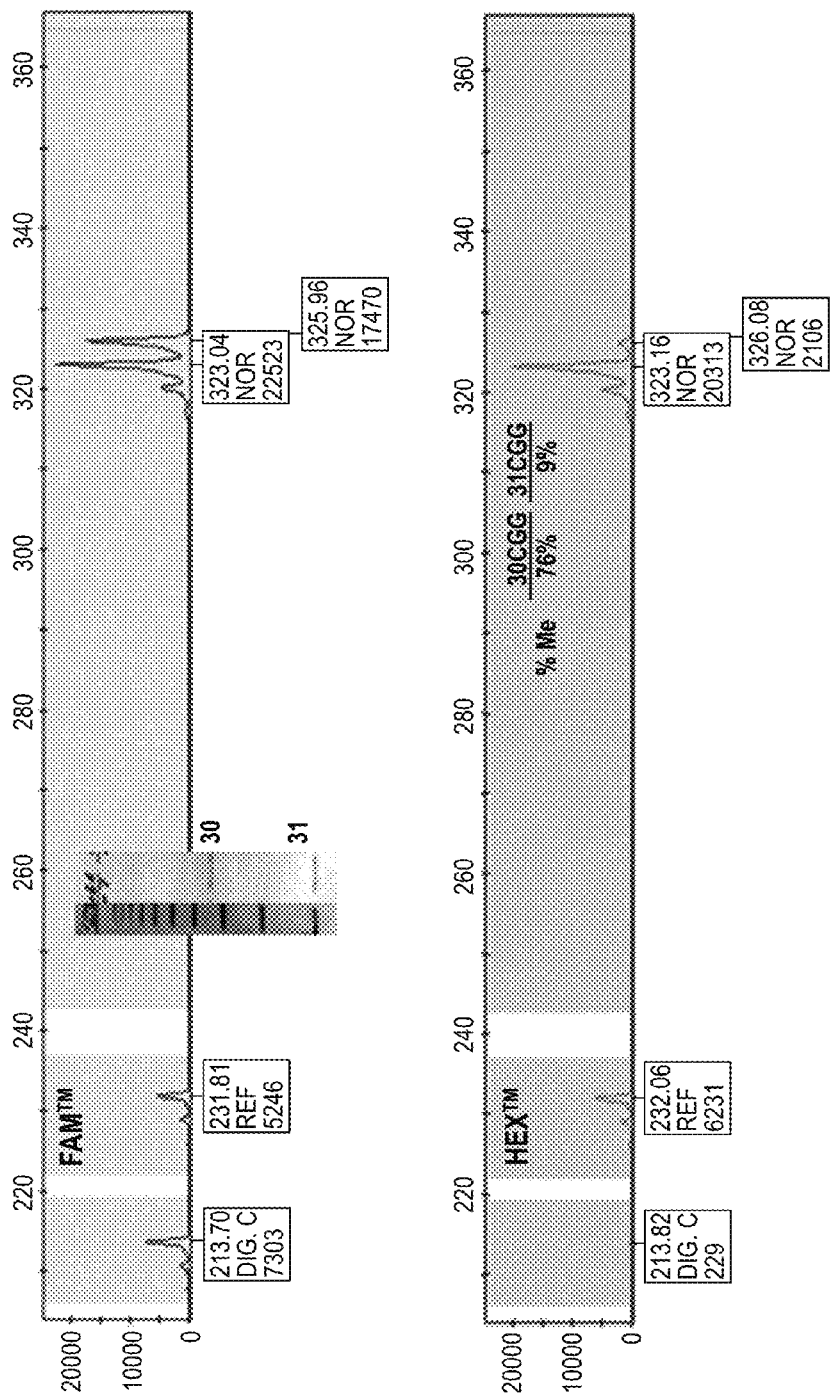
Figure 12G:
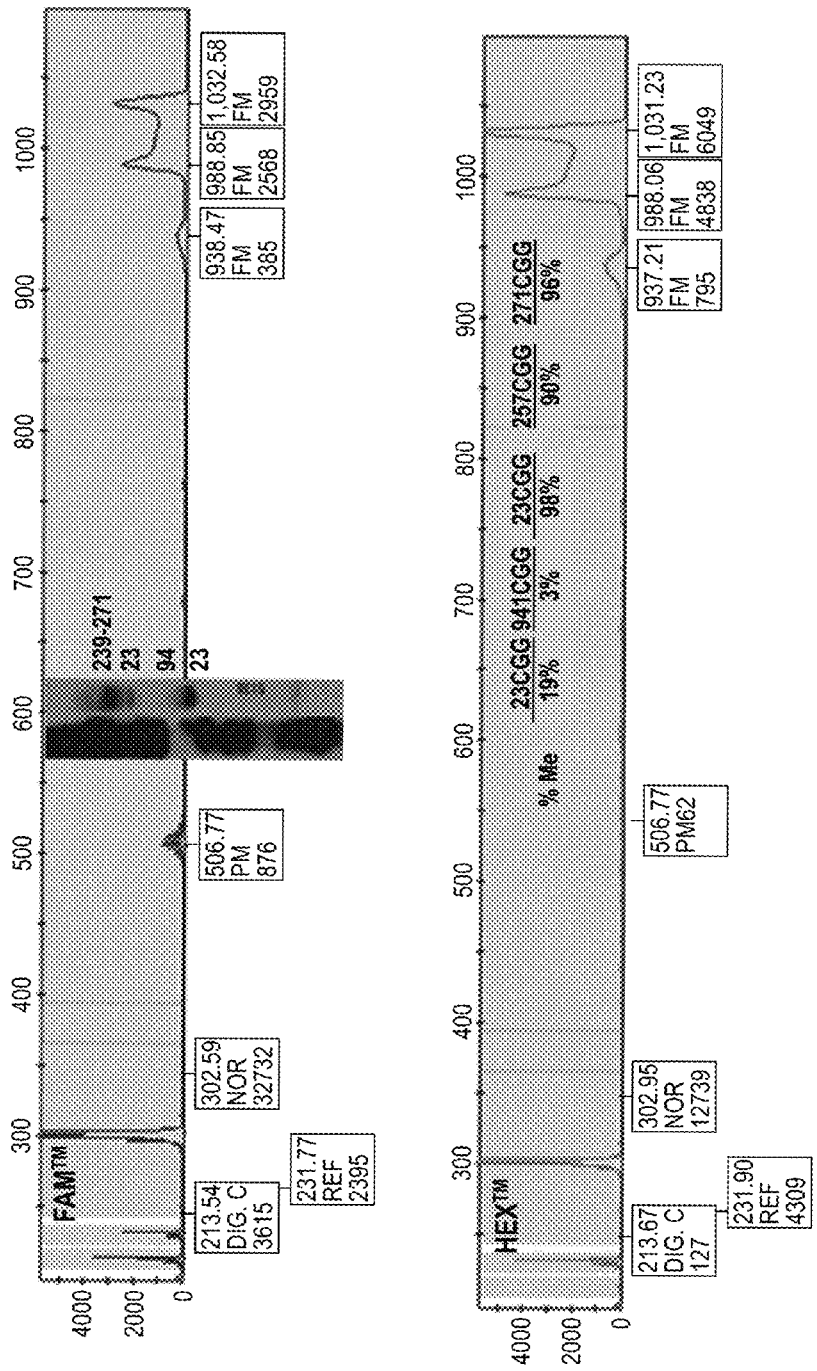

FIGS. 1 and 10 show diagrams outlining exemplary assays according to the methods of the invention.

In certain embodiments, the methods described herein may be used to detect genotypes associated with FXS, Fragile X-associated tremor ataxia syndrome, and Fragile X-associated primary ovarian insufficiency. Genetic loci associated with these conditions are known in the art and include without limitation FMR1, FMR2, the 5' UTR of FMR1, the 5' UTR of FMR2, the CGG repeats within the 5' UTR of FMR1, and the CCG repeats within the 5' UTR of FMR2. As used herein, the term "FMR locus" refers to an FMR1 locus or an FMR2 locus. In an additional embodiment, the methods may be used to detect genotypes associated with GC-rich trinucleotide repeat disorders, such as FXS, Fragile X-associated tremor ataxia syndrome, and Fragile X-associated primary ovarian insufficiency, myotonic dystrophy, Huntington's disease, spinobulbar muscular atrophy, Dentatorubropallidoluysian atrophy, and/or spinocerebellar ataxia. Genetic loci associated with these conditions are known in the art and include without limitation FMR1, FMR2, DMPK, ZNF9, HTT, AR, ATN1, ATXN1-3, ATXN7, ATXN10, CACNA1A, SCA8, PPP2R2B, and TBP. See, e.g., Nat Genet. 1996 May; 13(1):105-8; Nat Genet. 1996 May; 13(1):109-13. Hyperexpansion and/or hypermethylation of the GC-rich regions at these loci are associated with the diseases.

A. GC Reference Standard

In some aspects, the invention relates to a GC reference standard that can be used according to the methods described herein. The GC reference standards of the methods described herein are external reference standards, and are designed to be co-amplified with the FMR loci. In some embodiments, the GC reference standards can be used to assess the number of CGG repeats present in a genetic locus, such as a GC-rich locus present near the FMR1 gene. In exemplary embodiments, the GC reference standard is designed such that it has a desired relative retention time by CE.

As used herein, the term "relative retention time" refers to the amount of time it takes for an product amplified from the GC reference standard to migrate through a capillary in CE, compared to the migration time of other amplified products of a given length and/or GC-richness. In certain embodiments, the relative retention time of a GC reference standard is compared to sequences containing known numbers of CGG repeats. In some instances, the GC reference standard is used to determine the number of CGG repeats in a FMR1 locus from a human subject. In certain embodiments, the relative retention time of a GC reference standard is compared to a genetic locus using the same primers for amplification. In some embodiments, the GC reference standard has a relative retention time in a CE assay such that it does not overlap with a naturally occurring FMR1 allele. For example, in an assay to determine the methylation status and number of CGG repeats in an FMR1 locus, a GC reference standard that has a relative retention time of zero CGG repeats compared to naturally-occurring genomic alleles containing CGG repeats can be included. Another embodiment includes a GC reference standard that has a relative retention time of about 40 CGG repeats. In additional embodiments, the GC reference standard has a relative retention time of less than about 20, about 24 to about 27, or greater than about 32 CGG repeats compared to genomic samples.

Exemplary GC reference standards contain sequences having the formula:

5'-A-B-C-3' wherein A and C represent sequences recognized by forward and reverse PCR primers, and B is a GC-rich sequence. Generally, the GC reference standard has a GC-richness of at least 50, 60, 70, 75, 80, 85, 90, 91, 92, 93, 94, 95, 96, 97, 98, or 99 percent. Sequence A may be chosen from a genomic sequence upstream of a GC-rich or CGG repeat region, and sequence C may be chosen from a genomic sequence downstream of such a region. During the amplification reaction, these sequences or their complements can be used as primer recognition sites, such that the reference standard is amplified using the same primers as the target sequence.

In certain embodiments, sequences A and C are chosen from the FMR1 5'-UTR upstream and downstream of the GC-rich region, respectively. The sequences of A and C, or their complements, may be used as primers for the amplification reaction. Examples of sequence A include: CGG TGG AGG GCC GCC TCT GAG C (SEQ ID NO: 1), CAG GCG CTC AGC TCC GTT TCG GTT T (SEQ ID NO: 2), CAG TCA GGC GCT CAG CTC CGT TTC G (SEQ ID NO: 3), TCC GGT GGA GGG CCG CCT CTG AGC (SEQ ID NO: 4), GGT TCG GCC TCA GTC AGG CGC TCA GCT CCG TTT CG (SEQ ID NO: 5), GGG TTC GGC CTC AGT CAG GCG CTC AGC TCC GTT TCG (SEQ ID NO: 6), GCG GGC CGG GGT TCG GCC TC AGT CA (SEQ ID NO: 7), CAG CGG GCC GGG GGT TCG GCC TCA G (SEQ ID NO: 8), GCA GCG GGC CGG GGG TTC GGC CTC A (SEQ ID NO: 9), GGG CCG GGG GTT CGG CCT CAG TCA G (SEQ ID NO: 10), GGG GTT CGG CCT CAG TCA GGC GCT CA (SEQ ID NO: 11), GGG GTT CGG CCT CAG TCA GGC GCT CAG (SEQ ID NO: 12), GGC GCT CAG CTC CGT TTC GGT TTC ACT TCC (SEQ ID NO: 13), TCA GGC GCT CAG CTC CGT TTC GGT TTC A (SEQ ID NO: 14), CAC TTC CGG TGG AGG GCC GCC TCT GA (SEQ ID NO: 15), TTC CGG TGG AGG GCC GCC TCT GAG C (SEQ ID NO: 16), and GCG CTC AGC TCC GTT TCG GT (SEQ ID NO: 17).

Examples of sequence C include: CAC CTC TCG GGG GCG GGC TCC (SEQ ID NO: 18), ACC TCT CGG GGG CGG GCT CCC (SEQ ID NO: 19), ATG GAG GAG CTG GTG GTG GAA GTG CG (SEQ ID NO: 20), CAC CTC TCG GGG GCG GGC TCC CG (SEQ ID NO: 21), ACC TCT CGG GGG CGG GCT CCC GG (SEQ ID NO: 22), CAC CTC TCG GGG GCG GGC TCC CGG (SEQ ID NO: 23), CAC CTC TCG GGG GCG GGC TCC CGG CG (SEQ ID NO: 24), ACC TCT CGG GGG CGG GCT CCC GGC GC (SEQ ID NO: 25), ACC TCT CGG GGG CGG GCT CCC GGC G (SEQ ID NO: 26), TGG TGG AAG TGC GGG GCT CCA ATG GCG C (SEQ ID NO: 27), TGG AAG TGC GGG GCT CCA ATG GCG C (SEQ ID NO: 28), GGA AGT GCG GGG CTC CAA TGG CGC T (SEQ ID NO: 29), GTG GAA GTG CGG GGC TCC AAT GGC G (SEQ ID NO: 30), TGG TGG TGG AAG TGC GGG GCT CCA A (SEQ ID NO: 31), GAG GAG CTG GTG GTG GAA GTG CGG GGC T (SEQ ID NO: 32), AGG AGC TGG TGG TGG AAG TGC GGG GCT C (SEQ ID NO: 33), CTG GTG GTG GAA GTG CGG GGC TCC AAT G (SEQ ID NO: 34), AGA TGG AGG AGC TGG TGG TGG AAG TGC GGG (SEQ ID NO: 35), GGA AGT GCG GGG CTC CAA TGG CGC TTT CTA (SEQ ID NO: 36), GGA AGT GCG GGG CTC CAA TGG CGC TT (SEQ ID NO: 37), TGG AGG AGC TGG TGG TGG AAG TGC G (SEQ ID NO: 38), and AGT GCG GGG CTC CAA TGG CG (SEQ ID NO: 39).

SEQ ID NOs 40 and 41 show the FMR1 sequences upstream and downstream of the CGG repeat region. In certain embodiments, sequence A comprises at least 10 nucleotides from SEQ ID NO: 40, and sequence C comprises at least 10 nucleotides from SEQ ID NO: 41.

Sequence B is a GC-rich sequence, and may have a length such that the reference standard has a particular relative retention time in a CE analysis. The retention time can be measured in relation to known standards with defined lengths and GC character. For example, the length of sequence B may be chosen so the reference standard has a relative retention time of less than about 20, about 24 to about 27, or greater than about 32 CGG repeats compared to genomic samples. The length of sequence B may be chosen so the reference standard has a relative retention time of less than or about zero CGG. In certain examples, the reference standard has a relative retention time of about −100, −90, −80, −70, −60, −50, −40, −30, −20, −10 or zero CGG repeats. In some embodiments, the GC reference standard has a relative retention time of less than or equal to 3, 2, 1, zero, −1, −2, −3, −4, −5, −10, −15, or −20 CGG repeats. The relative retention time of the reference standard can be chosen such that it does not overlap with either the primer peak or a naturally occurring FMR1 allele. The relative retention time of the GC reference standard can also be chosen such that it does not overlap with the digestion control (discussed below), when one is used.

The GC reference standard can have a negative relative retention time, for example, when the reference standard has less flanking sequence surrounding the GC-rich region than the products amplified from a genomic sample. Thus, a GC reference standard may actually contain a positive number of CGG repeats but have a retention time equivalent to a hypothetical genomic sample with a negative number of CGG repeats due to a difference in flanking sequence content.

In some embodiments, the length of B is from X−300 to X+10 nucleotides in length, where X is the sum of:
a) the number of nucleotides between the 3'-end of sequence A and the beginning of the GC-rich region; and
b) the number of nucleotides between the end of the GC-rich region and the 5' end of sequence C.

In some embodiments, B comprises or consists of the sequence CGGCGGCGGaGGCGGCGGCGGCGGCG-GCGGCGGCGGCGGtGGaGGCGGCGGC GGCGGCG-GCGGCGGCGGCGGCGGCGGCGGaGGCGGCGGCG-GCGGCGGCGGC GGCGGCGGCGGCGGCGGaGGCGGCGGCGG (SEQ ID NO: 48). In some embodiments, B comprises at least 50, 75, 100, or 125 nucleotides of SEQ ID NO: 48. In some embodiments, B comprises or consists of the sequence CGGCGGCGGaGGCGGCGGCGGCGGCGGCGGCG-GCGGCGGCGGaGGCGGCGG CGGCGGCGGCGGCG-GCGGCGGCGGCGGCGGaGGCGGCGGCGGCGGCG-GCGG CGGCGGCGGCGGCGGCGGaGGCGGCGGCGG (SEQ ID NO: 49). In some embodiments, B comprises at least 50, 75, 100, or 125 nucleotides of SEQ ID NO: 49. In some embodiments, B comprises or consists of a sequence that hybridizes under stringent conditions with SEQ ID NO:48 or SEQ ID NO: 49.

An example of stringent hybridization conditions is hybridization at 42° C. in a solution comprising 50% formamide, 5×SSC (where 1×SSC is 150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing at 65° C. in a solution comprising 0.1×SSC.

Figure 2:
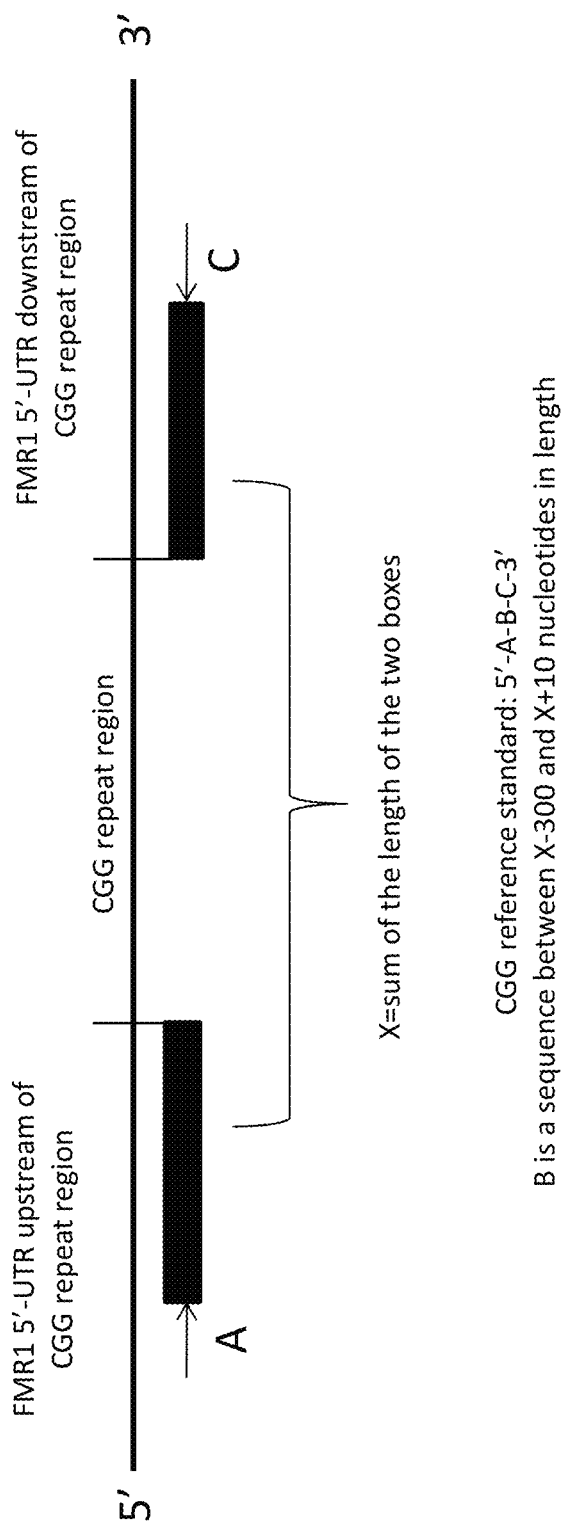
FIG. 2 shows an example of a GC reference standard designed to migrate at a relative retention time that does not overlap with a naturally-occurring FMR1 GC-rich locus.

FIG. 2 shows an example of a GC reference standard that has a relative retention time that does not overlap with naturally-occurring sequences from an FMR1 GC-rich locus.

In certain embodiments, the GC reference standard is contained within a plasmid or other vector. The plasmid or other vector may be linearized, for example by digestion with a restriction enzyme, or left intact. In one embodiment, the plasmid is pBR322. When the GC reference standard is added to a sample or a portion of a sample as part of a larger DNA molecule, such as a plasmid, the amplification reaction does not necessarily amplify all parts of the larger DNA molecule (e.g., sequences that may not be amplified can include a plasmid origin of replication, antibiotic resistance marker, intervening noncoding sequences, etc.), and for purposes of this disclosure, such non-amplified sequences in a molecule comprising the GC reference standard are not considered in determining the relative retention time or GC-richness of the GC reference standard.

The GC reference standard can be added to a nucleic acid sample before or after treatment with the methylation-sensitive DNase. Adding the GC reference before treatment with the methylation-sensitive DNase can reduce errors that may otherwise result from pipetting the GC reference standard into two portions of the sample, one of which was treated with the methylation-sensitive DNase and one of which was not. That is, when the GC reference is added to the sample before treatment with the methylation-sensitive DNase, it may be added to the sample before dividing the sample into two portions. In embodiments in which the GC reference standard is added to the sample before the methylation-sensitive DNase or control enzyme, the GC reference standard is not cleaved by the DNase, e.g., it may be devoid of recognition sites for the DNase and/or it may be methylated such that it is resistant to cleavage by the methylation-sensitive DNase. When the GC reference standard is added to the sample after treatment of a portion of the sample with the methylation-sensitive DNase, the GC reference standard is added to the first and second portions of the sample. The amount of GC reference standard added to the sample can vary depending on the type of amplification reaction and the extent of amplification (e.g., the number of cycles or the length of isothermal incubation). For example, in some embodiments using PCR as the amplification reaction, about 750 to about 12,000 copies of the GC reference standard can be added for each PCR reaction.

B. Digestion Control

The methods described herein may include the use of a digestion control. The digestion control is designed to be co-amplified with a region in the sample DNA, such as an FMR locus. The digestion control is unmethylated and contains at least one recognition site for the methylation-sensitive DNase, and thus is cleaved upon treatment with the methylation-sensitive DNase. As a result, this control template reports the effectiveness of the digestion by the methylation-sensitive restriction endonuclease.

In some embodiments, the digestion control has a structure and length such that it has a particular relative retention time in a CE analysis. In embodiments in which the amplification reaction comprises PCR, the same primers may be used to amplify the genomic target locus and the digestion control. Fragments of the digestion control resulting from digestion by the methylation-sensitive DNase do not support amplification of the digestion control. In some embodiments, the digestion control has a relative retention time of less than about 20, about 24 to about 27, or greater than about 32 CGG repeats compared to genomic samples. In certain examples, the digestion control has a relative retention time of about −100, −90, −80, −70, −60, −50, −40, −30, −20, −10 or zero CGG repeats. In some embodiments, the digestion control has a relative retention time of less than or equal to 3, 2, 1, zero, −1, −2, −3, −4, −5, −10, −15, or −20 CGG repeats. The relative retention time of the digestion control can be chosen such that it does not overlap with either the primer peak or a naturally occurring FMR1 allele. The relative retention time of the digestion control can also be chosen such that it does not overlap with the GC reference standard.

In certain embodiments, the digestion control is contained within a plasmid or other vector. The plasmid or other vector may be linearized, for example by digestion with a restriction enzyme, or left intact. In one embodiment, the plasmid is pBR322. When the digestion control is added to a sample or a portion of a sample as part of a larger DNA molecule, such as a plasmid, the amplification reaction does not necessarily amplify all parts of the larger DNA molecule (e.g., sequences that may not be amplified can include a plasmid origin of replication, antibiotic resistance marker, intervening noncoding sequences, etc.), and for purposes of this disclosure, such non-amplified sequences in a molecule comprising digestion control are not considered in determining the relative retention time or GC-richness of the digestion control.

In some embodiments, the digestion control comprises or consists of the sequence TCAGGCGCTCAGCTC-CGTTTCGGTTTCACGGTGACGGAGGCGC <u>CGCTGCCCGGGGGCGTGCGGCAGCGCGGCGGCG</u> GCGGCGGCGGCGGCGGCGGCGGCGGCGGC GGCG-GCGGCGGCGGCGGCGGCGGCGGCGGCGGCG-GCGGCGGCGGCGGC GGCGGCGGCGGC TGGGCCTCGAGCGCCCGCAGCCCAGGAAGTGGA AGTGCGGG <u>GCTCCAATGGCGCT</u> (SEQ ID NO: 50). The underlined portions are examples of the flanking sequences which can be adjusted to modify the size of the resulting amplicon. In some embodiments, the digestion control comprises or consists of at least 100, 150, 175, 200, or 220 nucleotides of SEQ ID NO: 50. In some embodiments, the digestion control comprises or consists of a sequence that hybridizes under stringent conditions to SEQ ID NO: 50. In some embodiments, the digestion control comprises or consists of a sequence that is a version of SEQ ID NO: 50 modified in that it has a larger or smaller number of CGG repeats, such that the digestion control has a relative retention time as discussed above.

In some embodiments, the relative retention times of the digestion control and the reference standard differ by the equivalent of 1, 2, 3, 4, 5, 6, 7, 8, 9, 10, or more CGG repeats. Template or primer slipping may occur in GC-rich amplification reactions, resulting in products that differ in length by about 1-3 CGG repeats from the original target. Thus, in particular embodiments, the relative retention times of the digestion control and the reference standard differ by the equivalent of 4 or more CGG repeats to minimize signal overlap. In some embodiments, both the digestion control and the reference standard have a relative retention time of less than or equal to 3, 2, 1, zero, −1, −2, −3, −4, −5, −10, or −15 CGG repeats. In some embodiments, the digestion control has the general primary structure described in section I.A above for some embodiments of the GC reference standard, including A, B, and C sequences as described above. When both of the digestion control and GC reference standard comprise A, B, and C sequences as described above, at least one of the A, B, or C segments in the digestion control may differ in length from its counterpart in the GC reference standard, such that the digestion control is of a length that differs by the equivalent of at least 1, 2, 3, 4, 5, or more CGG repeats from the length of the reference standard. The digestion control will still have an appropriate methylation status for digestion by the methylation-sensitive nuclease (which status may be the opposite of the methylation status of the reference standard).

The amount of digestion control added to the sample can vary depending on the type of amplification reaction and the extent of amplification (e.g., the number of cycles or the length of isothermal incubation). For example, in some embodiments using PCR as the amplification reaction, about 750 to about 12,000 copies of the digestion control can be added for each PCR reaction.

C. Methylation-Sensitive Nuclease

The methods described herein may include the use of a methylation-sensitive nuclease. In some instances, the nuclease is a DNase such as a restriction enzyme. The methylation-sensitive nuclease of the methods provided herein differentially cleaves the portion of the FMR locus that is amplified based on its methylation state. A control nuclease does not cleave that portion.

Methylation-sensitive DNases include AatII, Acc65I, AccI, AciI, AclI, AfeI, AgeI, AEI-HF™, AhdI, AleI, ApaI, ApaLI, AscI, AsiSI, AvaI, AvaII, BaeI, BanI, BbvCI, BceAI, BcgI, BfuAI, BfuCI, BglI, BmgBI, BsaAI, BsaBI, BsaHI, BsaI, BSAI-HF®, BseYI, BsiEI, BsiWI, BslI, BsmAI, BsmBI, BsmFI, BspDI, BspEI, BsrBI, BsrFI, BssHII, BssKI, BstAPI, BstBI, BstUI, BstZ17I, BtgZI, Cac8I, ClaI, DraIII, DrdI, EaeI, EagI, EAGI-HF™, EarI, EciI, EcoRI, ECORI-HF™, EcoRV, ECORV-HF®, FauI, Fnu4HI, FokI, FseI, FspI, HaeII, HgaI, HhaI, HincII, HinfI, HinP1I, HpaI, HpaII, Hpy166II, Hpy188III, Hpy99I, HpyAV, HpyCH4IV, KasI, MboI, MluI, MmeI, MspA1I, MwoI, NaeI, NarI, NciI, NgoMIV, NheI, NHEI-HF™, NlaIV, NotI, NOTI-HF™, NruI, Nt.BbvCI, Nt.BsmAI, Nt.CviPII, PaeR7I, PhoI, PleI, PmeI, PmlI, PshAI, PspOMI, PspXI, PvuI, RsaI, RsrII, SacII, SalI, SALI-HF™, Sau3AI, Sau96I, ScrFI, SfaNI, SfiI, SfoI, SgrAI, SmaI, SnaBI, StyD4I, TfiI, TliI, TseI, TspMI, XhoI, XmaI, or ZraI (New England Biolabs; Nature Protocols 1: 1621-1636 (2006)).

In certain embodiments, the methylation-sensitive DNase is chosen from HpaI, NruI, EagI, BssHII, and HhaI. In certain embodiments, the methylation-sensitive DNase is HpaII.

Recognition sites for selected methylation-sensitive DNases are shown below:

| Enzyme | Sequence | Methylation Sensitivity |
|---|---|---|
| AatII | GACGT/C | Cleavage blocked |
| Acc65I | G/GTACC | Cleavage blocked |
| AccI | GT/MKAC | Cleavage blocked |
| AciI | CCGC(-3/-1) | Cleavage blocked |
| AclI | AA/CGTT | Cleavage blocked |
| AfeI | AGC/GCT | Cleavage blocked |
| AgeI | A/CCGGT | Cleavage blocked |
| AeI-HF™ | A/CCGGT | Cleavage blocked |
| AhdI | GACNNN/NNGTC (SEQ ID NO: 51) | Cleavage impaired |
| AleI | CACNN/NNGTG (SEQ ID NO: 52) | Cleavage impaired |
| ApaI | GGGCC/C | Cleavage blocked |
| ApaLI | GGGCC/C | Cleavage blocked |
| AscI | GG/CGCGCC | Cleavage blocked |
| AsiSI | GCGAT/CGC | Cleavage blocked |
| AvaI | C/YCGRG | Cleavage blocked |
| AvaII | G/GWCC | Cleavage blocked |
| BaeI | (10/15)ACNNNNGTAYC(12/7) (SEQ ID NO: 53) | Cleavage blocked |
| BanI | G/GYRCC | Cleavage blocked |
| BbvCI | CCTCAGC(-5/-2) | Cleavage impaired |
| BceAI | ACGGC(12/14) | Cleavage blocked |
| BcgI | (10/12)CGANNNNNNTGC(12/10) (SEQ ID NO: 54) | Cleavage blocked |
| BfuAI | ACCTGC(4/8) | Cleavage impaired |
| BfuCI | /GATC | Cleavage blocked |
| BglI | GCCNNNN/NGGC (SEQ ID NO: 55) | Cleavage blocked |
| BmgBI | CACGTC(-3/-3) | Cleavage blocked |
| BsaAI | YAC/GTR | Cleavage blocked |
| BsaBI | GATNN/NNATC (SEQ ID NO: 56) | Cleavage blocked |
| BsaHI | GR/CGYC | Cleavage blocked |
| BsaI | GGTCTC(1/5) | Cleavage blocked |
| BSAI-HF® | GGTCTC(1/5) | Cleavage blocked |
| BseYI | CCCAGC(-5/-1) | Cleavage blocked |
| BsiEI | CGRY/CG | Cleavage blocked |
| BsiWI | C/GTACG | Cleavage blocked |
| BslI | CCNNNNN/NNGG (SEQ ID NO: 57) | Cleavage blocked |
| BsmAI | GTCTC(1/5) | Cleavage blocked |
| BsmBI | CGTCTC(1/5) | Cleavage blocked |
| BsmFI | GGGAC(10/14) | Cleavage blocked |
| BspDI | AT/CGAT | Cleavage blocked |
| BspEI | T/CCGGA | Cleavage impaired |
| BsrBI | CCGCTC(-3/-3) | Cleavage blocked |
| BsrFI | R/CCGGY | Cleavage blocked |
| BssHlI | G/CGCGC | Cleavage blocked |
| BssKI | /CCNGG | Cleavage blocked |
| BstAPI | GCANNNN/NTGC (SEQ ID NO: 58) | Cleavage blocked |
| BstBI | TT/CGAA | Cleavage blocked |
| BstUI | CG/CG | Cleavage blocked |
| BstZ17I | GTA/TAC | Cleavage blocked |
| BtgZI | GCGATG(10/14) | Cleavage impaired |
| Cac8I | GCN/NGC | Cleavage blocked |
| ClaI | AT/CGAT | Cleavage blocked |

-continued

| Enzyme | Sequence | Methylation Sensitivity |
|---|---|---|
| DraIII | CACNNN/GTG | Cleavage impaired |
| DrdI | GACNNNN/NNGTC (SEQ ID NO: 59) | Cleavage blocked |
| EaeI | Y/GGCCR | Cleavage blocked |
| EagI | C/GGCCG | Cleavage blocked |
| Eagl-HF ™ | C/GGCCG | Cleavage blocked |
| EarI | CTCTTC(1/4) | Cleavage impaired |
| EciI | GGCGGA(11/9) | Cleavage blocked |
| EcoRI | G/AATTC | Cleavage blocked |
| EcoRl-HF ™ | G/AATTC | Cleavage blocked |
| EcoRV | GAT/ATC | Cleavage impaired |
| EcoRV-HF ® | GAT/ATC | Cleavage impaired |
| FauI | CCCGC(4/6) | Cleavage blocked |
| Fnu4HI | GC/NGC | Cleavage blocked |
| FokI | GGATG(9/13) | Cleavage impaired |
| FseI | GGCCGG/CC | Cleavage blocked |
| FspI | TGC/GCA | Cleavage blocked |
| HaeII | RGCGC/Y | Cleavage blocked |
| HgaI | GACGC(5/10) | Cleavage blocked |
| HhaI | GCG/C | Cleavage blocked |
| HincII | GTY/RAC | Cleavage blocked |
| HinfI | G/ANTC | Cleavage blocked |
| HinP1I | G/CGC | Cleavage blocked |
| HpaI | GTT/AAC | Cleavage blocked |
| HpaII | C/CGG | Cleavage blocked |
| Hpy166II | GTN/NAC | Cleavage blocked |
| Hpy188III | TC/NNGA | Cleavage blocked |
| Hpy99I | CGWCG/ | Cleavage blocked |
| HpyAV | CCTTC(6/5) | Cleavage impaired |
| HpyCH4IV | A/CGT | Cleavage blocked |
| KasI | G/GCGCC | Cleavage blocked |
| MboI | /GATC | Cleavage impaired |
| MluI | A/CGCGT | Cleavage blocked |
| MmeI | TCCRAC(20/18) | Cleavage blocked |
| MspA1I | CMG/CKG | Cleavage blocked |
| MwoI | GCNNNNN/NNGC (SEQ ID NO: 60) | Cleavage blocked |
| NaeI | GCC/GGC | Cleavage blocked |
| NarI | GG/CGCC | Cleavage blocked |

-continued

| Enzyme | Sequence | Methylation Sensitivity |
|---|---|---|
| NciI | CC/SGG | Cleavage impaired |
| NgoMIV | G/CCGGC | Cleavage blocked |
| NheI | G/CTAGC | Cleavage blocked |
| NHEI-HF ™ | G/CTAGC | Cleavage blocked |
| NlaIV | GGN/NCC | Cleavage blocked |
| NotI | GC/GGCCGC | Cleavage blocked |
| NOTI-HF ™ | GC/GGCCGC | Cleavage blocked |
| NruI | TCG/CGA | Cleavage blocked |
| Nt.BbvCI | CCTCAGC(-5/-7) | Cleavage blocked |
| Nt.BsmAI | GTCTC(1/-5) | Cleavage blocked |
| Nt.CviPII | (0/-1)CCD | Cleavage blocked |
| PaeR7I | C/TCGAG | Cleavage blocked |
| PhoI | GG/CC | Cleavage impaired |
| PleI | GAGTC(4/5) | Cleavage blocked |
| PmeI | GTTT/AAAC | Cleavage blocked |
| PmlI | CAC/GTG | Cleavage blocked |
| PshAI | GACNN/NNGTC (SEQ ID NO: 61) | Cleavage blocked |
| PspOMI | G/GGCCC | Cleavage blocked |
| PspXI | VC/TCGAGB | Cleavage impaired |
| PvuI | CGAT/CG | Cleavage blocked |
| RsaI | GT/AC | Cleavage blocked |
| RsrII | CG/GWCCG | Cleavage blocked |
| SacII | CCGC/GG | Cleavage blocked |
| SalI | G/TCGAC | Cleavage blocked |
| SALI-HF ™ | G/TCGAC | Cleavage blocked |
| Sau3AI | /GATC | Cleavage blocked |
| Sau96I | G/GNCC | Cleavage blocked |
| ScrFI | CC/NGG | Cleavage blocked |
| SfaNI | GCATC(5/9) | Cleavage impaired |
| SfiI | GGCCNNNN/NGGCC (SEQ ID NO: 62) | Cleavage blocked |
| SfoI | GGC/GCC | Cleavage blocked |
| SgrAI | CR/CCGGYG | Cleavage blocked |
| SmaI | CCC/GGG | Cleavage blocked |
| SnaBI | TAC/GTA | Cleavage blocked |
| StyD4I | /CCNGG | Cleavage impaired |
| TfiI | G/AWTC | Cleavage blocked |
| TliI | C/TCGAG | Cleavage impaired |

| Enzyme | Sequence | Methylation Sensitivity |
|---|---|---|
| TseI | G/CWGC | Cleavage blocked |
| TspMI | C/CCGGG | Cleavage blocked |
| XhoI | C/TCGAG | Cleavage impaired |
| XmaI | C/CCGGG | Cleavage impaired |
| ZraI | GAC/GTC | Cleavage blocked |

In certain embodiments, a first portion of a sample is treated with a methylation-sensitive nuclease, while a second portion is treated with a control nuclease. The control nuclease may be a restriction enzyme that does not cleave the amplified locus. The control nuclease may be a non-methylation-sensitive nuclease. Many restriction enzymes and their specificities are well known in the art. Examples of control nucleases that can be used in the described methods include HINDIII-HF™, DpnI, NaeI, EcoRI, or Sau3A1, among others. Control nucleases are discussed in more detail above in the initial portion of section I.

D. Amplification Methods

The methods of the invention also include nucleic acid amplification. Many methods exist for amplifying nucleic acid sequences including reverse transcription, polymerase chain reaction (PCR), real-time PCR (RT-PCR), nucleic acid sequence-base amplification (NASBA), ligase chain reaction, multiplex ligatable probe amplification, invader technology (Third Wave), rolling circle amplification, in vitro transcription, strand displacement amplification, transcription-mediated amplification (TMA), RNA (Eberwine) amplification, loop-mediated isothermal amplification, and other methods that are known to persons skilled in the art. In some embodiments, the methods further comprise processing concatenated amplification products generated by an amplification reaction such as rolling circle amplification or loop-mediated isothermal amplification, e.g., by endonucleolytic cleavage of a recognition site present in the amplification template or incorporated primer, in order to provide non-concatenated amplification products for downstream analysis.

A typical PCR reaction includes multiple amplification steps, or cycles that selectively amplify target nucleic acid species. A typical PCR reaction includes three steps: a denaturing step in which a target nucleic acid is denatures; an annealing step in which a set of PCR primers (forward and reverse primers) anneal to complementary DNA strands; and an elongation step in which a thermostable DNA polymerase elongates the primers. By repeating these steps multiple times, a DNA fragment is amplified to produce an amplicon, corresponding to the target DNA sequence. Typical PCR reactions include 20 or more cycles of denaturation, annealing, and elongation. In many cases, the annealing and elongation steps can be performed concurrently, in which case the cycle contains only two steps.

In certain methods, a set of primers is used for each target sequence. In some embodiments, a single set of primers can amplify both the GC reference standard and the target nucleic acid. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than 15, 20, 25, 30 or 35 nucleotides in length. In additional embodiments, a primer is greater than 35 nucleotides in length. In some embodiments, the set of primers includes one primer that hybridizes to SEQ ID NO: 40, and a second that hybridizes to SEQ ID NO: 41. A primer may include at least 10 contiguous nucleotides depicted in SEQ ID NO: 40, or a primer may includes at least 10 contiguous nucleotides complementary to the depicted strand of SEQ ID NO: 41.

In certain embodiments, the methods include PCR reactions capable of amplifying at least 100, 150, 200, 300, 400, 500, 600, 700, 800, 900, 1000, 2000 or more CGG repeats. Exemplary methods capable of amplifying large GC-rich templates are described, for example, in US Publication No. 2010/0209970, which is incorporated herein by reference in its entirety.

The PCR reactions may include providing dNTPs in a GC/AT ratio greater than one and at a total dNTP concentration conducive to synthesis of DNA using GC-rich templates. The GC/AT ratio may be about 1.1, 1.2, 1.4, 1.6, 2, 2.5, 3, 4, 5, 6, 7, 8, 9, 10, 11, 12, 13, 14, 15, 16, 17, 18, 19, 20, 25, or higher. The GC/AT ratio may be between 1.1 and 20, 1.1 and 15, 1.1 and 10, 1.1 and 8, 1.1 and 7, 1.1 and 6, 1.1 and 5, 1.2 and 25, 1.4 and 25, 1.6 and 25, 2 and 25, 3 and 25, 4 and 25, 5 and 25, 2 and 15, 2.5 and 10, or 4 and 10. The total dNTP concentration may be about 0.4, 0.5, 0.6, 0.7, 0.8, 0.9, 1, 1.2, 1.5, 2, or 3 mM. The dNTP concentration may be between 0.4 and 3 mM, 0.5 and 3 mM, 0.6 and 3 mM, 0.7 and 3 mM, 0.8 and 3 mM, 0.9 and 3 mM, 1 and 3 mM, 0.4 and 2 mM, 0.4 and 1.5 mM, 0.4 and 1.2 mM, 0.4 and 1 mM, 0.4 and 0.9 mM, 0.4 and 0.8 mM, 0.4 and 0.7 mM, 0.5 and 2 mM, 0.5 and 1 mM, or 0.6 and 0.9 mM.

The DNA polymerase used in a PCR reaction may comprise a wild-type, modified, thermophilic, chimeric, engineered, and/or a mixture of more than one polymerase. The DNA polymerase may comprise a high-fidelity DNA polymerase (EXACT POLYMERASE™ (5 PRIME GmbH), ACCUSURE™ DNA Polymerase (Bioline), PHUSION™ ACCUPRIME™ Pfx (Invitrogen), Extensor Hi-Fidelity PCR Enzyme (ABgene), ACCUZYME™ DNA Polymerase (Bioline), OPTIMASE® DNA Polymerase (Transgenomic, Inc.), VELOCITY DNA Polymerase (Bioline), GENECHOICE® ACCUPOL™ DNA Polymerase (GeneChoice, Inc.), KOD HIFI™ DNA Polymerase (Novagen), EASY-A™ High-Fidelity PCR Cloning Enzyme (Stratagene), EXL™ DNA Polymerase (Stratagene), KAPA HIFI™ DNA Polymerase (Kapa Biosystems), HERCULASE® II Fusion DNA Polymerase (Stratagene), BIO-X-ACT™ Long DNA Polymerase (Bioline), BIO-X-ACT™ Short DNA Polymerase (Bioline), EU-Taq DNA Polymerase (EENZYME® LLC), PYROPHAGE® 3173 DNA Polymerase, Pwo DNA Polymerase (Roche Applied Science), or PLATINUM® Taq DNA Polymerase High Fidelity (Invitrogen)), a hot-start DNA polymerase (PHIRE™ Hot Start DNA Polymerase (New England Biolabs), PHUSION™ Hot Start High-Fidelity DNA Polymerase (New England Biolabs), JUMPSTART™ REDTAQ™ DNA Polymerase (Sigma-Aldrich), PFUULTRA™ Hotstart DNA Polymerase (Stratagene), PFUTURBO® Cx Hotstart DNA Polymerase (Stratagene), PRIMESTAR™ HS DNA Polymerase (Takara), HotMaster™ Taq DNA Polymerase (5 PRIME GmbH), HOTTAQ™ DNA Polymerase (Abnova Corporation), AMPLITAQ GOLD® DNA Polymerase (Applied Biosystems), RED HOT® DNA Polymerase (ABgene), ACCUPRIME™ GC-Rich DNA Polymerase (Invitrogen), PAQ5000™ DNA Polymerase (Stratagene), or SAHARA™ DNA Polymerase (Bioline)), a mixture of more than one polymerase (GENECHOICE® UNIPOL™ DNA Polymerase (GeneChoice, Inc.), KOD XL™ DNA Polymerase (Novagen), LA TAQ DNA Polymerase (Takara), EXPAND® 20 kb PLUS Thermostable DNA polymerase mixture (Roche Applied Science), EXPAND® High Fidelity PLUS Thermostable DNA polymerase mixture (Roche Applied Science), EXPAND® High Fidelity Thermostable DNA polymerase mixture (Roche Applied Science), EXPAND® Long Template Thermostable DNA polymerase mixture (Roche Applied Science), HERCULASE® Enhanced DNA Polymerase (Stratagene), KAPA LONGRANGE™ DNA Polymerase (Kapa Biosystems), Synergy Taq DNA Polymerase (EENZYME® LLC), or ELONGASE® Enzyme Mix (Invitrogen)), a chimeric DNA polymerase (PFX50™ DNA Polymerase (Invitrogen), BIOLINE HYBRIPOL™ DNA Polymerase (Bioline), or PHUSION™ DNA Polymerase (New England Biolabs)), a modified DNA polymerase (KAPA2G™ Robust DNA Polymerase (Kapa Biosystems), KAPA2G™ Robust HotStart DNA Polymerase (Kapa Biosystems), KAPA2G™ Fast DNA Polymerase (Kapa Biosystems), KAPA2G™ Fast HotStart DNA Polymerase (Kapa Biosystems), 9 DEGREES NORTH™ (Modified) DNA Polymerase (New England Biolabs), or THERMINATOR™ DNA Polymerase (New England Biolabs)), an exo-DNA polymerase (Exo-Pfu DNA Polymerase (Stratagene), Bst DNA Polymerase Lg Frag (New England Biolabs), MASTERAMP™ Tfl DNA Polymerase (EPICENTRE Biotechnologies), Thermoprime Plus DNA Polymerase (ABgene), Taq-red DNA Polymerase (AppliChem GmbH), BIOTHERM™ Taq DNA Polymerase (EENZYME® LLC), GENECHOICE® REDPOL™ DNA Polymerase (GeneChoice, Inc.), or Exo Minus (Lucigen)), a high-yield DNA polymerase (YIELDACE™ DNA Polymerase (Stratagene) or E2TAK™ DNA Polymerase (Takara)), or naturally occurring DNA polymerases from *P. kodakaraensis, P. furiosus, T. gorgonarius, T. zilligii, T. litoralis* "Vent™", P. GB-D "Deep Vent", T. 9N-7, *T. aggregans, T. barossii, T. fumicolans, T. celer, Pyrococcus* sp. strain ST700, *T. pacificus, P. abysii, T. profundus, T. siculi, T. hydrothermalis, Thermococcus* sp. strain GE8, *T. thioreducens, P. horikoshii* or *T. onnurineus* NA1, *Thermococcus* sp. 9° N-7, *Thermococcus* sp. GI-J, *Thermococcus* sp. MAR-13, *Thermococcus* sp. GB-C, *Thermococcus* sp. GI-H, *Thermus aquaticus, Thermus thermophilus, Thermus caldophilus, Thermus filiformis, Thermus flavus, Thermotoga maritima, Bacillus stearothermophilus*, or *Bacillus caldotenax*, for example.

In exemplary embodiments, the amplified nucleic acids are labeled during the amplification reaction. In certain instances, the portion of the sample treated with methylation-sensitive DNase is labeled with a first label, and the control portion of the sample is labeled with a second label. In some embodiments, each label is detectable by CE.

Labels include, but are not limited to: light-emitting, light-scattering, and light-absorbing compounds which generate or quench a detectable fluorescent, chemiluminescent, or bioluminescent signal (see, e.g., Kricka, L., Nonisotopic DNA Probe Techniques, Academic Press, San Diego (1992) and Garman A., Non-Radioactive Labeling, Academic Press (1997).). Fluorescent reporter dyes useful as labels include, but are not limited to, fluoresceins (see, e.g., U.S. Pat. Nos. 5,188,934, 6,008,379, and 6,020,481), rhodamines (see, e.g., U.S. Pat. Nos. 5,366,860, 5,847,162, 5,936,087, 6,051,719, and 6,191,278), benzophenoxazines (see, e.g., U.S. Pat. No. 6,140,500), energy-transfer fluorescent dyes, comprising pairs of donors and acceptors (see, e.g., U.S. Pat. Nos. 5,863,727; 5,800,996; and 5,945,526), and cyanines (see, e.g., WO 9745539). Examples of fluorescein dyes include, but are not limited to, 6-carboxyfluorescein; 2',4', 1,4,-tetrachlorofluorescein; and 2',4',5',7',1,4-hexachlorofluorescein. Example cyanine dyes include the WELLRED® infrared dyes D1, D2, D3 or D4. Additional labels may be derived from Lissamine™, phycoerythrin, Cy2, Cy3, Cy3.5, Cy5, Cy5.5, Cy7, FLUORX® (Amersham), ALEXA FLUOR®350, ALEXA FLUOR®430, AMCA, BODIPY® 630/650, BODIPY® 650/665, BODIPY®-FL, BODIPY®-R6G, BODIPY®-TMR, BODIPY®-TRX, CASCADE BLUE®, Cy3, Cy5, 6-FAM™, Fluorescein Isothiocyanate, HEX™, 6-JOE™, OREGON GREEN® 488, OREGON GREEN® 500, OREGON GREEN® 514, PACIFIC BLUE™, REG™, RHODAMINE GREEN™, RHODAMINE RED™, RENOGRAPHIN®, ROX™, SYPRO®, TAMRA™, Tetramethylrhodamine, and/or TEXAS RED®, as well as any other fluorescent moiety capable of generating a detectable and distinct dye signal from another label. Examples of fluorescein dyes include, but are not limited to, 6-carboxyfluorescein; 2',4', 1,4,-tetrachlorofluorescein; and 2',4',5',7',1,4-hexachlorofluorescein. In certain aspects, the fluorescent label is selected from SYBR®-Green, 6-carboxyfluorescein ("FAM™"), TET™, NED™, ROX™, VIC®, or JOE™ that are compatible with CE analysis. For example, in certain embodiments, labels are different fluorophores capable of emitting light at different, spectrally-resolvable wavelengths (e.g., 4-differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. Other examples may include FREEDOM® dyes that are commercially available surrogates for common dyes. It will be appreciated that pairs of fluorophores are chosen that have distinct emission spectra so that they can be easily distinguished.

In still a further aspect, labels are hybridization-stabilizing moieties which serve to enhance, stabilize, or influence hybridization of duplexes, e.g., intercalators and intercalating dyes (including, but not limited to, ethidium bromide and SYBR®-Green), minor-groove binders, and cross-linking functional groups (see, e.g., Blackburn et al., eds. "DNA and RNA Structure" in *Nucleic Acids in Chemistry and Biology* (1996)).

It will be appreciated that in circumstances using two or more labels in a single assay, labels that have distinct emission spectra are chosen such that they can be easily distinguished. In some examples, FAM™ and HEX™ labels can be used to label a first portion and a second portion of a sample. In additional embodiments, FAM™ or HEX™ may be used with NED™ or ROX™ labels, among others, in the methods described herein.

E. Analysis Methods

In some embodiments, the amplified nucleic acids are analyzed to determine methylation status. In exemplary embodiments, the analysis method is capillary electrophoresis (CE) using instruments familiar to those in the art such as the ABI 3100, 3130, 3730, or 3500 models. Other implementations include any instrument capable of electrophoretic sizing of DNA and multicolor resolution. For example, the Beckman Vidiera or SEQ6000 capillary electrophoresis systems for the detection of WELLRED® infrared dyes (D1, D2, D3 and D4) may also be used or the LICOR® instrument incorporating IRDYES®. Other methods that may be used include microfluidic CE systems such as the Agilent 2100 Bioanalyzer and similar platforms, mass spectrometry, agarose gel electrophoresis followed by scan densitometry, and analysis of radiolabeled products using phosphorimager or scan densitometry of autoradiographs. In additional embodiments, the amplified nucleic acids from the first and the second portions of the sample are analyzed in a single CE assay.

Certain analysis methods such as CE allow for simultaneous characterization of methylation status and the number of CGG repeats present in a template. In certain embodiments, CE analysis is performed using POP™-4, 5, 6, or 7 liquid polymer with a 36 or 50 cm column. In one embodiment, the liquid polymer is POP-7™.

In certain embodiments, a percentage methylation can be calculated. Intensities of peaks observed in CE electropherograms, phosphorimager scans, densitometric scans, mass spectra, or other forms of data can be determined according to suitable methods known in the art, for example, methods such as peak height, area under the curve (integration), or curve fitting. Peak intensity values from corresponding peaks from the portions of the sample treated as the control and subjected to digestion by the methylation-sensitive DNase can then be compared; the peak intensities can be normalized using the GC reference standard. For example, normalization can be performed by expressing each observed peak intensity as a ratio to the peak intensity observed for the GC reference standard in the same portion of the sample.

In other embodiments, methylation status can be characterized as non-methylated or methylated. In still further embodiments, methylation status can be categorized as non-methylated, partially methylated, or fully methylated.

II. SAMPLES

The methods provided herein relate to characterization of the methylation status of a nucleic acid template in a sample. In certain embodiments, a nucleic acid sample is obtained from a human. For example, the sample may be a patient sample. A "patient sample" is any biological specimen from a patient. The term includes, but is not limited to, biological fluids such as blood, serum, plasma, urine, cerebrospinal fluid, tears, saliva, lymph, dialysis fluid, lavage fluid, semen, and other liquid samples, as well as cells and tissues of biological origin. Cells and tissues may include buccal cells, mouthwash collections, or skin cells, including hair follicles. The term also includes cells isolated from a human or cells derived therefrom, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. It may also include post-mortem solid tissue samples, such as those from brain. In some embodiments, the sample contains less than about 80, 100, 150, 200, 500, or 1,000 ng of DNA.

In some instances, the sample includes genomic DNA. The DNA may be separated from other non-DNA components of the sample before being subjected to the methods of the invention. Many methods of DNA separation and purification are known in the art.

A sample may contain a DNA template. In certain methods described herein, a DNA template may be the target of synthesis in a reaction catalyzed by a DNA polymerase. The GC-richness of the DNA template may be greater than or equal to 75, 80, 85, 90, 95, 96, 97, 98, 99, or 99.5% C and G residues. The DNA template may comprise di-, tri-, or tetranucleotide repeats comprising C and G residues. The DNA template may comprise a sequence within or near a disease-associated locus. The DNA template may comprise at least part of the 5' UTR of the FMR1 or FMR2 gene. The DNA template may comprise CGG repeats of the 5' UTR of the FMR1 or CCG repeats in the 5' UTR of the FMR2 gene. The size of the DNA template may be about 50, 100, 200, 300, 500, or 700 bp, or 1, 1.5, 2, 2.5, 3, 4, 5, 7, or 10 kb. The size of the DNA template may be between 50 bp and 10 kb, 100 bp and 10 kb, 200 bp and 10 kb, 300 bp and 10 kb, 500 bp and 10 kb, 700 bp and 10 kb, 1 kb and 10 kb, 1.5 bp and 10 kb, 2 bp and 10 kb, 3 bp and 10 kb, 50 bp and 7 kb, 50 bp and 5 kb, 50 bp and 4 kb, 50 bp and 3 kb, 50 bp and 2 kb, 50 bp and 1.5 kb, 100 bp and 7 kb, 200 bp and 5 kb, or 300 bp and 4 kb.

III. EXAMPLES

The following examples illustrate various embodiments of the invention and are not intended to limit the scope of the invention.

Example 1. Workflow for Characterizing Methylation Status

FIG. 1 shows an example of the mPCR methodology described herein. Sample DNA is treated with a reaction mix containing a methylation-sensitive DNase such as HpaII i, which degrades the unmethylated templates but retains the methylated alleles, or with a control mix without the methylation-sensitive enzyme. Each portion of the sample DNA is subject to PCR in the presence of an external GC reference standard. The PCR is further capable of amplifying alleles with over 200 CGG repeats. The primers for the HpaII portion and the control portion have different labels (e.g., FAM™ and HEX™). The PCR products are then pooled and analyzed by capillary electrophoresis. A loss in amplicon signal on CE indicates digestion and the lack of methylation at either HpaII site, whereas the retention of signal indicated methylation of the corresponding allele. The fraction of methylation by allele is determined from the ratio of amplicon yield for a given allele that was digested with HpaII relative to that for the corresponding undigested allele. This ratio is normalized to the signal of the external GC reference standard.

Example 2. Experimental Procedures

A. Clinical and Cell Line DNA Samples gDNA from blood samples were obtained from subjects seen at the M.I.N.D. Institute Clinic, following Institutional Review Board approval (Filipovic-Sadic et al., *Clin Chem* 2010; 56:399-408). Cell line DNA samples were obtained from the Coriell Cell Repositories (CCR, Coriell Institute for Medical Research, Camden, N.J.). Clinical and cell line DNA samples were diluted to 20 ng/µL in 10 mM Tris, 0.5 mM EDTA, pH 8.8 prior to PCR.

B. FMR1 Methylation PCR

Two aliquots of 40 ng gDNA from each sample are prepared for methylation assessment using AMPLIDEX™ Methylation PCR reagents (Asuragen, Inc., Austin, Tex.). Restriction enzymes are from New England Biolabs. One aliquot of DNA is mixed with digestion buffer and methylation-sensitive enzyme (HpaII unless otherwise noted), and the second aliquot with digestion buffer and a control enzyme such as Sau3AI or EcoRI. The restriction enzymes are present in the reaction mixture in a final concentration of 0.15 U/µl. Examples of the final concentration of buffer components in each reaction are shown in Table 1 (not including reagent contributions from the enzyme storage buffer).

TABLE 1

Exemplary Reaction Conditions

| Reagent | Concentration |
|---|---|
| Digestion Mix A | |
| MgCl₂ | 10 mM |
| Bis-Tris-Propane-HCl, pH 7.0 | 10 mM |
| Dithiothreitol | 1 mM |
| Digestion Mix B | |
| MgCl₂ | 10 mM |
| Tris-HCl | 50 mM |
| NaCl | 100 mM |
| Digestion Mix C | |
| MgCl₂ | 7.5 mM |
| TrisHCl, pH 7.5 | 10 mM |
| BSA | 100 µg/ml |

The HpaII and control reactions are incubated at 37° C. for two hours in sealed 96 well plates. Separate PCR mastermixes of methylation PCR reagents are prepared for either the HpaII-treated (FAM™ primers) or non HpaII-control (HEX™ primers) products, and are dispensed directly into the restriction enzyme digestion or the control digestion mixture. Each mastermix contains mPCR AMP Buffer (Asuragen, Catalog No. 145152), GC-rich Polymerase Mix (Asuragen, Catalog No. 145153), deionized water, and mPCR primers (Fwd: 5'TCAGGCGCTCA-GCTCCGTTTCGGTTTCA-3' (SEQ ID NO: 42); Rev: 5'-FAM™- or HEX™-AAGCGCCATTGGAGCCCCG-CACTTCC (SEQ ID NO: 43)) (Filipovic-Sadic, 2010). Each mastermix also contains an external GC reference standard (3000-12,000 copies/PCR reaction, depending on the number of PCR cycles).

The final PCR buffer/reagent conditions are the same as in the AMPLIDEX™ FMR1 kit (Asuragen, Catalog No. 49402; US Application No. 2010/0209970), except for additional 0.67 mM MgCl₂, 2.66 mM Bis-Tris-Propane, pH 7.0, and 0.266 mM DTT (for Digestion Mix A samples); additional 10 mM TrisHCl, pH 7.5, and 20 mM NaCl (for Digestion Mix B samples); or additional 2.66 mM TrisHCl, pH 7.5, and 26.6 µg/ml BSA (for Digestion Mix C samples) carried over from the digestion buffer.

Certain reactions may use a GC reference standard that has a relative retention time of 40 CGG (SEQ ID NO: 44; "40-CGG-Control"), which is constructed by inserting 30 nucleotides of a non-human DNA sequence to a plasmid containing 30 CGG repeats. During the PCR step, the reference standard is amplified from the plasmid. Additional examples include a reference standard that has a relative retention time of zero CGG (Asuragen, Catalog No. 49441; SEQ ID NO: 45; "zero-CGG-Control"), also contained within a plasmid. Non-plasmid controls with alternate migration times are also used, as noted.

The samples are PCR amplified with an initial heat denature step of 95° C. for 5 minutes, followed by 25 cycles of 97° C. for 35 sec, 62° C. for 35 sec and 72° C. for 4 min, and 72° C. for 10 minutes. Amplicons are prepared for CE analysis, or stored at −15 to −30° C.

The sequence of the FMR1 amplicon, along with indication of the two HpaII sites that are probed is depicted as follows:

5'-X-(CGG repeat region)-Y-3'
wherein X is (SEQ ID NO: 46)
TCAGGCGCTCAGCTCCGTTTCGGTTTCACTT*CCGG*TGGAGGGCCGCCT

CTGAGCGGGCGGCGGGCCGACGGCGAGCGCGGGCGGCGGCGGTGACGG

AGGCGCCGCTGCCAGGGGGCGTGCGGCAGCG;

and
Y is (SEQ ID NO: 47)
CTGGGCCTCGAGCGCCCGCAGCCCACCTCTCGGGGGCGGGCTC*CCGG*CG

CTAGCAGGGCTGAAGAGAAGATGGAGGAGCTGGTGGTGGAAGTGCGGGG

CTCCAATGGCGCTT-3'.

In SEQ ID NOs: 46 and 47, the underlined regions designate sequences bound by the forward and reverse primers, and the italicized and underlined CCGG sequences indicate the two HpaII sites.

C. Capillary Electrophoresis (CE)

A 3130xl Genetic Analyzer (Applied Biosystems Inc., ABI, Foster City, Calif.) is used for the experiments, except where noted. A total of 2 µL of unpurified PCR products (1 µL each from the HEX™-labeled products and FAM™-labeled products) are mixed with 11 µL of HI-DI FORMA-MIDE® (ABI) and 2 µL of ROX™ 1000 Size Ladder (Asuragen), heat denatured at 95° C. for 2 minutes and transferred to the CE system for analysis. Except where noted, injections follow the standard fragment sizing conditions (36 cm, POP7™) using an injection of 2.5 kV for 20 s and a 40 min run at 15 kV. An ABI 3500xL CE (50 cm, POP7™) is used where noted. Due to resolution limitations of the POP7 polymer, all FMR1 amplicons with >250 CGG repeats have similar mobilities on CE.

D. Data Analysis

Electropherograms are analyzed using GENEMAPPER® 4.0 (4.1 for 3500xL data) or PEAKSCANNER® V1.0 software (ABI). The conversion of base pair size to number of CGG repeats is determined by linear regression to control amplicons produced from templates with 20, 29, 31, 54 and 119 CGG repeats (Filipovic-Sadic, 2010). Peak sizes for each peak are converted to CGG repeat length using (Size$_i$−230.3/2.975).

Results of CGG repeat length and percent methylation for each detected allele are tabulated in MS Excel. The percent methylation, % $M_i$, is calculated as a ratio of peak heights between the digested (Peak$_{i,FAM™}$) and undigested sample (Peak$_{i,HEX™}$) normalized to the GC reference standard amplicon peak height (CTRL$_{HEX™}$ or CTRL$_{FAM™}$) as shown in Equation 1:

$$\% \ M_i(\text{height}) = \left(\frac{CTRL_{HEX}}{CTRL_{FAM}}\right)\frac{Peak_{i,FAM}}{Peak_{i,HEX}} \quad (1)$$

Methylation values that are about 100% or nominally exceed 100% are scored as fully methylated. Such values typically observed within the range of variation of the assay for well represented alleles, as noted below, but are sometimes exaggerated (e.g., 120 to 137%) in methylation assessments of low abundance alleles (e.g., inputs of only 1% mass fraction of a clinical full mutation sample) when the allele-specific signal is near the lower range of detection of the CE instrument and thus quantitatively less reliable relative to the signal of the GC reference standard peak.

E. Southern Blot Analysis

SB analysis of the 80 clinical samples is performed as described in Tassone et al., *J Mol Diagn* 2008; 10:43-9. Cell line DNA is prepared for SB using EcoRI and EagI (NEB). SB images are assessed categorically (unmethylated, partially methylated and fully methylated alleles) and the percent of methylation in each sample determined as described in Tassone, 2008.

Example 3. Accuracy and Reproducibility of mPCR with Methylated DNA Standards and Samples To assess the accuracy of the two-color mPCR workflow, a set of 8 defined analytical standards containing 30 CGG repeats and known methylation fractions were developed. Methylated and unmethylated DNA controls were prepared from PCR products of a 30 CGG repeat allele that was cloned into pBR322 following standard procedures (Sambrook J, Fritsch E F, Maniatis T. *Molecular Cloning: A Laboratory Manual.* 2nd ed. Cold Spring Harbor, N.Y.: CSHL Press, 1989). The 30 CGG standard was methylated with Hpa II methyltransferase (New England Biolabs, NEB, Ipswich, Mass.) and linearized with HindIII® (NEB).

Various proportions of the methylated or unmethylated 30 CGG standards were mixed from 0-100% and diluted to $1.5 \times 10^4$ copies/µL in 20 ng/µL of 645 CGG cell line DNA (NA04025, CCR). Cell line DNA samples were obtained from the Coriell Cell Repositories (CCR, Coriell Institute for Medical Research, Camden, N.J.). Each sample was subject to HpaII digestion in Digestion Mix A (Sau3A1 in Digestion Mix A for control reaction), 25 cycles of PCR in the presence of the 40-CGG-Control, and CE as described in Example 2.

A series of electropherograms highlighting the proportional change in signal in the FAM™-channel for the 30 CGG standard are shown in FIG. 3A. As the percent methylation increased, the signal for the 30 CGG standard increased relative to the peaks for 40-CGG-control and the admixed 645 CGG full mutation allele. The change in peak height was normalized to the 40-CGG-Control peak height and compared to the normalized ratio in the HEX™ channel (Eq. 1). A linear relationship ($R^2$=0.998) was observed between the known methylation fraction and the fraction empirically recovered following mPCR, as performed by two operators over three different run days (FIG. 3B), with input methylation indicated on the x-axis, and measured methylation indicated on the y-axis. Methylation of the 645 CGG allele was determined to be quantitative (104±5%) for each of the evaluated standards (FIG. 3B).

The reproducibility of mPCR was further assessed across 8 replicates of 2 normal alleles (30 and 32 CGG from a female clinical sample) and 2 full mutation alleles (550 CGG and 940 CGG) on 2 CE instrument platforms (an ABI 3130xl and 3500xL). Methylation fractions, standard deviations, coefficients of variation (CV), and 95% confidence intervals (CI) are presented in Table 2.

TABLE 2 mPCR assessments of methylation across two CE platforms for normal and full mutation alleles.

| Platform | Sample | Allele (CGG) | Average (%) | Stdev (%) | CV | 95% CI |
|---|---|---|---|---|---|---|
| 3130xl | AS10017 | 30 | 74 | 5.3 | 7% | 70.4-77.7 |
|  | AS10017 | 32 | 25 | 2.0 | 8% | 23.4-26.2 |
|  | NA07862 | ~550 | 101 | 10.0 | 10% | 94.5-108.4 |
|  | NA09237 | ~940 | 97 | 15.7 | 16% | 86.5-108.3 |
| 3500xL | AS10017 | 30 | 76 | 5.7 | 8% | 71.8-79.7 |
|  | AS10017 | 32 | 27 | 2.1 | 8% | 25.9-28.8 |
|  | NA07862 | ~550 | 101 | 8.0 | 8% | 95.7-106.8 |
|  | NA09237 | ~940 | 97 | 12.0 | 12% | 88.6-105.3 |

The calculated mPCR methylation fraction yielded a CV=7-8% for the normal alleles, and a CV=8-16% for the full mutation alleles across the two different platforms. In addition, mPCR results were reproducible across 2 different operators (CV=7%) using 8 cell line samples, including 4 full mutation samples. Measurements of percent methylation that sometimes exceeded 100% were a consequence of the stated variation of the method, and such samples were tabulated as fully methylated for comparison purposes with SB analysis. As demonstrated in the examples below, the mPCR method yielded results for clinical samples that were at least as good as SB analysis.

Example 4: mPCR Assessments of Cell Line DNA and Comparisons with SB Analysis mPCR was evaluated with 8 commercially available cell line DNA templates that included normal, premutation and full mutation alleles from both male and female samples. Samples were subject to HpaII digestion in Digestion Mix A (Sau3A1 in Digestion Mix A for control reaction), 25 cycles of PCR in the presence of the 40-CGG-Control, and CE as described in Example 2. Results for allele size and methylation status from mPCR and SB analyses are summarized in Table 3.

TABLE 3

Comparison of mPCR and SB analyses for 8 cell line DNA samples.
Samples in bold are shown in FIG. 4.

| Sample Information | | | | SB Analysis | | mPCR | |
|---|---|---|---|---|---|---|---|
| Sample ID | Genotype | Sex | Coriell Catolog Repeat Length (CGG) | Estimated Size (~CGG) | Categorical Methylation (full, partial, or non) | mPCR CE Repeat length | Methylation % on CE |
| NA06892 | PM | M | 93 (80-85) | ~110 | Non | 90 | 2% |
| NA09145 | FM | M | full | 660~990 | Full | >250 | 109% |
| NA06852 | FM | M | >200 | 395 | Full | >250 | 108% |

TABLE 3-continued

Comparison of mPCR and SB analyses for 8 cell line DNA samples.
Samples in bold are shown in FIG. 4.

| Sample Information | | | | SB Analysis | | mPCR | |
|---|---|---|---|---|---|---|---|
| Sample ID | Genotype | Sex | Coriell Catolog Repeat Length (CGG) | Estimated Size (~CGG) | Categorical Methylation (full, partial, or non) | mPCR CE Repeat length | Methylation % on CE |
| NA04025 | FM | M | 645 | 795 | Full | >250 | 113% |
| NA09237 | FM | M | 931-940 | 1062 | Full | >250 | 109% |
| NA20241 | PM | F | 29/93-110 | Normal | Partial | 29 | 24% |
| | | | | 103-130 | Partial | 88 | 83% |
| | | | | | | 111 | 83% |
| | | | | | | 116 | 0% |
| NA06896 | PM | F | 23/95-140 | Normal | Partial | 23 | 21% |
| | | | | 148-201 | Partial | 112 | 69% |
| | | | | | | 136 | 96% |
| | | | | | | 153 | 0% |
| | | | | | | 175 | 0% |
| | | | | | | >250 | 0% |
| NA07537 | FM | F | 28/336 | Normal | Partial | 29 | 8% |
| | FM | | | 329 | Full | >250 | 100% |

Electropherograms of 4 samples with matching SB data are shown in FIGS. 4A-D. In each figure, the top panel shows the portion of the sample not treated with HpaII, and the bottom panel shows the digested sample. The sample ID from Table 3 is shown in each figure, along with the repeat length. Repeat lengths in FIG. 4 are labeled using the Coriell designations for >250 CGG, and using the results of PCR when <250 CGG. Each figure also includes methylation percentage determined by mPCR. The peak labeled "Ctrl" indicates the 40-CGG-control.

Figure 4A:
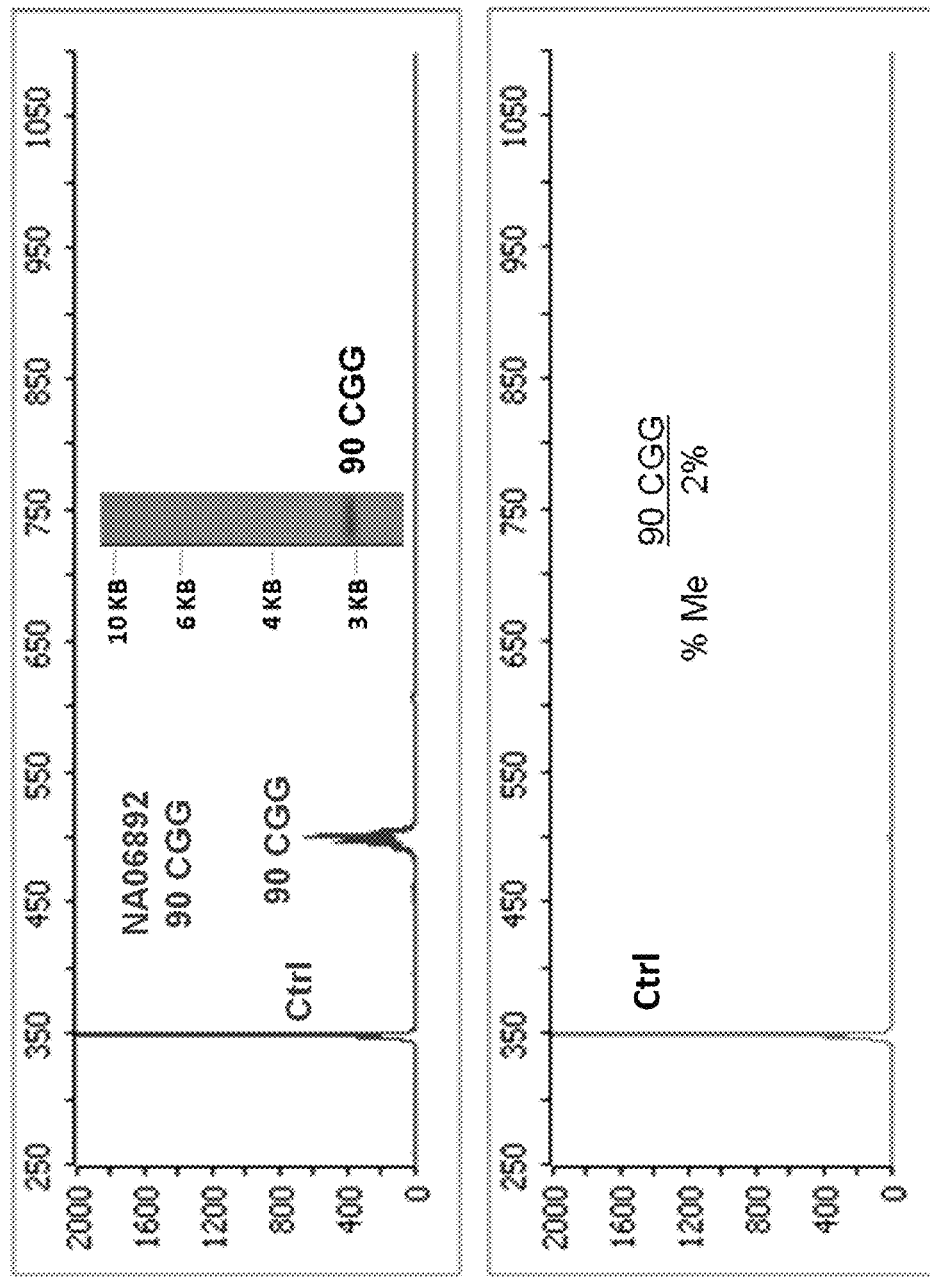
FIGS. 4A-D show capillary electropherograms of 4 cell line samples subject to mPCR, with matching SB data.
Figure 4B:
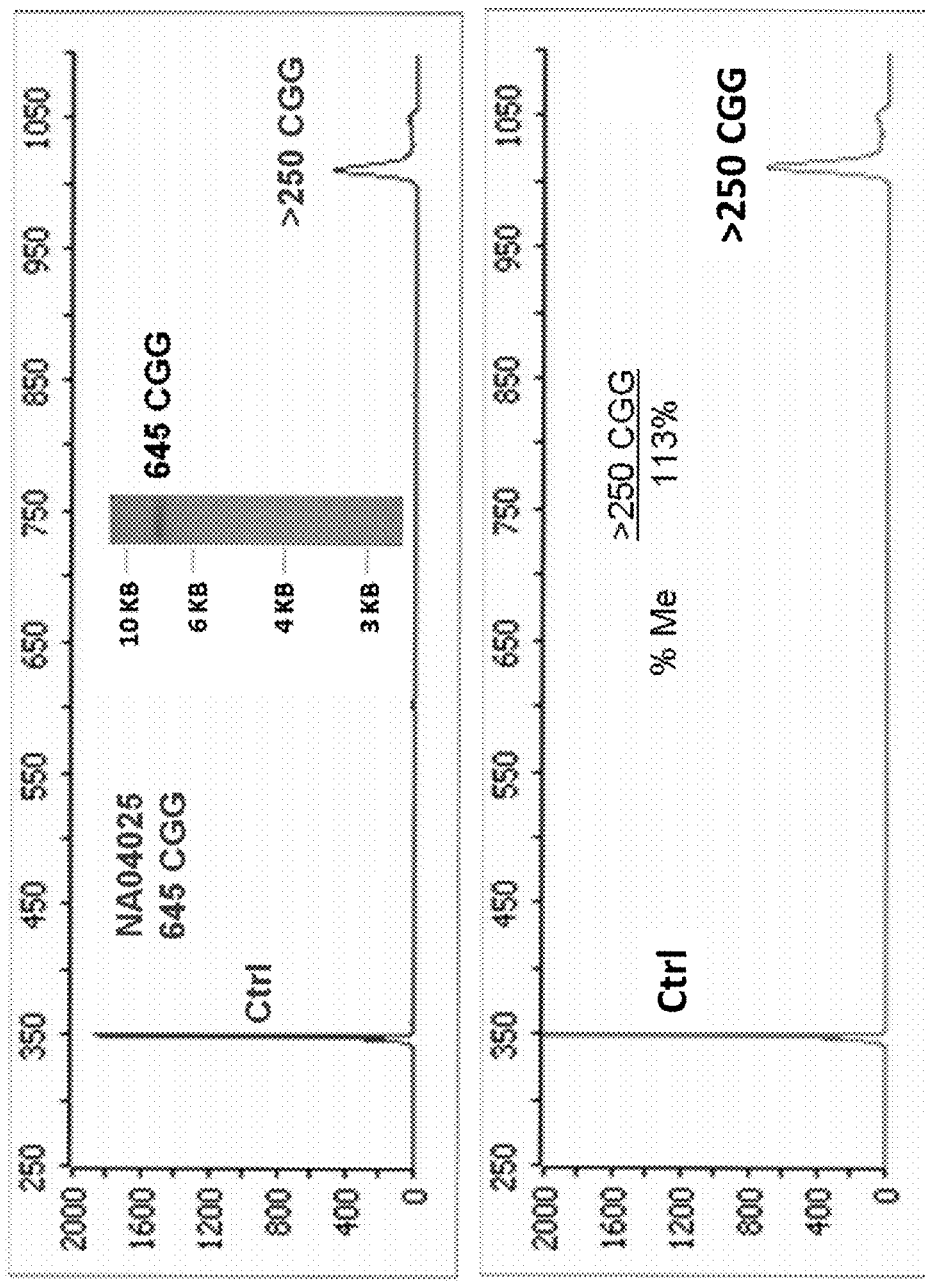
Figure 4C:
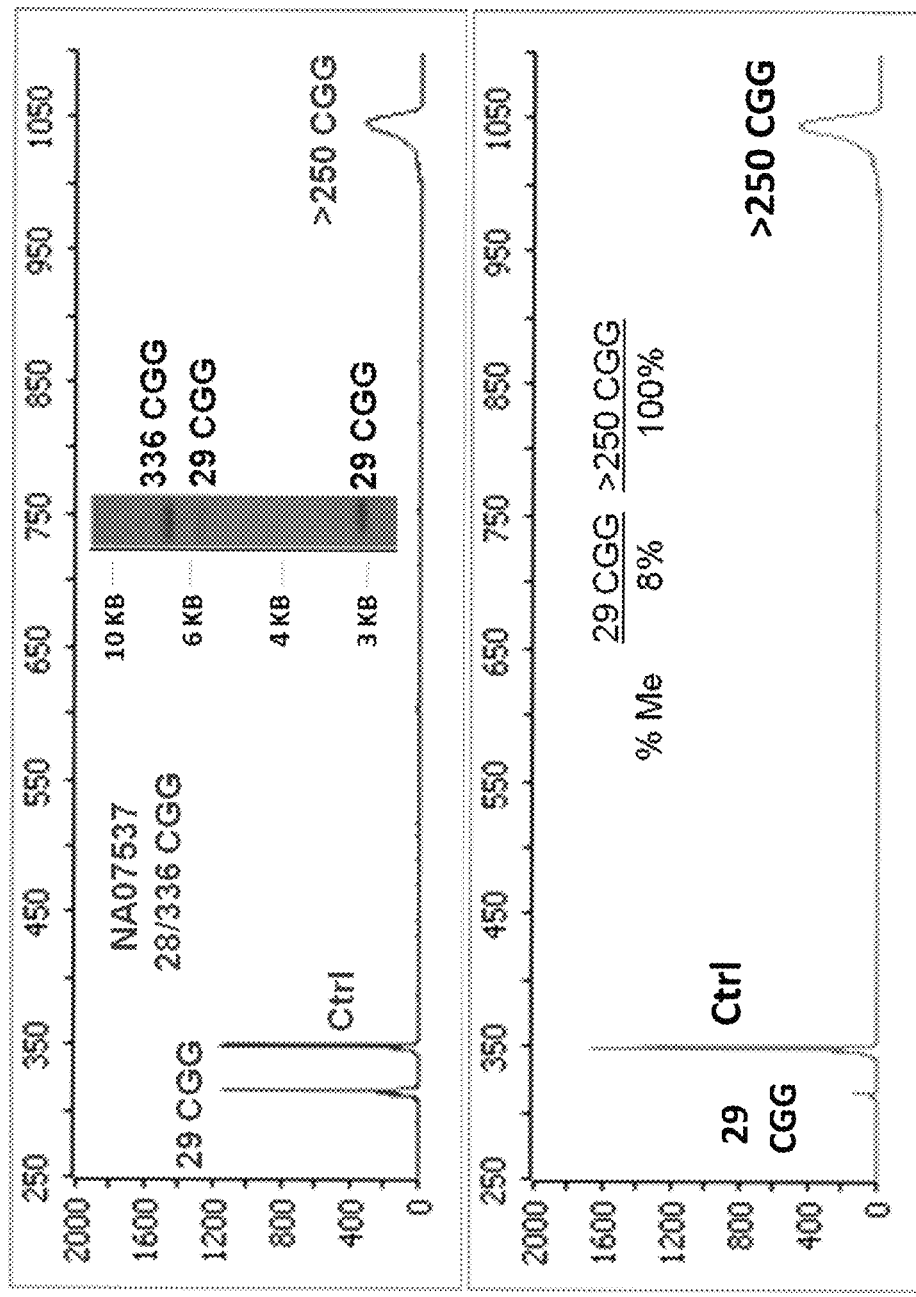
Figure 4D:
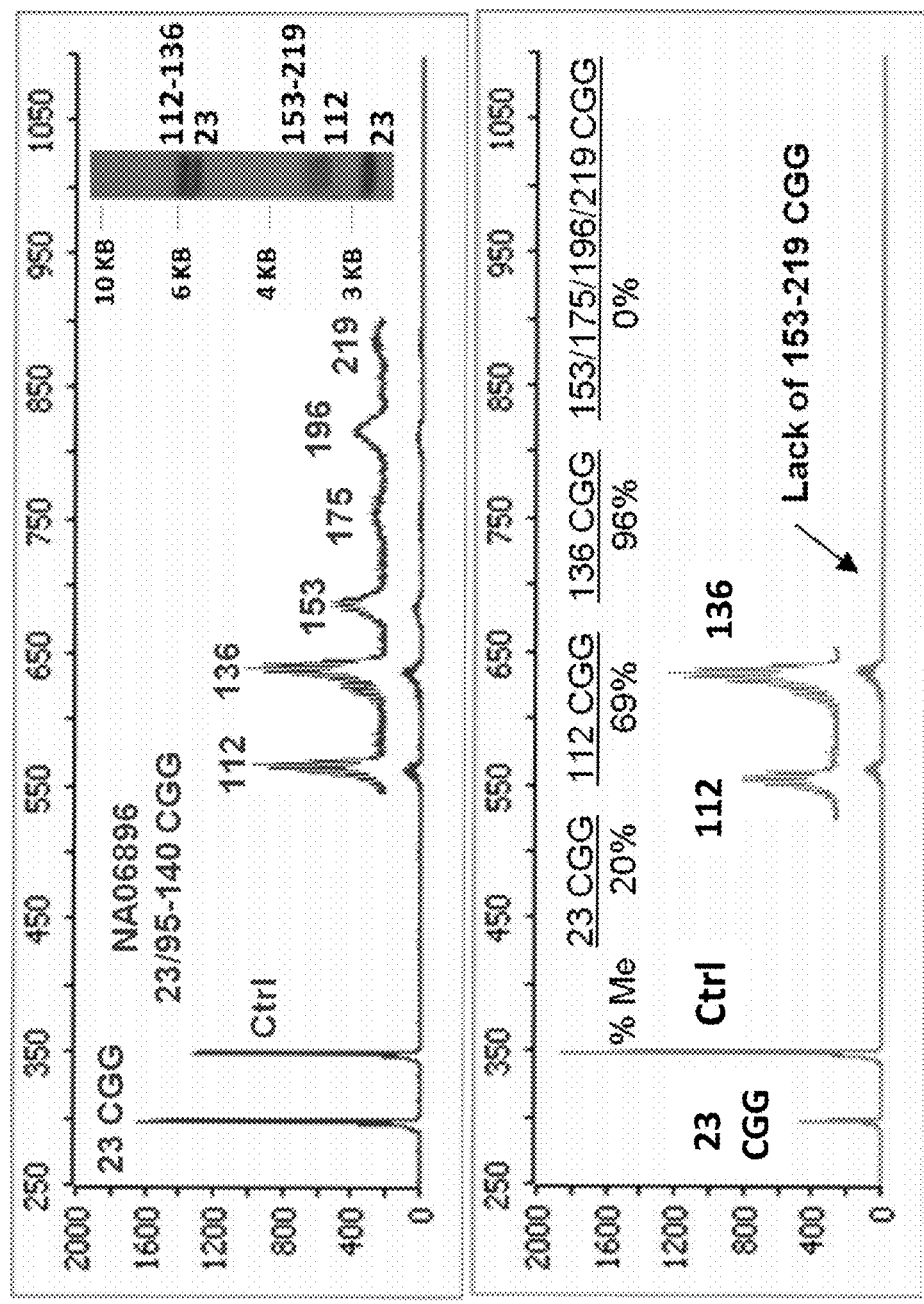
Figure 5A:
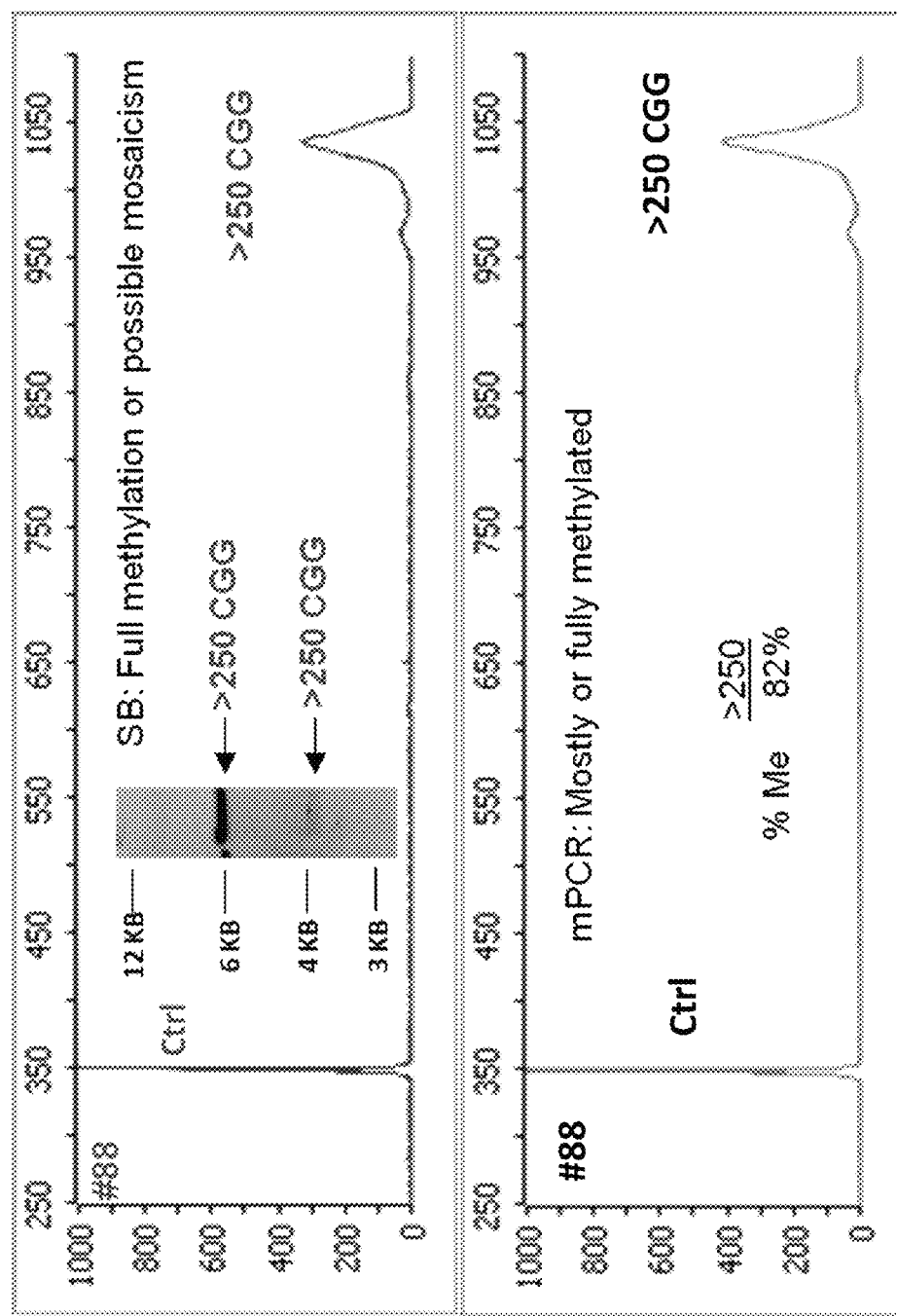
FIGS. 5A-D show capillary electropherograms of 4 representative clinical samples with full mutation alleles, with matching SB data.
Figure 5B:
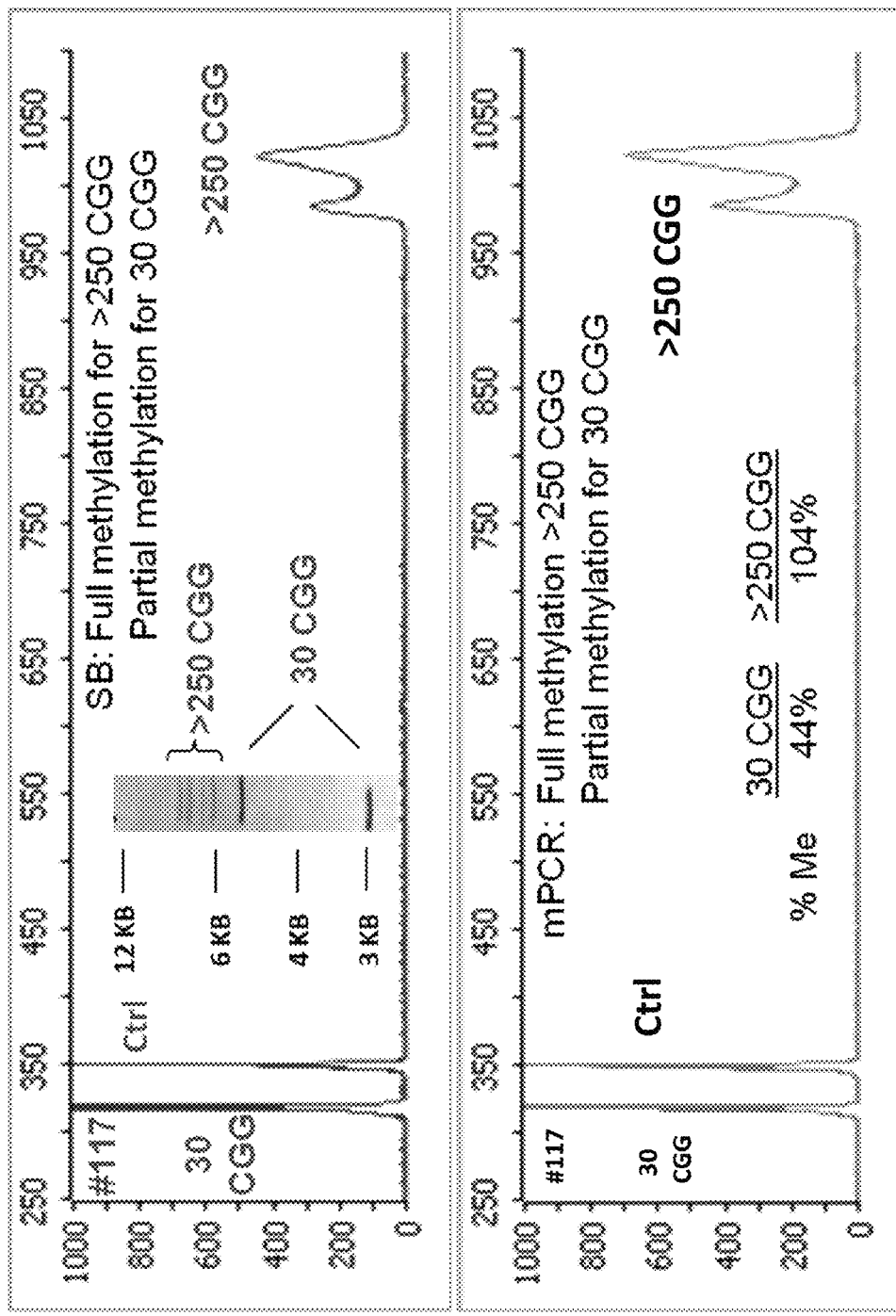
Figure 5C:
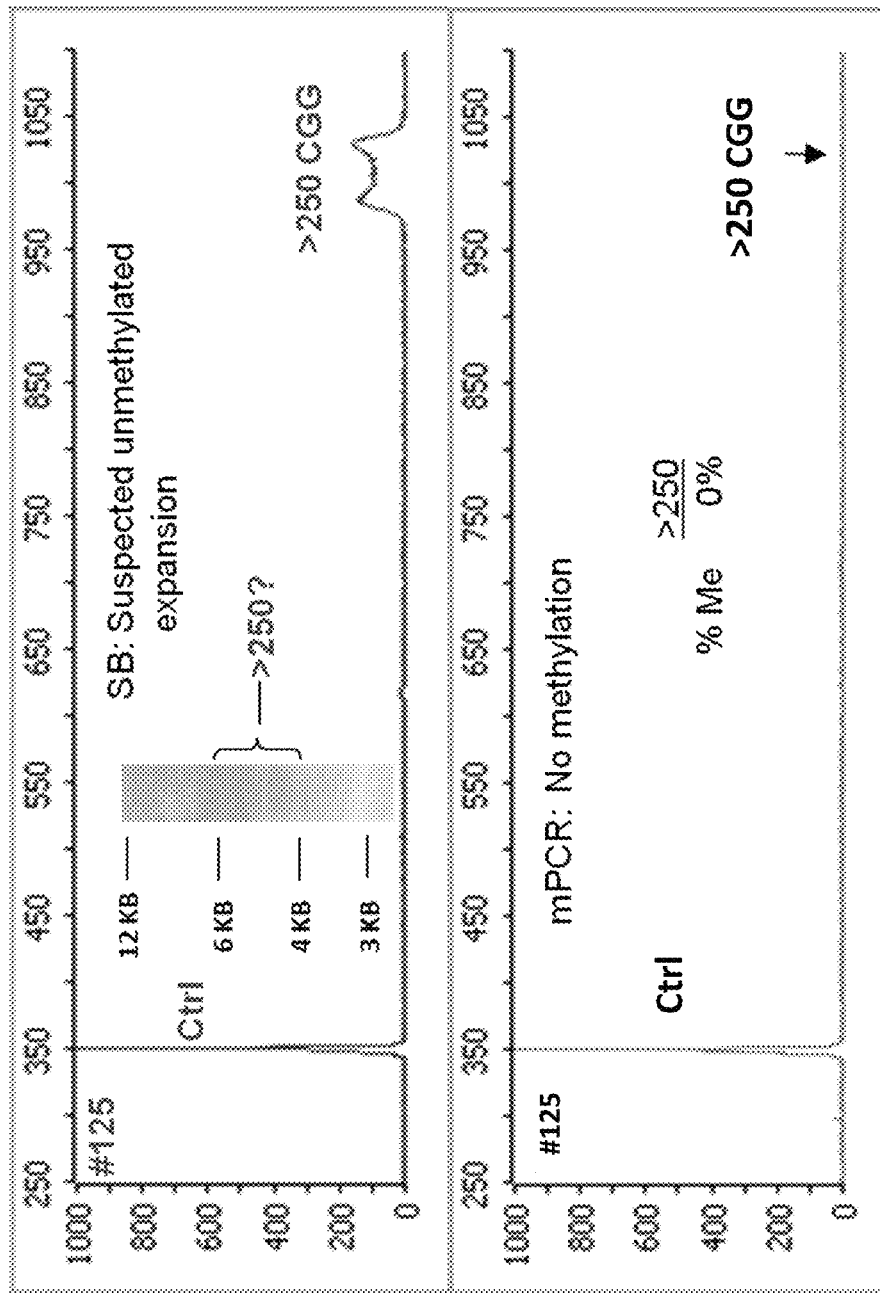
Figure 5D:
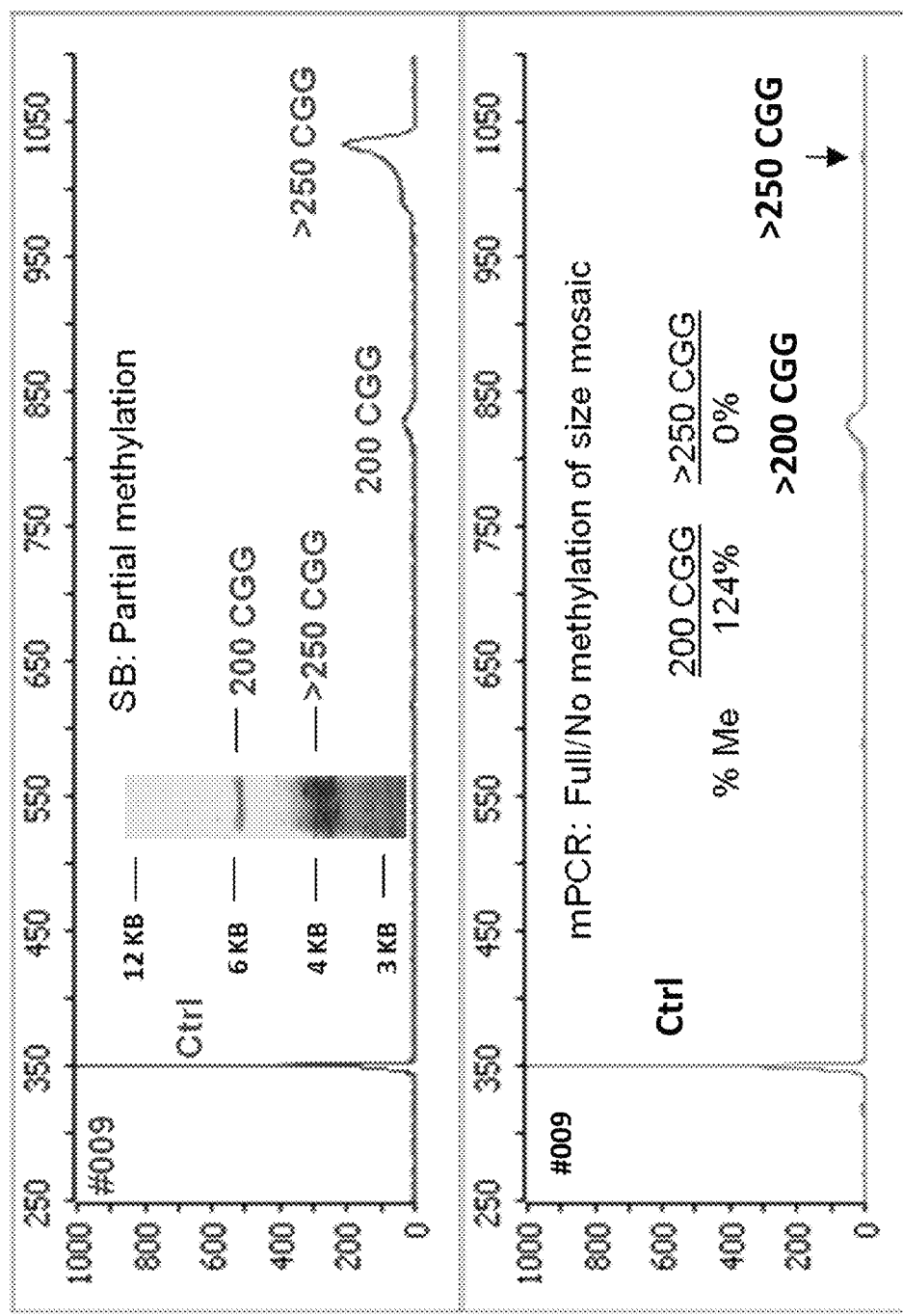
Figure 6A:
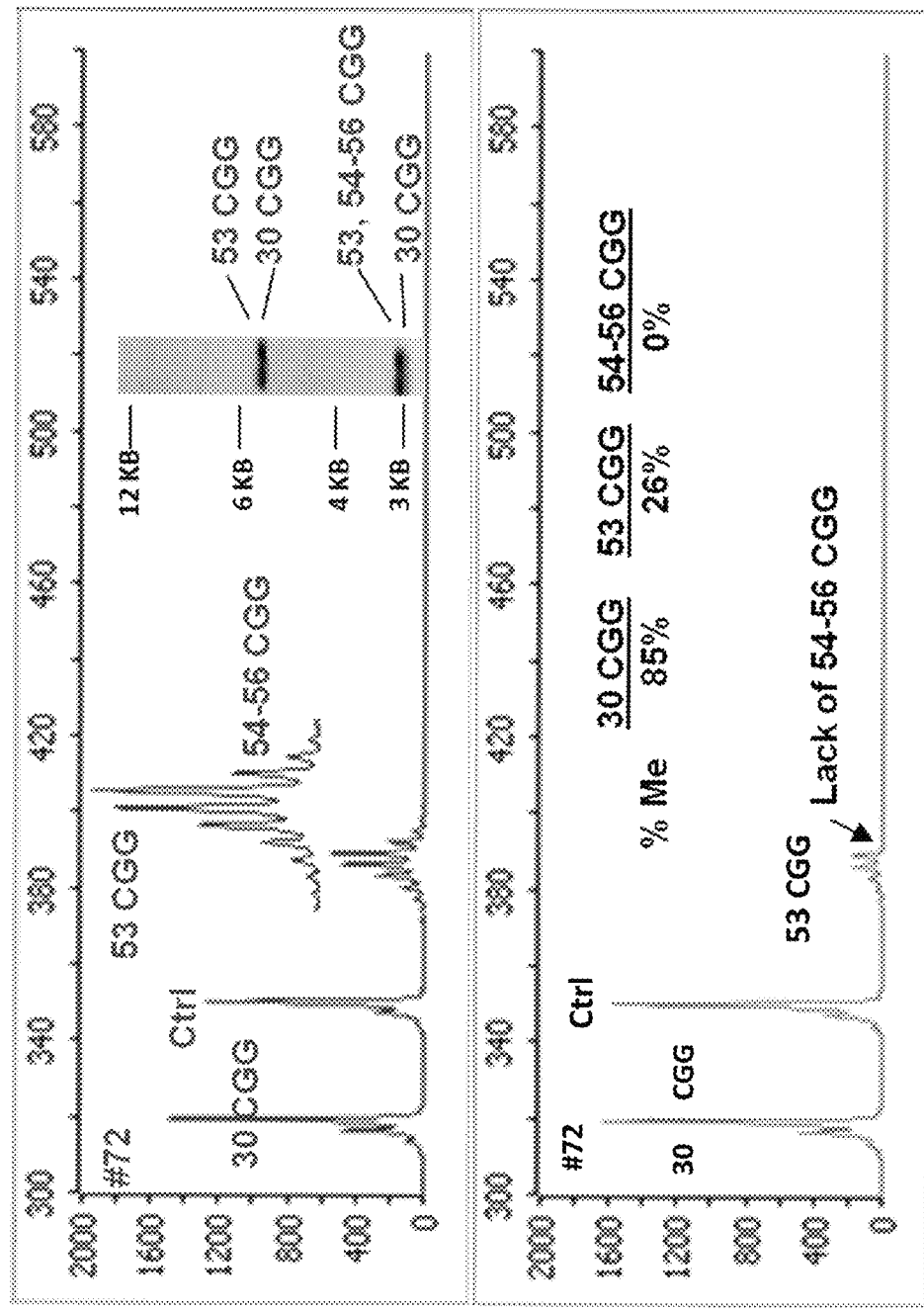
FIGS. 6A-D show capillary electropherograms of 4 representative clinical female permutation samples, with matching SB data.
Figure 6B:
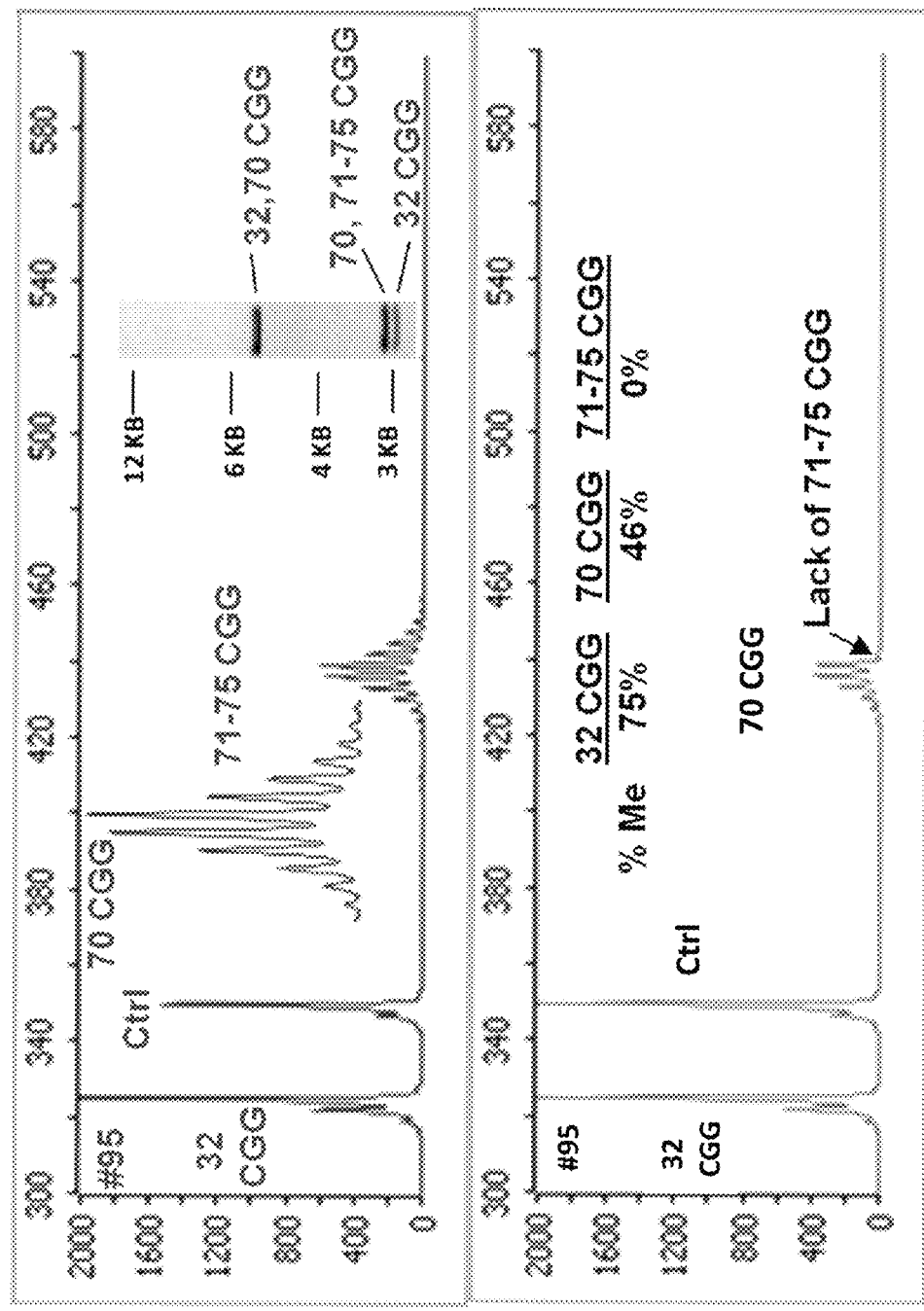
Figure 6C:
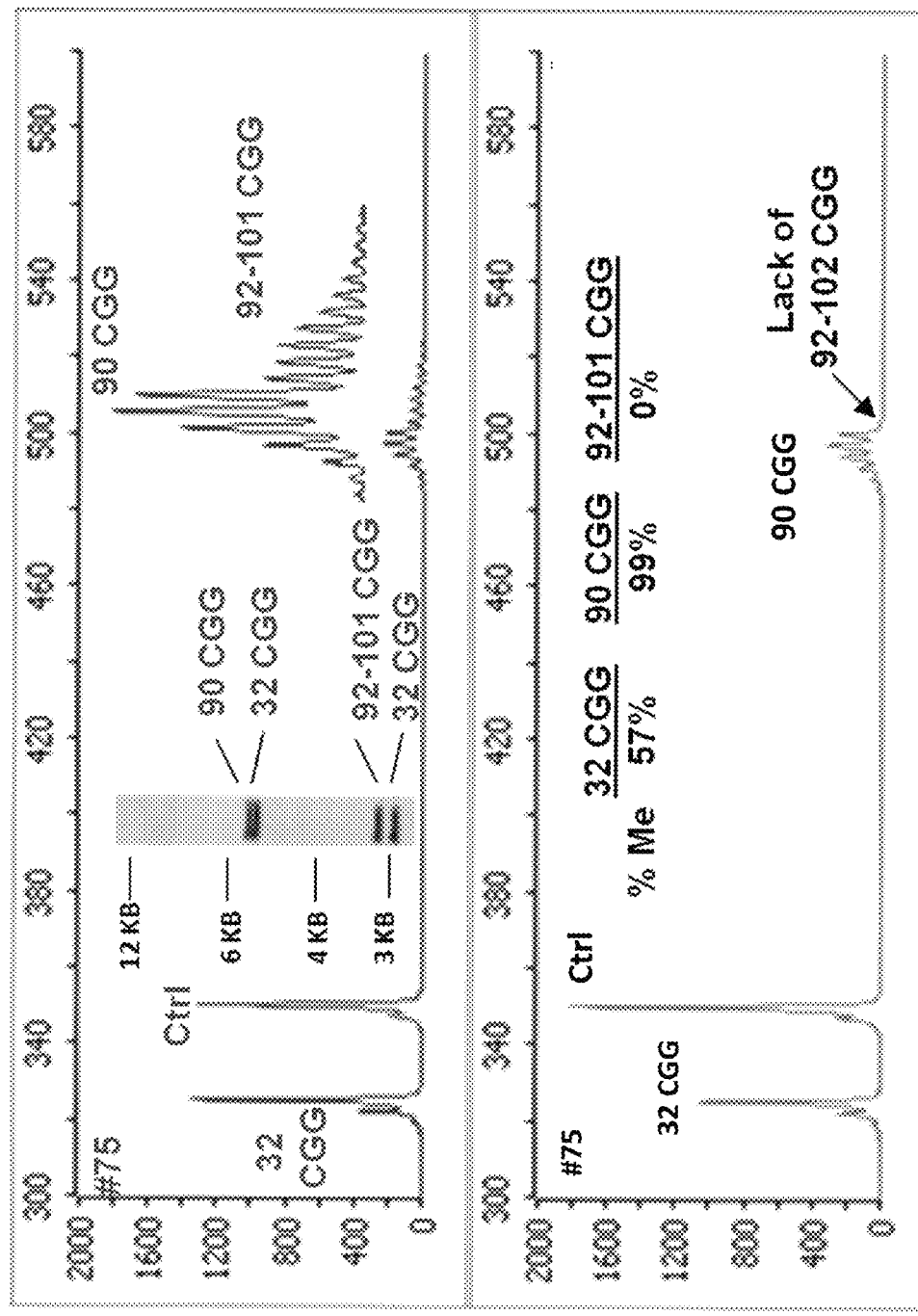
Figure 6D:
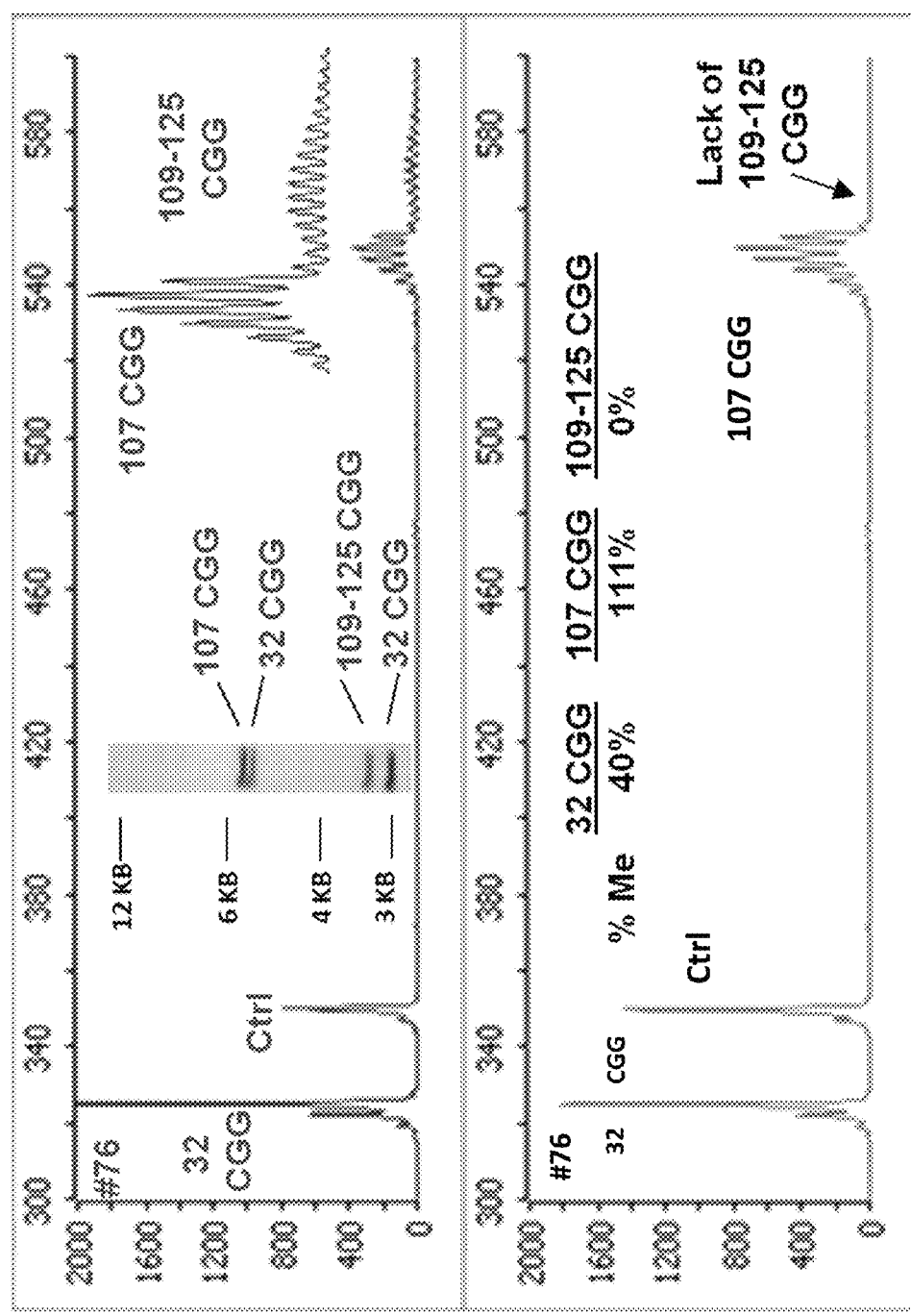

In each case, the mPCR results were qualitatively consistent with the corresponding SB data. For example, as shown in FIG. 4A, the male premutation allele (NA06892, 90 CGG) presented 2% methylation by mPCR, consistent with the presence of a product that was detected only in the unmethylated region of the SB. Skewed X-inactivation (8% methylation) of a female normal allele (NA07537, FIG. 4C), in combination with a fully methylated full mutation allele, was also concordant with SB analysis, and previously published data (Zhou et al., Clin Chem 52:1492-1500 (2006)).

mPCR provided more detailed interpretations of allele-specific methylation states in complex samples up to ~250 CGG in length. For example, a mosaic female sample (NA06896, "23/95-140" according to CCR) was detected with primary peaks of 23, 112, 136 CGG and 4 additional low abundance peaks of 153, 175, 196, and 219 CGG (FIG. 4D). The 23 CGG and 112 CGG peaks were partially methylated, the 136 CGG peak was fully methylated, and the peaks between 153 and 219 were completely unmethylated.

These results were qualitatively similar to the results from SB analysis. SB revealed a mostly unmethylated 23 CGG allele, a broad set of expanded unmethylated alleles (<5.2 kb), and a more defined set of expanded methylated alleles. Importantly, mPCR data revealed individual size mosaic contributions to the unmethylated smear pattern in SB. For example, the SB image was consistent with a partially methylated 112 CGG and unmethylated higher repeat alleles of 153-219 CGG as reported by mPCR.

Example 5. Methylation PCR Assay Performance with Clinical DNA Samples

The FMR1 mPCR assay was evaluated with a set of 80 clinical specimens representing the full range of clinically relevant allele sizes and methylation states, and selected from the same set previously evaluated for allele size (Filipovic-Sadic, 2010). Experiments were performed as described in Example 4. Methylation status was also determined by SB (Tassone, 2008). CGG repeat length, percent methylation and comparison to SB data were tabulated for each clinical sample (Table 4) and summarized (Table 5). In Table 4, alleles detected using mPCR were grouped to match resolution limits of SB. Samples with full mutation alleles are shown in italics, and those in bold are shown in FIGS. 5 and 6. In each figure, the peak labeled "Ctrl" indicates the 40-CGG-Control.

X-activation (Rousseau et al., J Med Genet 28:830-6 (1991)) is the reciprocal of percent methylation for female normal alleles in normal and full mutation samples. The average X-activation was 0.51 for normal female alleles (n=8) and 0.67 for the normal alleles of female full mutation (n=12) samples, consistent with values reported by de Vries et al (0.50 and 0.71, respectively) (de Vries et al., Am J Hum Genet 58:1025-32 (1996)).

TABLE 4

Comparison of mPCR repeat length and percent methylation with categorical calls and estimated methylation by SB.
Full mutations in Table 4 are shown in italics.

| | | mPCR | | | SB Analysis | |
|---|---|---|---|---|---|---|
| Sample ID | Sample Call | Repeat length (CGG) | Methylation | X-activation[a] | Categorical Call by SB[b] | Estimated methylation by SB[c] |
| #03 | FM | 160 | 0% | | Partial | 60% |
| | | >250 | 96% | | | |
| #04 | FM | 20 | 27% | 0.73 | Partial | 30% |
| | | >250 | 104% | | Full | 100% |
| #08 | FM | >250 | 108% | | Full | 100% |
| #09[a] | FM | 201 | 124% | | Partial | 50% |
| | | >250 | 0% | | | |
| #11 | PM | 29 | 83% | | Partial | 70% |
| | | 105 | 87% | | Partial | 40% |
| | | 108-116 | 0% | | | |
| #12 | FM | 218 | 110% | | Partial | 80% |
| | | >250 | 0% | | | |

TABLE 4-continued

Comparison of mPCR repeat length and percent methylation with categorical calls and estimated methylation by SB. Full mutations in Table 4 are shown in italics.

| | | mPCR | | | SB Analysis | |
|---|---|---|---|---|---|---|
| Sample ID | Sample Call | Repeat length (CGG) | Methylation | X-activation[a] | Categorical Call by SB[b] | Estimated methylation by SB[c] |
| #13 | FM | 39 | 50% | 0.5 | Partial | 50% |
| | | >250 | 83% | | Partial | 90% |
| #20 | FM | 29 | 18% | 0.82 | Partial | 15% |
| | | 226 | 111% | | Full | 100% |
| #54 | FM | >250 | 102% | | Full | 100% |
| #55 | FM | 30 | 56% | 0.44 | Partial | 40% |
| | | 214 | 84% | | Full (Faint) | >70% |
| | | >250 | 116% | | Full | 100% |
| #56 | PM | 30 | 4% | | Non | 0% |
| | | 84 | 96% | | Full | 100% |
| #57 | FM | >250 | 111% | | Full | 100% |
| #58 | PM | 30 | 35% | | Partial | 30% |
| | | 88 | 111% | | Partial | 60% |
| | | 89-101 | 0% | | | |
| #59 | FM | 30 | 0% | 1.0 | Non | 0% |
| | | >250 | 95% | | Full | 100% |
| #60 | FM | >250 | 100% | | Full | 100% |
| #61 | PM | 20 | 11% | | Partial | 10% |
| | | 147 | 127% | | Full | 100% |
| | | 180 | 102% | | | |
| #62 | FM | >250 | 103% | | Full | 100% |
| #63 | FM | 30 | 4% | 0.96 | Partial | 5% |
| | | 142 | 97% | | Full | 100% |
| | | 155 | 122% | | Full | |
| | | >250 | 109% | | Full | 100% |
| #64 | NOR | 31 | 0% | | Non | 0% |
| #65 | PM | 79-85 | 0% | | Non | 0% |
| #66 | FM | 186 | 92% | | Full | 100% |
| | | >250 | 114% | | Full | 100% |
| #67 | PM | 30 | 24% | | Partial | 20% |
| | | 92 | 125% | | Partial | 60% |
| | | 95-108 | 0% | | | |
| #68 | FM | 20 | 38% | 0.62 | Partial | 40% |
| | | >250 | 91% | | Full | 100% |
| #69 | FM | 30 | 5% | 0.95 | Partial | 5% |
| | | >250 | 112% | | Full | 100% |
| #70 | FM | 30 | 28% | 0.72 | Partial | 25% |
| | | >250 | 110% | | Full | 100% |
| #71 | NOR | 23 | 43% | 0.57 | Partial | 50% |
| #72[d] | INT | 30 | 57% | 0.43 | | |
| | | 30 | 85% | | Partial | 85% |
| | | 53 | 26% | | Partial | 30% |
| | | 54-55 | 0% | | | |
| #73 | PM | 63 | 0% | | Non | 0% |
| #74 | PM | 101-117 | 0% | | Non | 0% |
| | | 118-140 | 0% | | | |
| #75[d] | PM | 32 | 57% | | Partial | 50% |
| | | 90 | 99% | | Partial | 50% |
| | | 92-101 | 0% | | | |
| #76[d] | PM | 32 | 40% | | Partial | 30% |
| | | 107 | 111% | | Partial | 60% |
| | | 109-125 | 0% | | | |
| #77 | FM | 30 | 40% | 0.60 | Partial | 30% |
| | | >250 | 107% | | Full | 100% |
| #78 | NOR | 21 | 66% | | Partial | 50% |
| | | 30 | 45% | | | |
| | | 31 | 30% | | | |
| #79 | PM | 30 | 36% | | Partial | 50% |
| | | 60 | 64% | | | |
| | | 61-64 | 0% | | | |
| #80 | NOR | 30 | 0% | | Non | 0% |
| #81 | NOR | 29 | 49% | 0.51 | Partial | 40% |
| | | 30 | 37% | 0.63 | | |
| #82 | PM | 89 | 0% | | Non | 0% |
| #83 | PM | 34 | 10% | | Non | 0% |
| | | 79 | 115% | | Partial | 90% |
| | | 80-86 | 0% | | | |
| #84 | PM | 59 | 0% | | Non | 0% |
| #85 | PM | 20 | 23% | | Partial | 60% |
| | | 102 | 86% | | Partial | 20% |
| | | 103-113 | 0% | | | |
| #86 | PM | 30 | 76% | | Partial | 70% |
| | | 110 | 112% | | Partial | 20% |
| | | 112-124 | 0% | | | |
| #87 | FM | >250 | 96% | | Full | 100% |
| #88[e] | FM | >250 | 82% | | Partial | 90% |
| #89 | PM | 68 | 0% | | Non | 0% |
| #90 | FM | 223 | 70% | | Partial | 80% |
| | | >250 | 80% | | | |
| #91 | FM | 198 | 100% | | Partial | 50% |
| | | 228 | 0% | | | |
| #92 | NOR | 30 | 0% | | Non | 0% |
| #93 | NOR | 30 | 51% | 0.49 | Partial | 50% |
| | | 32 | 42% | 0.58 | | |
| #94 | FM | 236 | 101% | | Full | 100% |
| | | >250 | 75% | | Partial | 80% |
| #95[d] | PM | 32 | 75% | | Partial | 60% |
| | | 70 | 46% | | | |
| | | 71-75 | 0% | | | |
| #96 | PM | 35 | 45% | | Partial | 30% |
| | | 80 | 45% | | Partial | 50% |
| | | 81-85 | 0% | | | |
| #97 | PM | 92-96 | 0% | | Non | 0% |
| #98 | NOR | 23 | 0% | | Non | 0% |
| #99 | PM | 74-79 | 0% | | Non | 0% |
| | | 93-100 | 0% | | Non | 0% |
| #100 | PM | 65-70 | 0% | | Non | 0% |
| #101 | PM | 143-153 | 0% | | Non | 0% |
| #102 | INT | 30 | 38% | | Partial | 50% |
| | | 53 | 49% | | | |
| #103 | FM | >250 | 102% | | Full | 100% |
| #104 | FM | >250 | 96% | | Full | 100% |
| #105 | PM | 29 | 17% | | Partial | 10% |
| | | 92 | 100% | | Partial | 70% |
| | | 93-97 | 0% | | | |
| #106 | PM | 38 | 37% | | Partial | 40% |
| | | 78 | 80% | | Partial | 50% |
| | | 80-86 | 0% | | | |
| #107 | PM | 80-84 | 0% | | Non | 0% |
| | | 90-95 | 0% | | | |
| #108 | PM | 23 | 32% | | Partial | 35% |
| | | 71 | 63% | | Partial | 50% |
| | | 73-74 | 0% | | | |
| #109 | PM | 30 | 54% | | Partial | 50% |
| | | 86 | 90% | | Partial | 50% |
| | | 88-94 | 0% | | | |
| #110 | FM | >250 | 93% | | Full | 100% |
| #111 | PM | 106-110 | 0% | | Non | 0% |
| #112 | PM | 41 | 11% | | Partial | 10% |
| | | 112 | 165% | | Partial | 55% |
| #113 | FM | >250 | 99% | | Full | 100% |
| #114 | NOR | 31 | 0% | | Non | 0% |
| #115 | NOR | 30, 30 | 51% | 0.49 | Partial | 50% |
| #116 | NOR | 30 | 46% | 0.54 | Partial | 50% |
| | | 31 | 51% | 0.49 | | |
| #117[e] | FM | 30 | 44% | 0.56 | Partial | 50% |
| | | >250 | 104% | | Full | 100% |
| #118 | FM | 29 | 81% | 0.19 | Partial | 90% |
| | | 97 | 0% | | Non | 0% |
| | | 130 | 0% | | Non | 0% |
| | | >250 | 74% | | Full (Faint) | >50% |
| #119 | FM | 99 | 0% | | Not visible | |
| | | >250 | 101% | | Full | 100% |

TABLE 4-continued

Comparison of mPCR repeat length and percent methylation
with categorical calls and estimated methylation by SB.
Full mutations in Table 4 are shown in italics.

| | | mPCR | | | SB Analysis | |
|---|---|---|---|---|---|---|
| Sample ID | Sample Call | Repeat length (CGG) | Methyl-ation | X-acti-vation[a] | Categor-ical Call by SB[b] | Estimated methyl-ation by SB[c] |
| #120 | INT | 30 | 53% | | Partial | Inde-terminate |
| | | 53 | 52% | | (Faint) | |
| #121 | NOR | 30, 30 | 52% | 0.48 | Partial | 50% |
| #122 | NOR | 30, 30 | 51% | 0.49 | Partial | 50% |
| #123 | NOR | 30 | 87% | 0.13 | Partial | 50% |
| | | 31 | 8% | 0.92 | | |
| #124 | FM | >250 | 106% | | Full | 100% |
| #125[e] | FM | >250 | 0%[f] | | Non (faint smear) | Inde-terminate |

[a]Rousseau et al. and de Vries et al.; data available for certain samples only.
[b]Full = no evidence of banding <5.4 kb, Partial = evidence of banding in both regions of blot, Non = no evidence of banding >5.4 kb.
[c]Derived as a percent estimate of band intensity between methylated and unmethylated separated bands.
[d]Electropherogram and SB image shown in FIG. 6.
[e]Electropherogram and SB image shown in FIG. 5.
[f]Low abundance allele detected at 160 CGG (60% methylated)

TABLE 5

Concordance of mPCR and SB Analysis in Methylation Assessments of Clinical Samples with ≥55 CGG Repeats.

| Methylation Status of Clinical Samples with Alleles ≥55 CGG | | | mPCR | | | | | |
|---|---|---|---|---|---|---|---|---|
| | | | Fully methylated | | Partially methylated | | Un-methylated | |
| | | | PM | FM | PM | FM | PM | FM | Total |
| SB | Fully methyl-ated | PM | 2 | 0 | 0 | | 0 | | 26 |
| | | FM | 0 | 24 | | | | | |
| | Partially methyl-ated | PM | | | 17 | 0 | 0 | | 25 |
| | | FM | | | 0 | 8 | | | |
| | Un-methyl-ated | PM | 0 | | 0 | | 11 | 0 | 12 |
| | | FM | | | | | 0 | 1 | |
| | Total | | 26 | | 25 | | 12 | | 63 | mPCR results were in agreement with SB analysis, however, mPCR simplified and improved the detection and interpretation of different methylation states relative to SB. Due of the higher resolution of CE, some alleles that were readily distinguished by mPCR were unresolved by SB (such as two premutations of similar size). In these cases, alleles were grouped to match the resolution limits of SB analysis.

Figure 7:
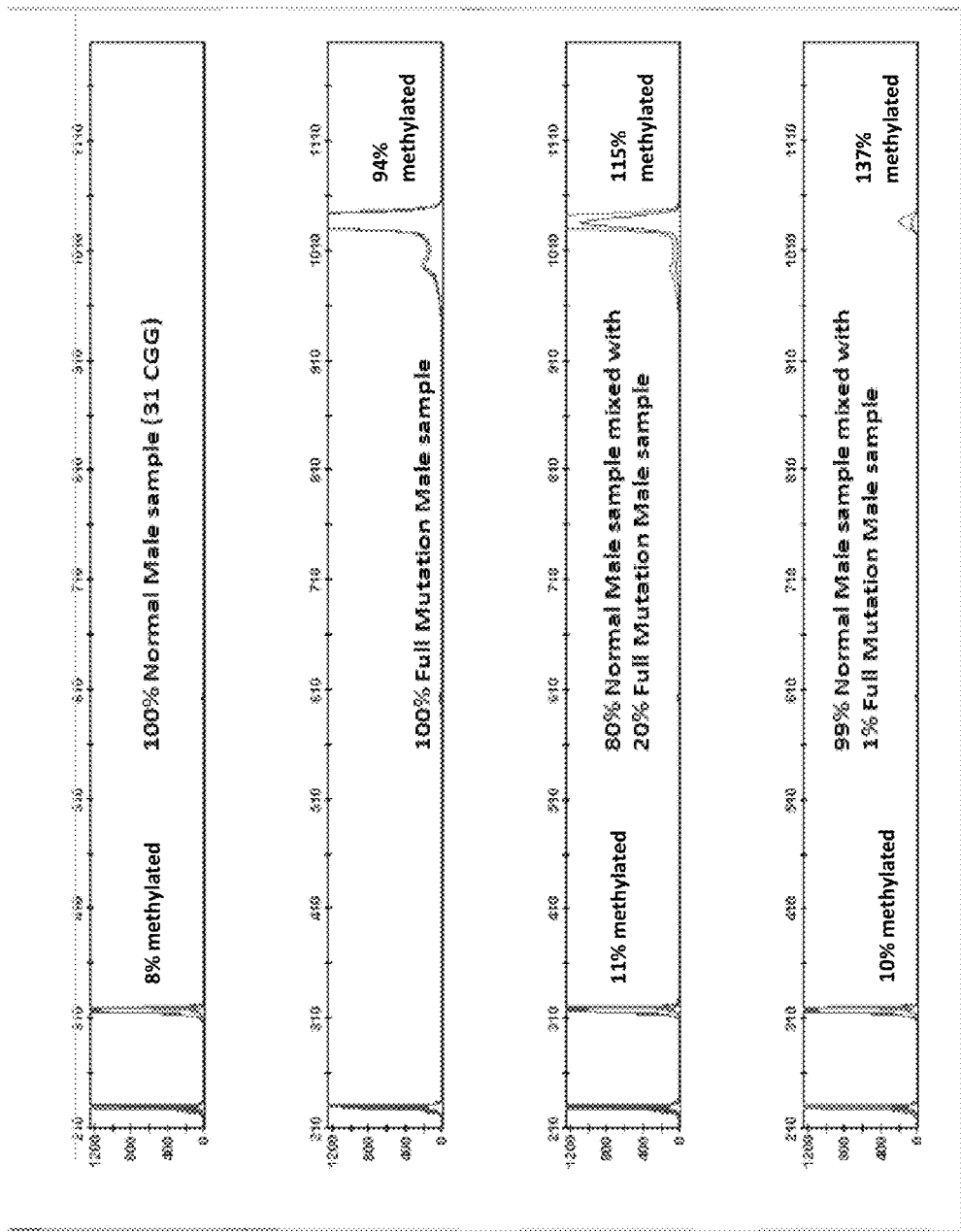
FIG. 7 shows titration of a 1% mass fraction of a clinical full mutation allele in a background of a normal 31 CGG allele in both the HEX™ and FAM™ channels.
Figure 8:
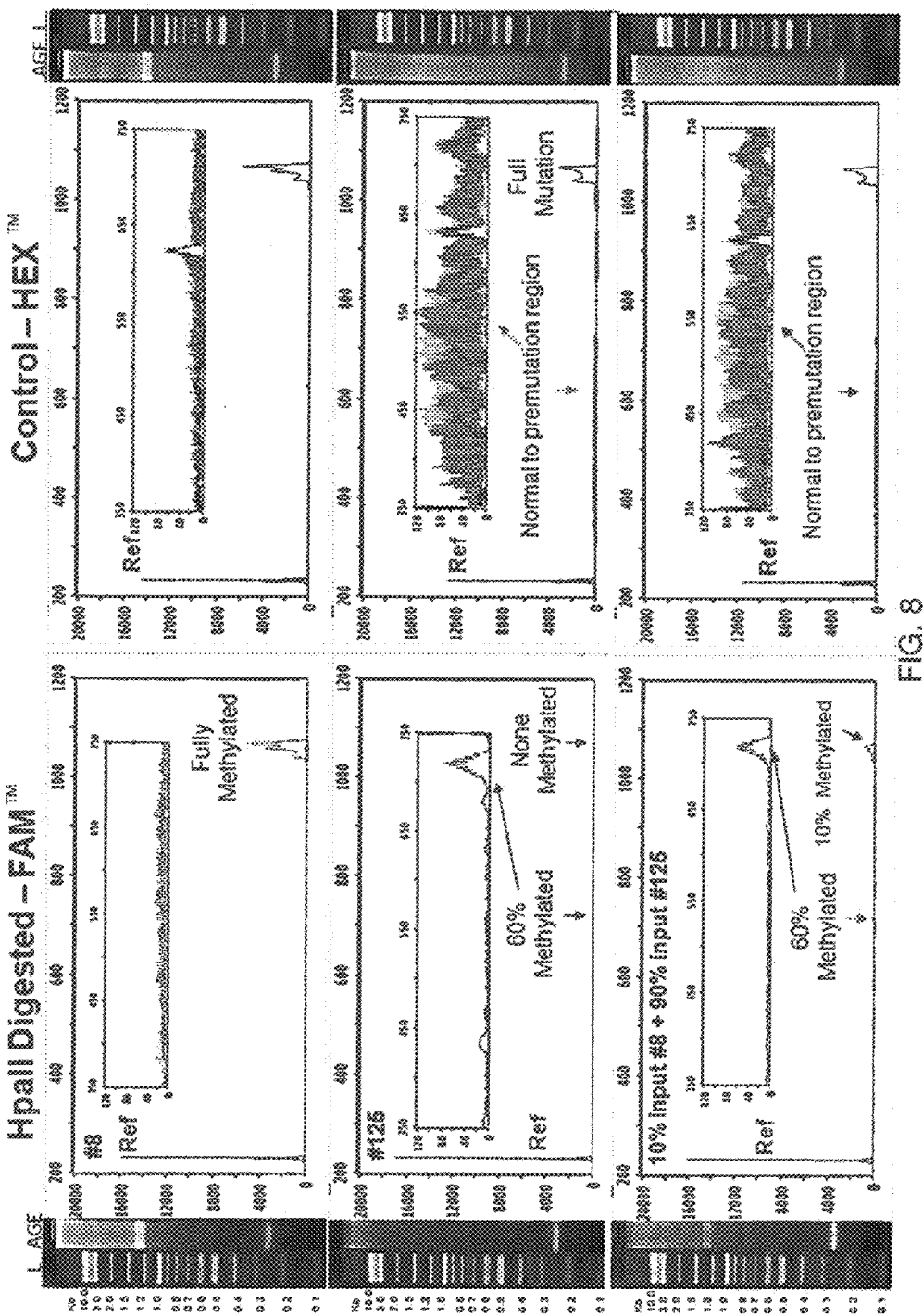
FIG. 8 shows titration of a 10% mass fraction of a fully methylated full mutation sample (#08) in the background of a 90% mass fraction of a fully unmethylated full mutation sample (#125).

The sensitivity of mPCR was addressed through two different experiments. In the first, titration of as little as a 1% mass fraction of a clinical full mutation allele in a background of a normal 31 CGG allele was detectable in both the HEX™ and FAM™ channels (FIG. 7). In the second, a 10% mass fraction of a fully methylated full mutation sample (#08) could be identified in the background of a 90% mass fraction of a fully unmethylated full mutation sample (#125) (FIG. 8). The methylation state of both samples was confirmed by SB analysis as shown in Table 4. Thus, consistent with FIG. 3, even a 10% methylation mosaic could be detected using clinical samples.

A. Identification and Resolution of Methylation Status in Full Mutation Alleles.

The electropherograms and matched SB images for representative full mutation samples are shown in FIG. 5. As previously described (Filipovic-Sadic, 2010), the CE configuration used in these experiments limited the differential resolution of amplicons to those with <250 CGG, and thus the amplification products of larger repeat expansions co-migrated, although the overall percentage methylation for the broad category of full mutations was accurately assessed as supported by the data below. For example, in the male full mutation sample #88 (FIG. 5A), the expanded allele was detected primarily in the methylated region of the SB with a faint product (~10-20% signal) in the unmethylated region. mPCR revealed 82% methylation for this sample, consistent with the SB result. Further, partial methylation for the normal allele, and full methylation for the expanded allele, was observed using SB for female full mutation sample #117 (FIG. 5B). The mPCR results also indicated partial (44%) methylation of the 30 CGG allele, and full (104%) methylation of the expanded allele.

mPCR simplified the identification of methylation status in more complex samples that can be problematic for SB. The male full mutation sample #125 (FIG. 5C) presented a low intensity smear across the unmethylated region (3 to >5 kb range). Using mPCR, the full mutation peak was clearly detected in the HEX™ but not the FAM™ channel despite amplification of the 40-CGG-Control. Thus, the full mutation allele was unmethylated. In another example (FIG. 5D), an unusual pattern of size and methylation mosaicism was resolved. By SB analysis, the full mutation allele appeared partially methylated, whereas mPCR revealed two distinct allele sizes with skewed methylation. The predominant full mutation signal was observed in the unmethylated longer template(s), whereas the less abundant template at ~200 CGG was fully methylated. Thus, the size mosaicism was more clearly resolved by mPCR, and the methylation pattern was more complex than that indicated by SB.

Figure 9:
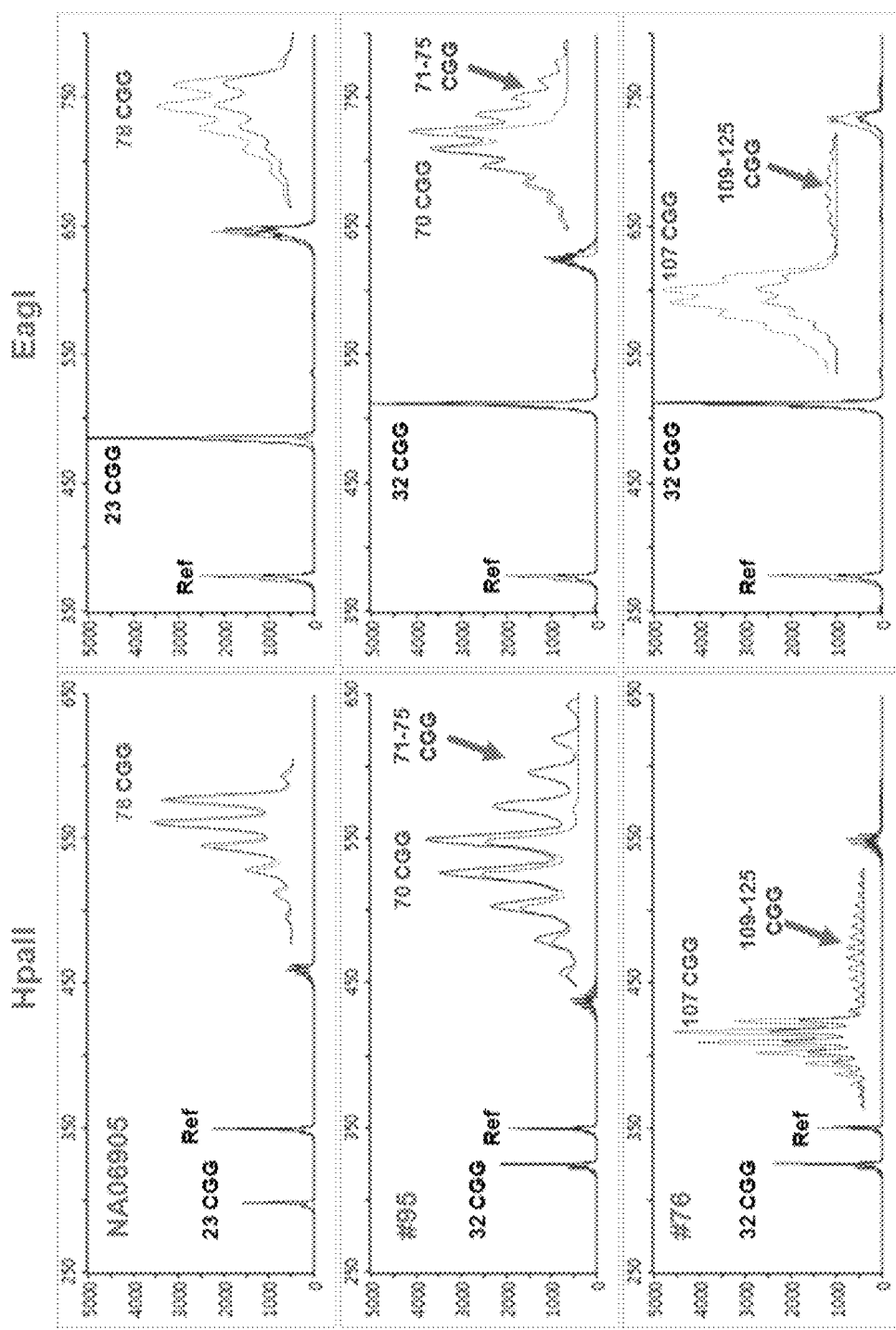
FIG. 9 shows a comparison of clinical samples analyzed using EagI or HpaII.

B. Identification of Novel Skewing Patterns in Female Premutation Alleles that were Masked by SB Analysis Electropherograms and matched SB images for 4 representative female premutation samples are shown in FIG. 6. The characteristic feature of each sample was the detection of two groups of repeat sizes for the longer allele, namely 53 and 54-56 CGG, 70 and 71-75 CGG, 90 and 92-101 CGG, and 107 and 109-125 CGG (FIGS. 6A-D, respectively). After digestion and amplification with FAM™-labeled primers, only the shorter CGG repeat lengths within each mosaic sample were detected. Because the size mosaicism was not observed in the Hpa II-treated FAM™ channel of characteristic female samples, nor was it observed after the PCR of any of the 11 tested male premutation alleles of comparable repeat length, it appears that this pattern was not an artifact of polymerase "stuttering". In each case, the more expanded CGG repeats of the premutation allele were completely unmethylated. This same mosaicism and skewed methylation pattern was identified in 84% (16 out of the 19) female premutation samples within the tested cohort. In contrast, the resolution limitations of SB yielded only one detectable premutation band and thus obscured this level of biological detail. In addition, the skewed mosaicism observed was not specific to an analysis of methylated HpaII sites. Specifically, the mPCR analysis was also performed with EagI rather than HpaII. EcoRI in Digestion Mix B was used for the control reaction. The EagI analysis utilized a CGG control migrating at a relative retention time of about −12.8 CGG repeats, and derived from a PCR amplicon instead of plasmid-based 40-CGG-Control. In addition, PCR primers were selected such that EagI recognition sites were present in the amplicon. The same pattern was observed when the template was treated with EagI, rather than HpaII, and analyzed using a modification of the mPCR method that permitted the assessment of EagI methylated sites (FIG. 9; "Ref" refers to the 40-CGG-Control in HpaII samples and −12.8 GCC control in EagI samples).

The mPCR research procedure can support high volume sample analyses, requiring only a single day and approximately 2 hrs of total hands-on time (much of which can be automated) to process up to 48 samples per operator. In addition, mPCR requires an input of only 80 ng of DNA—a 50- to 100-fold reduction compared to SB, and 10-fold reduction compared to bisulfite (Panagopoulos et al., *Hum Mutat* 14:71-9 (1999); Zhou et al., *Clin Chem* 52:1492-500 (2006); Dahl et al., *Nucleic Acids Res* 35:e144 (2007)) or previously reported HpaII-mediated PCR methods (Carrel et al., *Am J Med Genet* 64:27-30 (1996); Kline et al., *Fertil Steril* 85:1488-95 (2006); Allen et al., *Am J Hum Genet* 51:1229-39 (1992)). As a result, alternative sample types to whole blood that share an ectodermal cell lineage with neuronal cells, such as buccal or skin cells, may be amenable to mPCR analysis even if they do not provide sufficient DNA yields for SB.

The mPCR technology evaluated in this study represents a PCR-based methodology that detects and resolves methylation status across the spectrum of CGG repeat lengths in both male and female samples. The overall workflow is amenable to routine testing and high throughput screening applications. The methods provide the foundation for comprehensive FMR1 analyses without the requirement for SB analysis.

Example 6: mPCR with Alternate Methylation-Sensitive Enzymes

To demonstrate the versatility of the mPCR methods, selected clinical samples were analyzed using the enzymes EagI and NruI, as well as HpaII. Experiments were generally performed as described in Example 2, with samples treated with EagI or NruI in Digestion Mix B for 2 hours, and control samples treated with EcoRI in Digestion Mix B for 2 hours. A non-plasmid −12.8 CGG standard was used for EagI experiments, and a non-plasmid −41 CGG standard was used with NruI samples. PCR primers for EagI and NruI experiments were chosen such that the amplicon contained recognition sites for the appropriate enzymes. HpaII experiments were performed as described in Example 4. Table 6 compares the results of these experiments. Results using the various enzymes differentiated non-methylated vs. methylated alleles, as well as non-methylated, partially methylated, and fully methylated alleles.

TABLE 6

Comparison of HpaII, EagI, and NruI results

| Sample ID | Sample Call | Repeat length (CGG) | Hpa II Methylation | EagI Methylation | NruI Methylation |
|---|---|---|---|---|---|
| #72 | INT | 30 | 85% | 68% | 84% |
| | | 53 | 26% | 61% | 28% |
| | | 54-55 | 0% | 0% | 0% |
| #75 | PM | 32 | 57% | 45% | 63% |
| | | 90 | 99% | 66% | 101% |
| | | 92-101 | 0% | 0% | 0% |
| #76 | PM | 32 | 40% | 27% | 42% |
| | | 107 | 111% | 84% | 113% |
| | | 109-125 | 0% | 0% | 0% |
| #95 | PM | 32 | 75% | 53% | 62% |
| | | 70 | 46% | 36% | 49% |
| | | 71-75 | 0% | 0% | 0% |
| NA06905 | PM | 23 | 0% | 3% | 8% |
| | | 78 | 78% | 79% | 109% |

Example 7. Methylation PCR Assay Performance Using a "0 CGG" Reference Standard for Assessing Methylation at HpaII Sites The methylation status of 6 samples from the Coriell Cell Repository was assessed using the zero-CGG-Control that has a relative retention time outside of the range of detection of biological FMR1 alleles. Experiments were performed as described in Example 2, using HpaII or Sau3A1 (control) in Digestion Mix C, and 27 cycles of PCR. As shown in Table 7, the choice of reference standard did not alter the interpretation of the methylation data across the range of methylation status, from 2% methylation to quantitatively methylated. Results were compared to those generated using the 40-CGG-Control as described in Example 4.

TABLE 7

Comparison of FMR1 methylation status using a "40 CGG" and "0 CGG" reference standard.

| Sample File | Allele 1 | Size 1 | % Methylation | | Allele 2 | Size 2 | % Methylation | |
|---|---|---|---|---|---|---|---|---|
| | | | zero-CGG standard | 40-CGG standard | | | zero-CGG standard | 40-CGG standard |
| NA07862 | FM | >200 | 97% | 113% | | | | |
| NA06897 | FM | >200 | 45% | 27% | | | | |
| NA04025 | FM | >200 | 99% | 99% | | | | |
| NA09237 | FM | >200 | 101% | 107% | | | | |
| NA07537 | NOR | 29 | 6% | 6% | FM | >200 | 94% | 77% |
| NA20239 | NOR | 20 | 4% | 2% | PM | 198 | 97% | 81% |

Example 8. Control Nuclease

The methods described herein can include the use of an endonuclease in the control reaction to cleave the large genomic DNA outside the amplification region of the FMR1 locus, and reduce the size of DNA templates comparable to those in the methylation-sensitive digestion reaction and thus comparably favorable for PCR amplification.

Many restriction enzymes and their specific recognition sites are well characterized. A total of 14 commercially available restriction endonucleases were selected for testing, including Sau3A, EcoRI, NaeI, DpnI, HINDIII-HF®, NheI, TfiI, ApaLI, MluCI, NcoI, ScaI, StuI, XmnI and Hpy166II.

Examples of restriction enzymes that may be used in the method include Sau3A, EcoRI, NaeI, DpnI and HINDIII-HF®. Sau3A exhibited reduced selectivity with respect to cleavage of non-target sites on the template. EcoRI, NaeI, DpnI and HINDIII-HF® exhibited a high degree of selectivity, in that little to no cleavage of non-target sites in the template (i.e., the region of the FMR1 locus bounded by SEQ ID NOs: 40 and 41) was observed.

TABLE 8

Comparison of the restriction endonucleases tested in the control digestion reaction.

| Endonuclease | Recognition Sequence | Template selectivity |
|---|---|---|
| EcoR1 | G/AATTC | +++ |
| Sau3A | /GATC | + |
| Dpn1 | GA/TC | +++ |
| Nae1 | GCC/GGC | +++ |
| HINDIII-HF ® | A/AGCTT | +++ |

Example 9. Alternative Workflow for Characterizing Methylation Status

An alternative workflow for characterizing methylation status is shown in FIG. 10. In this workflow, a genomic DNA sample is premixed together with digestion control and the GC reference standard (referred to in the figure as CGG DNA control). Each portion of DNA mixture is subject to the treatment with methylation-sensitive nuclease (HpaII) or a control nuclease (HINDIII-HF®). Subsequently, the digested DNA mixture is subjected to PCR amplification using the respective FAM™-labeled primers (HINDIII-HF® reaction) or HEX™-labeled primers (HpaII reaction). The PCR products are then pooled and analyzed by capillary electrophoresis.

Both digestion control and GC reference standard migrate in the early window of the electropherogram and do not interfere with the sample-specific profile. The loss of the amplicons from digestion control in the HEX™-labeled PCR indicates the efficiency of the HpaII digestion. The GC reference standard is used to normalize signal intensity between the FAM™- and HEX™-labeled PCR products. Addition of GC reference standard prior to restriction enzyme digestion is used to normalize the variability of the amount of genomic DNA in each reaction. Therefore, the percentage of methylation by each allele is determined as a ratio of peak height between the digested (HEX™) and control reaction (FAM™) after normalization to the GC reference standard from the corresponding reaction.

Example 10. mPCR Assessment of Cell Line DNA in the Alternative Workflow and Comparisons with SB Analysis mPCR according to the alternative workflow of Example 9 was evaluated with 4 commercially available cell line DNA templates (Coriell Institute for Medical Research) that included normal, premutation, and full mutation alleles from both male and female samples. Each sample was premixed with digestion control comprising SEQ ID NO: 50 and GC reference standard in which the A, B, and C sequences comprised SEQ ID NOs 17, 48, and 39, respectively. After addition of the digestion control and GC reference standard, the sample was divided into two portions. One portion of the sample was subjected to HpaII digestion, while the other was subjected to HINDIII-HF® digestion as a control reaction. 25-27 cycles of PCR amplification was then performed with each of the two portions using labeled primers as in Example 9, and products were resolved by CE. DNA from the same cell lines was also analyzed by SB. Results for allele size and methylation status from mPCR and SB are summarized in Table 9. Electropherograms of the 4 samples with corresponding SB data are shown in FIGS. 11A-11D. In each figure, the top panel shows the portion of the sample treated with HINDIII-HF® as control, and the bottom panel reveals the same sample digested with HpaII. Each figure also includes the methylation percentage determined by mPCR.

For each sample, the mPCR results were consistently in agreement with the SB data. For example, the two male full mutation samples (NA07862 and NA06852) were measured as having ≥00% methylation by mPCR, consistent with the presence of product only in the methylated region for the allele >200CGG in the SB.

In addition, mPCR provided more detailed information for allele-specific methylation status in samples with complex mosaicism. For example, two mosaic female samples (NA06896, 23/96-140 and NA20242, 30/73) were detected with primary peaks on SB, but these samples also revealed low abundant peaks not visualized on SB (FIGS. 11C-11D) when analyzed by mPCR. The mPCR data also revealed the individual contribution of each allele to the methylation pattern on SB. For example, NA06896 was detected with fully methylated 113 CGG & 138 CGG alleles, and unmethylated larger alleles of 143 to >200CGG (FIG. 11C), which is consistent with partial methylated FM reported in SB.

TABLE 9

Comparison of mPCR and SB analysis for 4 cell line DNA samples. All samples giving measurements of 100% or greater methylation were categorically scored as "≥100%".

| Sample information | | | Coriell Catalog Repeat Length (CGG) | SB Analysis | | mPCR | | |
|---|---|---|---|---|---|---|---|---|
| Sample ID | Genotype | Sex | | Estimated Size (CGG) | Categorical Methylation (Full, Partial or Non) | % Digestion of Dig Ctrl. | mPCR Repeat Length | Methylation % on mPCR |
| NA07862 | FM | M | Full | 501-550 | Full | 98% | >200 | ≥100% |
| NA06852 | FM | M | Full | 660-990 | Full | 99% | >200 | ≥100% |
| NA06896 | FM | F | 23/95-140 | Normal | Partial | 98% | 23 | 35% |
|  |  |  |  | 148-201 | Partial |  | 113 | 92% |
|  |  |  |  |  |  |  | 138 | ≥100% |
|  |  |  |  |  |  |  | 154 | 4% |
|  |  |  |  |  |  |  | 199 | 5% |
|  |  |  |  |  |  |  | >200 | 12% |
| NA20242 | PM | F | 30/73 | 30 | Non | 99% | 30 | 11% |
|  |  |  |  | 73 | Partial |  | 73 | 72% |
|  |  |  |  |  |  |  | 97 | 12% |
|  |  |  |  |  |  |  | 104 | ≥100% |

Example 11. mPCR Assessment with Clinical DNA Specimens in the Alternative Workflow The mPCR assay according to the alternative workflow according to Example 9 was further evaluated with a set to 12 clinical specimens that represented a range of clinically relevant allele sizes and methylation status. Experiments were performed as described in Example 10. Results for allele size and methylation status from mPCR and comparison to SB are summarized in Table 10. Electropherograms of the samples marked with * in Table 10 are provided in FIGS. 12A-12G with corresponding SB data.

mPCR results were in good concordance with SB analysis. mPCR provided higher resolution and allowed for more detailed detection and interpretation of different methylation states than SB. Some alleles unresolved by SB were easily distinguished by mPCR (such as two alleles of similar size). For example, sample #7 contains 30 and 31 CGG alleles, which were not distinguishable by SB. In mPCR, these two alleles were clearly detected with methylated 30 CGG and unmethylated 31 CGG (FIG. 12F), thus revealing allele-specific methylation not detectable by SB analysis.

TABLE 10

Comparison of mPCR and SB analysis for 14 clinical samples. Samples marked with * are shown in FIG. 2. All samples with 100% or greater methylation were categorically scored as "≥100%".

| Sample Information | | mPCR | | | SB Analysis | |
|---|---|---|---|---|---|---|
| Sample ID | Sample Call | Diges-tion of Dig Ctrl. | mPCR Repeat Length | Methyl-ation % on mPCR | Categorical Methylation (Full, Partial or Non) | Estimated Methyl-ation by SB |
| #1* | FM | 99% | 80 | 3% | Non | 0% |
|  |  |  | 225 | ≥100% | Full | 90% |
|  |  |  | 249 | ≥100% |  |  |
|  |  |  | 256 | 85% |  |  |
|  |  |  | 268 | 73% |  |  |
|  |  |  | 271 | 54% |  |  |
| #2* | FM | 99% | 94 | 7% | ND | ND |
|  |  |  | 209 | ≥100% | Partial | 60% |
|  |  |  | 257 | 0% |  |  |
|  |  |  | 272 | 1% |  |  |
| #3* | FM | 99% | 240 | 90% | Partial | 70% |
|  |  |  | 257 | 72% |  |  |
|  |  |  | 272 | 31% |  |  |
| #4* | PM | 99% | 23 | 28% | Partial | 30% |
|  |  |  | 72 | 77% | Partial | 60% |
| #5* | PM | 99% | 41 | 7% | Non | 10% |
|  |  |  | 96 | ≥100% | Full | 90% |
|  |  |  | 101 | ≥100% |  |  |
|  |  |  | 114 | ≥100% |  |  |
| #6* | Nor | 99% | 30 | 76% | Partial | 50% |
|  |  |  | 31 | 9% |  |  |
| #7* | FM | 99% | 23 | 19% | Partial | 30% |
|  |  |  | 94 | 3% |  |  |
|  |  |  | 239 | 98% | Full | 100% |
|  |  |  | 257 | 90% |  |  |
|  |  |  | 271 | 96% |  |  |
| #8 | PM | 100% | 155 | ≥100% | N/A |  |
|  |  |  | 175 | 2% |  |  |
| #9 | PM | 99% | 41 | 43% |  |  |
|  |  |  | 57 | 16% |  |  |
| #10 | FM | 99% | 53 | 0% |  |  |
|  |  |  | 153 | 96% |  |  |
|  |  |  | 256 | 1% |  |  |
|  |  |  | 271 | 1% |  |  |
| #11 | FM | 99% | 198 | 74% |  |  |
|  |  |  | 213 | 84% |  |  |
|  |  |  | 257 | 63% |  |  |
|  |  |  | 272 | ≥100% |  |  |

TABLE 10-continued

Comparison of mPCR and SB analysis for 14 clinical samples. Samples marked with * are shown in FIG. 2. All samples with 100% or greater methylation were categorically scored as "≥100%".

| Sample Information | | mPCR | | | SB Analysis | |
| --- | --- | --- | --- | --- | --- | --- |
| | | % Diges- | | Methyl- | Categorical | Estimated |
| | | tion of | mPCR | ation | Methylation | Methyl- |
| Sample ID | Sample Call | Dig Ctrl. | Repeat Length | % on mPCR | (Full, Partial or Non) | ation by SB |
| #12 | FM | 98% | 149 | 19% | | |
| | | | 258 | ≥100% | | |
| | | | 268 | ≥100% | | |
| | | | 273 | ≥100% | | |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. The listing of steps in a method in a particular order is not to be construed as an indication that the steps must be performed in that order, except where there is an explicit indication to the contrary or the result of one step is required for occurrence of another step. For example, steps of "contacting a first portion of the sample with a methylation-sensitive DNase" and "adding a GC reference standard to the sample" may be performed in any order because neither step requires a result from the other. On the other hand, "subjecting the first portion and a second portion of the sample, each containing the GC reference standard, to a DNA amplification reaction" occurs after "adding a GC reference standard to the sample" because the subjecting step requires the presence of the GC reference in portions of the sample, which results from the adding step.

All references cited herein are incorporated herein by reference in their entirety. To the extent publications and patents or patent applications incorporated by reference contradict the invention contained in the specification, the specification will supersede any contradictory material.

What is claimed is:

1. A method of characterizing at least one FMR locus in a DNA sample comprising the steps of:
   a) contacting a first portion of the sample with a methylation-sensitive DNase;
   b) adding a GC reference standard to the sample, wherein the reference standard comprises a nucleic acid sequence of the formula: 5'-A-B-C-3', wherein A comprises at least 10 nucleotides from SEQ ID NO:40, B is a sequence of 150 to 200 nucleotides having at least 75% GC-richness, and C comprises at least 10 nucleotides from SEQ ID NO: 41; the reference standard has at least 75% GC-richness; and the reference standard has a relative retention time by capillary electrophoresis of (1) less than, or about 20 CGG repeats or (2) about 175 to about 225 CGG repeats;
   c) subjecting the first portion and a second portion of the sample, each containing the GC reference standard, to a DNA amplification reaction, wherein the amplified DNA in each portion is labeled with a different label; and
   d) analyzing the amplified DNA from the first and the second portion of the sample, wherein the analyzing comprises detecting each label to identify the amplified DNA in the first and second portions, performing capillary electrophoresis and characterizing the methylation status of the FMR locus by comparing the amplified DNA in the first and second portions of the sample, thereby determining a fractional methylation of the FMR locus.

2. The method of claim 1, wherein the GC reference standard is devoid of recognition sites for the methylation-sensitive DNase.

3. The method of claim 1, wherein the amplified DNA from the first and the second portion are analyzed in a single CE run.

4. The method of claim 1, wherein the GC reference standard has a relative retention time of less than, or about 20 CGG repeats.

5. The method of claim 1, wherein the GC reference standard has a relative retention time of less than, or about 3 CGG repeats.

6. The method of claim 1, wherein the GC reference standard has a relative retention time of about 175 to about 225 CGG repeats.

7. The method of claim 1, wherein the methylation-sensitive DNase is chosen from Hpa II, Eag I, or Nru I.

8. The method of claim 1, wherein the amplification reaction is capable of amplifying at least 200 CGG repeats.

9. The method of claim 8, wherein the amplification reaction comprises a dNTP mixture with a GC/AT ratio greater than 1.

10. The method of claim 9, wherein the GC/AT ratio is from about 2.5 to about 10.

11. The method of claim 1, wherein the FMR locus is an FMR1 locus.

12. The method of claim 1, wherein the GC reference standard is added to the sample after contacting the first portion with the DNase.

13. The method of claim 1, wherein the GC reference standard is added to the sample before contacting the first portion with the DNase.

14. The method of claim 1, further comprising contacting the second portion of the sample with a control enzyme.

15. The method of claim 14, wherein the control enzyme is chosen from EcoRI and Sau3A1.

16. The method of claim 14, wherein, the GC reference standard is added to the sample before contacting the first portion with the DNase and the control enzyme is chosen from HindIII-HF, EcoRI, DpnI, and NaeI.

17. The method of claim 1, further comprising adding a digestion control to the sample before contacting the first portion of the sample with the methylation-sensitive DNase.

18. The method of claim 17, wherein the digestion control has a relative retention time of less than, or about 3 CGG repeats, the GC reference standard has a relative retention time of less than, or about 3 CGG repeats, and the relative retention times of the digestion control amplification product and the reference standard differ by greater than, or about 4 CGG repeats.

19. A method of analyzing a human DNA sample comprising the steps of:
   a) contacting a first portion of the sample with a methylation-sensitive DNase;
   b) adding a GC reference standard to the sample, wherein the reference standard comprises a nucleic acid sequence of the formula: 5'-A-B-C-3', wherein A comprises at least 10 nucleotides from SEQ ID NO: 40, B is a sequence of 150 to 200 nucleotides having at least 75% GC-richness, and C comprises at least 10 nucleotides from SEQ ID NO: 41; the reference standard has at least 75% GC-richness; and the reference standard has a relative retention time by capillary electrophoresis of (1) less than, or about 20 CGG repeats or (2) about 175 to about 225 CGG repeats;
   c) subjecting the first portion and a second portion of the sample to a DNA amplification reaction, wherein the amplified DNA in each portion is labeled with a different label;
   d) analyzing the amplified DNA from the first and the second portion of the sample, wherein the analyzing comprises detecting each label to identify the amplified DNA in the first and second portions, performing capillary electrophoresis and characterizing the methylation status of the FMR locus, comparing the amplified DNA in the first and second portions of the sample; and
   (e) detecting a genotype associated with Fragile X syndrome, Fragile X-associated tremor ataxia syndrome, and/or Fragile X-associated primary ovarian insufficiency, thereby analyzing the human DNA sample.

20. A method of characterizing at least one FMR locus in a DNA sample comprising the steps of:

a) contacting a first portion of the sample with a methylation-sensitive DNase;

b) adding a GC reference standard to the sample, wherein the reference standard comprises a nucleic acid sequence of the formula: 5'-A-B-C-3', wherein A comprises at least 10 nucleotides from SEQ ID NO: 40, B is a sequence of 150 to 200 nucleotides having at least 75% GC-richness, and C comprises at least 10 nucleotides from SEQ ID NO: 41; the reference standard has at least 75% GC-richness; and the reference standard has a relative retention time by capillary electrophoresis of (1) less than, or about 20 CGG repeats or (2) about 175 to about 225 CGG repeats;

c) subjecting the first portion and a second portion of the sample, each containing the GC reference standard, to a DNA amplification reaction, wherein the amplified DNA in each portion is labeled with a different label;

d) analyzing the amplified DNA from the first and the second portion of the sample, wherein the analyzing comprises detecting each label to identify the amplified DNA in the first and second portions, performing capillary electrophoresis; and (e) characterizing the methylation status of the FMR locus as non-methylated, partially methylated, or fully methylated.

21. The method of claim 20, wherein the GC reference standard is devoid of recognition sites for the methylation-sensitive DNase.

22. The method of claim 20, wherein the amplified DNA from the first and the second portion are analyzed in a single CE run.

23. The method of claim 20, wherein the GC reference standard has a relative retention time of less than, or about 20 CGG repeats.

24. The method of claim 20, wherein the GC reference standard has a relative retention time of less than, or about 3 CGG repeats.

25. The method of claim 20, wherein the GC reference standard has a relative retention time of about 175 to about 225 CGG repeats.

26. The method of claim 20, wherein the methylation-sensitive DNase is chosen from Hpa II, Eag I, or Nru I.

27. The method of claim 20, wherein the amplification reaction is capable of amplifying at least 200 CGG repeats.

28. The method of claim 27, wherein the amplification reaction comprises a dNTP mixture with a GC/AT ratio greater than 1.

29. The method of claim 28, wherein the GC/AT ratio is from about 2.5 to about 10.

30. The method of claim 20, wherein the FMR locus is an FMR1 locus.

31. The method of claim 20, wherein the GC reference standard is added to the sample after contacting the first portion with the DNase.

32. The method of claim 20, wherein the GC reference standard is added to the sample before contacting the first portion with the DNase.

33. The method of claim 20, further comprising contacting the second portion of the sample with a control enzyme.

34. The method of claim 33, wherein the control enzyme is chosen from EcoRI and Sau3A1.

35. The method of claim 33, wherein the GC reference standard is added to the sample before contacting the first portion with the DNase and the control enzyme is chosen from HindIII-HF, EcoRI, DpnI, and NaeI.

36. The method of claim 20, further comprising adding a digestion control to the sample before contacting the first portion of the sample with the methylation-sensitive DNase.

37. The method of claim 36, wherein the digestion control has a relative retention time of less than, or about 3 CGG repeats, the GC reference standard has a relative retention time of less than about 3 CGG repeats, and the relative retention times of the digestion control amplification product and the reference standard differ by grater than, or about 4 CGG repeats.

* * * * *

```
SEQUENCE LISTING

<160> NUMBER OF SEQ ID NOS: 62

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggtggaggg ccgcctctga gc                                             22

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caggcgctca gctccgtttc ggttt                                          25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagtcaggcg ctcagctccg tttcg                                          25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 4
tccggtggag ggccgcctct gagc                                      24

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggttcggcct cagtcaggcg ctcagctccg tttcg                          35

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggttcggcc tcagtcaggc gctcagctcc gtttcg                         36

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gcgggccggg ggttcggcct cagtca                                    26

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagcgggccg ggggttcggc ctcag                                     25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcagcgggcc gggggttcgg cctca                                     25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
gggccggggg ttcggcctca gtcag                                          25
```

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

```
ggggttcggc ctcagtcagg cgctca                                         26
```

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
ggggttcggc ctcagtcagg cgctcag                                        27
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
ggcgctcagc tccgtttcgg tttcacttcc                                     30
```

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
tcaggcgctc agctccgttt cggtttca                                       28
```

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
cacttccggt ggagggccgc ctctga                                         26
```

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttccggtgga gggccgcctc tgagc                                              25

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcgctcagct ccgtttcggt                                                    20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cacctctcgg gggcgggctc c                                                  21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
acctctcggg ggcgggctcc c                                                  21

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atggaggagc tggtggtgga agtgcg                                             26

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cacctctcgg gggcgggctc ccg                                                23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
acctctcggg ggcgggctcc cgg                                                23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cacctctcgg gggcgggctc ccgg                                          24

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cacctctcgg gggcgggctc ccggcg                                        26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acctctcggg ggcgggctcc cggcgc                                        26

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acctctcggg ggcgggctcc cggcg                                         25

<210> SEQ ID NO 27
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tggtggaagt gcggggctcc aatggcgc                                      28

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tggaagtgcg gggctccaat ggcgc                                         25

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggaagtgcgg ggctccaatg gcgct                                           25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtggaagtgc ggggctccaa tggcg                                           25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tggtggtgga agtgcggggc tccaa                                           25

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gaggagctgg tggtggaagt gcggggct                                        28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aggagctggt ggtggaagtg cggggctc                                        28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctggtggtgg aagtgcgggg ctccaatg                                        28

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
agatggagga gctggtggtg gaagtgcggg                                30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggaagtgcgg ggctccaatg gcgctttcta                                30

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ggaagtgcgg ggctccaatg gcgctt                                    26

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tggaggagct ggtggtggaa gtgcg                                     25

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
agtgcggggc tccaatggcg                                           20

<210> SEQ ID NO 40
<211> LENGTH: 478
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40
ccgcggaatc ccagagaggc cgaactggga taaccggatg catttgattt cccacgccac    60
tgagtgcacc tctgcagaaa tgggcgttct ggccctcgcg aggcagtgcg acctgtcacc   120

```
gcccttcagc cttcccgccc tccaccaagc ccgcgcacgc ccggcccgcg cgtctgtctt      180
tcgacccggc accccggccg gttcccagca gcgcgcatgc gcgcgctccc aggccacttg      240
aagagagagg gcggggccga ggggctgagc ccgcgggggg agggaacagc gttgatcacg      300
tgacgtggtt tcagtgttta cacccgcagc gggccgggg ttcggcctca gtcaggcgct       360
cagctccgtt tcggtttcac ttccggtgga gggccgcctc tgagcgggcg cggggccgac     420
ggcgagcgcg ggcggcggcg gtgacggagg cgccgctgcc aggggggcgtg cggcagcg     478
```

```
<210> SEQ ID NO 41
<211> LENGTH: 500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
```

```
ctgggcctcg agcgcccgca gcccacctct cggggggcggg ctcccggcgc tagcagggct     60
gaagagaaga tggaggagct ggtggtggaa gtgcggggct ccaatggcgc tttctacaag     120
gtacttggct ctagggcagg ccccatcttc gcccttcctt ccctcccttt tcttcttggt    180
gtcggcggga ggcaggcccg ggccctcttc ccgagcacc gcgcctgggt gccagggcac      240
gctcggcggg atgttgttgg gagggaagga ctggacttgg ggcctgttgg aagcccctct     300
ccgactccga gaggccctag cgcctatcga aatgagagac cagcgaggag agggttctct    360
ttcggcgccg agccccgccg gggtgagctg gggatgggcg agggccggcg gcaggtacta     420
gagccgggcg ggaagggccg aaatcggcgc taagtgacgg cgatggctta ttccccctttt   480 cctaaacatc atctcccagc                                                500
```

```
<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tcaggcgctc agctccgttt cggtttca                                        28
```

```
<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aagcgccatt ggagccccgc acttcc                                          26
```

```
<210> SEQ ID NO 44
<211> LENGTH: 400
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
aagcttcagc gggccggggg ttcggcctca gtcaggcgct cagctccgtt tcggtttcac     60
```

```
ttcccgtgga gggccgcctc tgagcgggcg gcgggccgac ggcgagcgcg ggcggcggcg    120
gtgacggagg cgccgctgcc aggggggcgtg cggcagcgcg gcggcggcgg cggcggcggt    180
ggcgacggag gcggcggcgg cgtcggcggc ggcagcggag gcggcggcgg cggcggcggc    240
ggcggcggct gggcctcgtg cgcccgcagc ccacctcttg ggggcggtct ccccgcgcta    300
gcagggctga agagaagaca gtgttcattc atcgccatca gctgcagctg gaggagctgg    360
tggtggaagt gcggggctcc aatggcgctt tctaggatcc                          400
```

<210> SEQ ID NO 45
<211> LENGTH: 248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
gaattctcag gcgctcagct ccgtttcggt ttcacgctgc caggggggcgt gcggcagcgc     60 ggcggcggag gcggcggcgg cggcggcggc ggcggcggtg gaggcggcgg cggcggcggc    120
ggcggcggcg gcggcggcgg aggcggccggc ggcggcggcg gcggcggcgg cggcggcgga    180
ggcggcggcg gctgggcctc gagcgcccgc agcccaggaa gtgcggggct ccaatggcgc    240
ttgtcgac                                                            248
```

<210> SEQ ID NO 46
<211> LENGTH: 127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46

```
tcaggcgctc agctccgttt cggtttcact tccggtggag ggccgcctct gagcgggcgg     60
cgggccgacg gcgagcgcgg gcggcggcgg tgacggaggc gccgctgcca gggggcgtgc    120
ggcagcg                                                             127
```

<210> SEQ ID NO 47
<211> LENGTH: 112
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
ctgggcctcg agcgcccgca gcccacctct cggggggcggg ctccggcgc tagcagggct     60 gaagagaaga tggaggagct ggtggtggaa gtgcggggct ccaatggcgc tt            112
```

<210> SEQ ID NO 48
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
cggcggcgga ggcggcggcg gcggcggcgg cggcggcggt ggaggcggcg gcggcggcgg     60
```

```
cggcggcggc ggcggcggcg gaggcggcgg cggcggcggc ggcggcggcg gcggcggcgg      120
aggcggcggc gg                                                         132

<210> SEQ ID NO 49
<211> LENGTH: 132
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
cggcggcgga ggcggcggcg gcggcggcgg cggcggcggc ggaggcggcg gcggcggcgg      60
cggcggcggc ggcggcggcg gaggcggcgg cggcggcggc ggcggcggcg gcggcggcgg      120
aggcggcggc gg                                                         132

<210> SEQ ID NO 50
<211> LENGTH: 223
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
tcaggcgctc agctccgttt cggtttcacg gtgacggagg cgccgctgcc cgggggcgtg      60
cggcagcgcg gcggcggcgg cggcggcggc ggcggcggcg gcggcggcgg cggcggcggc      120
ggcggcggcg gcggcggcgg cggcggcggc ggcggcggcg gcggcggctg ggcctcgagc      180
gcccgcagcc caggaagtgg aagtgcgggg ctccaatggc gct                       223

<210> SEQ ID NO 51
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 51
gacnnnnngt c                                                          11

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 52 cacnnnngtg                                                            10

<210> SEQ ID NO 53
<211> LENGTH: 11
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(6)
<223> OTHER INFORMATION: a, c, t, g, unknown or other

<400> SEQUENCE: 53
acnnnngtay c                                                              11

<210> SEQ ID NO 54
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 54
cgannnnnnt gc                                                             12

<210> SEQ ID NO 55
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 55
gccnnnnngg c                                                              11

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 56 gatnnnnatc                                                                10

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 57
ccnnnnnnng g                                                              11
```

```
<210> SEQ ID NO 58
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 58
gcannnnntg c                                                          11

<210> SEQ ID NO 59
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(9)
<223> OTHER INFORMATION: a, c, t, g, unknown or other

<400> SEQUENCE: 59
gacnnnnnng tc                                                         12

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(9)
<223> OTHER INFORMATION: a, c, t, g, unknown or other

<400> SEQUENCE: 60
gcnnnnnnng c                                                          11

<210> SEQ ID NO 61
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(7)
<223> OTHER INFORMATION: a, c, t, g, unknown or other

<400> SEQUENCE: 61 gacnnnngtc                                                            10

<210> SEQ ID NO 62
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
```

```
<222> LOCATION: (5)..(9)
<223> OTHER INFORMATION: a, c, t, g, unknown or other

<400> SEQUENCE: 62
ggccnnnnng gcc                                                        13
```